United States Patent
Gregory et al.

(10) Patent No.: US 9,937,207 B2
(45) Date of Patent: Apr. 10, 2018

(54) TARGETED DISRUPTION OF T CELL RECEPTOR GENES USING TALENS

(71) Applicants: Sangamo BioSciences, Inc., Richmond, CA (US); Ospedale San Raffaele srl, Milan (IT)

(72) Inventors: Philip D. Gregory, Richmond, CA (US); Michael C. Holmes, Richmond, CA (US); David Paschon, Richmond, CA (US); Lei Zhang, Richmond, CA (US); Maria Chiara Bonini, Milan (IT); Pietro Genovese, Milan (IT); Zulma Magnani, Milan (IT); Sara Mastaglio, Milan (IT); Luigi Naldini, Milan (IT)

(73) Assignees: Sangamo Therapeutics, Inc., Richmond, CA (US); Ospedale San Raffaele SRL, Milan (IT)

(*) Notice: Subject to any disclaimer, the term of this patent is extended or adjusted under 35 U.S.C. 154(b) by 268 days.

(21) Appl. No.: 14/221,074

(22) Filed: Mar. 20, 2014

(65) Prior Publication Data

US 2014/0301990 A1 Oct. 9, 2014

Related U.S. Application Data

(60) Provisional application No. 61/804,076, filed on Mar. 21, 2013.

(51) Int. Cl.
*C12N 15/87* (2006.01)
*A61K 35/26* (2015.01)
*A61K 39/00* (2006.01)

(52) U.S. Cl.
CPC .......... *A61K 35/26* (2013.01); *A61K 39/0011* (2013.01); *C12N 15/87* (2013.01); *A61K 2039/5156* (2013.01); *A61K 2039/5158* (2013.01); *C12N 2501/515* (2013.01); *C12N 2510/00* (2013.01)

(58) Field of Classification Search
CPC .... A61K 2039/5158; A61K 2039/5156; A61K 39/0011; A61K 35/26; C12N 2501/515; C12N 2510/00; C12N 15/87
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas, III |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,503,717 B2 | 1/2003 | Case et al. |
| 6,534,261 B1 | 3/2003 | Cox et al. |
| 6,599,692 B1 | 7/2003 | Case et al. |
| 6,607,882 B1 | 8/2003 | Cox et al. |
| 6,689,558 B2 | 2/2004 | Case |
| 6,794,136 B1 | 9/2004 | Eisenberg et al. |
| 6,824,978 B1 | 11/2004 | Cox et al. |
| 6,933,113 B2 | 8/2005 | Case et al. |
| 6,979,539 B2 | 12/2005 | Cox et al. |
| 7,013,219 B2 | 3/2006 | Case et al. |
| 7,163,824 B2 | 1/2007 | Cox et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller et al. |
| 8,110,379 B2 | 2/2012 | DeKelver et al. |
| 8,367,804 B2 | 2/2013 | Boulter et al. |
| 8,409,861 B2 | 4/2013 | Guschin et al. |
| 8,586,526 B2 | 11/2013 | Gregory et al. |
| 8,623,618 B2 | 1/2014 | Doyon et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0063231 A1 | 3/2006 | Li et al. |
| 2006/0200869 A1 | 9/2006 | Naldini |
| 2007/0134796 A1 | 6/2007 | Holmes et al. |

(Continued)

FOREIGN PATENT DOCUMENTS

| | | |
|---|---|---|
| EP | 1956080 B1 | 9/2011 |
| EP | 2016102 B1 | 3/2012 |

(Continued)

OTHER PUBLICATIONS

Provasi et al. "Editing T cell specificity towards leukemia by zinc finger nucleases and lentiviral gene transfer." Nat Med. May 2012;18(5):807-15.*
Provasi et al. Supplementary Information. "Editing T cell specificity towards leukemia by zinc finger nucleases and lentiviral gene transfer." Nat Med. May 2012;18(5:) pp. 1-13.*
Zhao et al. "Primary human lymphocytes transduced with NY-ESO-1 antigen-specific TCR genes recognize and kill diverse human tumor cell lines." J Immunol. Apr. 1, 2005;174(7):4415-23.*
Abad, et al., "T-Cell Receptor Gene Therapy of Established Tumors in a Murine Melanoma Model," *J. Immunother.* 31(1):1-6 (2008).

(Continued)

*Primary Examiner* — Titilayo Moloye
(74) *Attorney, Agent, or Firm* — Pasternak Patent Law; Susan Abrahamson

(57) ABSTRACT

Disclosed herein are methods and compositions for modifying TCR genes, using nucleases (zinc finger nucleases or TAL nucleases) to modify TCR genes.

13 Claims, 31 Drawing Sheets

(56) References Cited

U.S. PATENT DOCUMENTS

| | | |
|---|---|---|
| 2008/0015164 A1 | 1/2008 | Collingwood |
| 2008/0131962 A1 | 6/2008 | Miller |
| 2008/0159996 A1 | 7/2008 | Ando et al. |
| 2008/0299580 A1 | 12/2008 | DeKelver et al. |
| 2009/0117617 A1 | 5/2009 | Holmes et al. |
| 2010/0003756 A1 | 1/2010 | Collingwood et al. |
| 2010/0047805 A1 | 2/2010 | Wang |
| 2010/0218264 A1 | 8/2010 | Cui et al. |
| 2010/0273213 A1* | 10/2010 | Mineno ............ C07K 14/7051 435/69.1 |
| 2010/0291048 A1 | 11/2010 | Holmes et al. |
| 2011/0129898 A1 | 6/2011 | Doyon |
| 2011/0158957 A1* | 6/2011 | Bonini ................ C12N 9/22 424/93.7 |
| 2011/0201055 A1 | 8/2011 | Doyon et al. |
| 2011/0207221 A1 | 8/2011 | Cost et al. |
| 2011/0239315 A1 | 9/2011 | Bonas et al. |
| 2011/0265198 A1 | 10/2011 | Gregory et al. |
| 2011/0281361 A1 | 11/2011 | DeKelver et al. |
| 2011/0301073 A1* | 12/2011 | Gregory .............. C12N 15/62 514/1.1 |
| 2012/0017290 A1 | 1/2012 | Cui et al. |
| 2012/0060230 A1* | 3/2012 | Collingwood ... C07K 14/70539 800/9 |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2013/0326645 A1 | 12/2013 | Cost et al. |

FOREIGN PATENT DOCUMENTS

| | | | |
|---|---|---|---|
| FR | WO 2012138927 A2 * | 10/2012 | ............ C12N 9/22 |
| GB | 2338237 A | 12/1999 | |
| WO | WO 95/19431 A1 | 7/1995 | |
| WO | WO 96/06166 A1 | 2/1996 | |
| WO | WO 98/37186 A1 | 8/1998 | |
| WO | WO 98/53057 A1 | 11/1998 | |
| WO | WO 98/53058 A1 | 11/1998 | |
| WO | WO 98/53059 A1 | 11/1998 | |
| WO | WO 98/53060 A1 | 11/1998 | |
| WO | WO 98/54311 A1 | 12/1998 | |
| WO | WO 00/27878 A1 | 5/2000 | |
| WO | WO 01/60970 A2 | 8/2001 | |
| WO | WO 01/88197 A2 | 11/2001 | |
| WO | WO 02/16536 A1 | 2/2002 | |
| WO | WO 02/077227 A2 | 10/2002 | |
| WO | WO 02/099084 A2 | 12/2002 | |
| WO | WO 2007/014275 A2 | 2/2007 | |
| WO | WO 2007/139898 A2 | 12/2007 | |
| WO | WO 03/016496 A2 | 2/2008 | |
| WO | WO 2010/079430 A1 | 7/2010 | |
| WO | 2013012667 | 1/2012 | |
| WO | 2012/138939 A1 | 10/2012 | |
| WO | 2013074916 | 5/2013 | |

OTHER PUBLICATIONS

Beerli, et al., "Engineering Polydactyl Zinc-Finger Transcription Factors," *Nature Biotechnol.* 20:135-141 (2002).

Bendle, et al., "Lethal Graft-Versus-Host Disease in Mouse Models of T Cell Receptor Gene Therapy," *Nature Medicine* 16(5):565-570 (2010).

Beurdeley, et al., "Compact Designer Talens for Efficient Genome Engineering," *Nature Communications* 4:1762 (2013) doi:10.10.38/ncomms2782.

Bitinaite, et al., "Foki Dimerization Is Required for DNA Cleavage," *PNAS USA* 95:10570-10575 (1998).

Bondanza, et al., "IL-7 Receptor Expression Identifies Suicide Gene-Modified Allospecific CD8+ T Cells Capable of Self-Renewal and Differentiation Into Antileukemia Effectors," *Blood* 117:6469-6478 (2011).

Boissel, et al., "Megatals: A Rare-Cleaving Nuclease Architecture for Therapeutic Genome Engineering," *Nucl. Acid Res.* 1-13 (2013) doi:10.1093/nar/gkt1224.

Bonas, et al., "Genetic and Structural Characterization of the Avirulence Gene AVRBS3 From *Xanthomonas campestris* pv. Vesicatoria," *Mol. Gen. Genet.* 218:127-136 (1989).

Boon, et al., "Human T Cell Responses Against Melanoma," *Annu. Rev. Immunol.* 24:175-208 (2006).

Burns, et al., "Lack of Specific Y-Retroviral Vector Long Terminal Repeat Promoter Silencing in Patients Receiving Genetically Engineered Lymphocytes and Activation Upon Lymphocyte Restimulation," *Blood* 114(14):2888-2899 (2009).

Choo, et al., "Advances in Zinc Finger Engineering," *Curr. Opin. Struct. Biol.* 10:411-416 (2000).

Dudley, et al., "Adoptive Cell Therapy for Patients With Metastatic Melanoma: Evaluation of Intensive Myeloablative Chemoradiation Preparative Regimens," *J. Clin. Oncol.* 26(32):5233-5239 (2008).

Dudley, et al., "Cancer Regression and Autoimmunity in Patients After Clonal Repopulation With Antitumor Lymphocytes," *Science* 298(5594):850-854 (2002).

Follenzi and Naldini, "Generation of HIV-1 Derived Lentiviral Vectors," *Methods in Enzymology* 346:454-465 (2002).

Gnjatic, et al., "NY-ESO-1: Review of an Immunogenic Tumor Antigen," *Advances in Cancer Research* 95:1-30 (2006).

Heuer, et al., "Repeat Domain Diversity of AVRBS3-Like Genes in Ralstonia Solanacearum Strains and Association With Host Preferences in the Field," *Appl. and Envir. Micro.* 73:4379-4384 (2007).

Holst, et al., "Generation of T-Cell Receptor Retrogenic Mice," *Nat. Protoc.* 1(1):406-417 (2006).

Inoue, et al., "Aberrant Overexpression of the Wilms Tumor Gene (WT1) in Human Leukemia," *Blood* 89(4):1405-1412 (1997).

Isalan, et al., "A Rapid, Generally Applicable Method to Engineer Zinc Fingers Illustrated by Targeting the HIV-1 Promoter," *Nature Biotechnology* 19(7):656-660 (2001).

Kaneko, et al., "IL-7 and IL-15 Allow the Generation of Suicide Gene-Modified Alloreactive Self-Renewing Central Memory Human T Lymphocytes," *Blood* 113(5):1006-1015 (2009).

Kay, et al., "A Bacterial Effector Acts as a Plant Transcription Factor and Induces a Cell Size Regulator," *Science* 318:648-651 (2007).

Kim, et al., "Chimeric Restriction Endonuclease," *PNAS USA* 91:883-887 (1994).

Kim, et al., "Insertion and Deletion Mutants of Foki Restriction Endonuclease," *J. Biol. Chem.* 269:31978-31982 (1994).

Kuball, et al., "Facilitating Matched Pairing and Expression of TCR Chains Introduced Into Human T Cells," *Blood* 109(6):2331-2338 (2007).

Li, et al., "Alteration of the Cleavage Distance of Fok I Restriction Endonuclease by Insertion Mutagenesis," *PNAS USA* 90:2764-2768 (1993).

Li, et al., "Functional Domains in Fok I Restriction Endonuclease," *PNAS USA* 89:4275-4279 (1992).

Lombardo, et al., "Gene Editing in Human Stem Cells Using Zinc Finger Nucleases and Integrase-Defective Lentiviral Vector Delivery," *Nat. Biotech.* 25(11):1298-1306 (2007).

Morgan, et al., "Cancer Regression in Patients After Transfer of Genetically Engineered Lymphocytes," *Science* 314(5796):126-129 (2006).

Pabo, et al., "Design and Selection of Novel CYS2HIS2 Zinc Finger Proteins," *Ann. Rev. Biochem.* 70:313-340 (2001).

Perez, et al., "Estabishment of HIV-1 Resistance in CD4+T Cells by Genome Editing Using Zinc-Finger Nucleases," *Nature Biotechnology* 26:808-816 (2008).

Robbins, et al., "Tumor Regression in Patients With Metastatic Synovial Cell Sarcoma and Melanoma Using Genetically Engineered Lymphocytes Reactive With NY-ESO-1," *J. Clin. Oncol.* 29(7):917-924 (2011).

Rosenburg, et al., "Cancer Immunotherapy: Moving Beyond Current Vaccines," *Nat. Med.* 10(9):909-915 (2004).

Rubenstein, et al., "Transfer of TCR Genes Into Mature T Cells is Accompanied by the Maintenance of Parental T Cell Avidity," *J. of Immunology* 170:1209-1217 (2003).

(56) References Cited

OTHER PUBLICATIONS

Schornack, et al., "Gene-For-Gene-Mediated Recognition of Nuclear-Targeted AVRBS3-Like Bacterial Effector Proteins," *J. Plant Physiol.* 163:256-272 (2006).

Segal, et al., "Custom DNA-Binding Proteins Come of Age: Polydactyl Zinc-Finger Proteins," *Curr. Opin. Biotechnol.* 12(6):632-637 (2001).

Sommermeyer, et al., "NY-ESO-1 Antigen-Reactive T Cell Receptors Exhibit Diverse Therapeutic Capability," *Int. J. Cancer* 132:1360-1367 (2012).

Sujita, et al., "NY-ESO-1 Expression and Immunogenicity in Malignment and Benign Breast Tumors," *Cancer Research* 64:2199-2204 (2004).

Thomas, et al., "Targeting the Wilms Tumor Antigen 1 by TCR Gene Transfer: TCR Variants Improve Tetramer Binding but Not the Function of Gene Modified Human T Cells," *J. of Immunol.* 179(9):5803-5810 (2007).

Urnov, et al., Highly Efficient Endongenous Human Gene Correction Using Designed Zinc-Finger Nucleases, *Nature* 435(7042):646-651 (2005).

Van Loenen, et al., "Mixed T Cell Receptor Dimers Harbor Potentially Harmful Neoreactivity," *PNAS USA* 107(24):10972-10977 (2010).

Torikai, et al., "A Foundation for Universal T-Cell Based Immunotherapy: T Cells Engineered to Express a CD19-Specific Chimeric-Antigen-Receptor and Eliminate Expression of Endogenous TCR," *Blood* 119(24):5697-5705 (2012).

Zhao, et al., "Primary Human Lymphocytes Transduced With NY-ESO-1 Antigen-Specific TCR Genes Recognize and Kill Diverse Human Tumor Cell Lines," The Journal of Immunology 174(7):4415-4423 (2005).

* cited by examiner

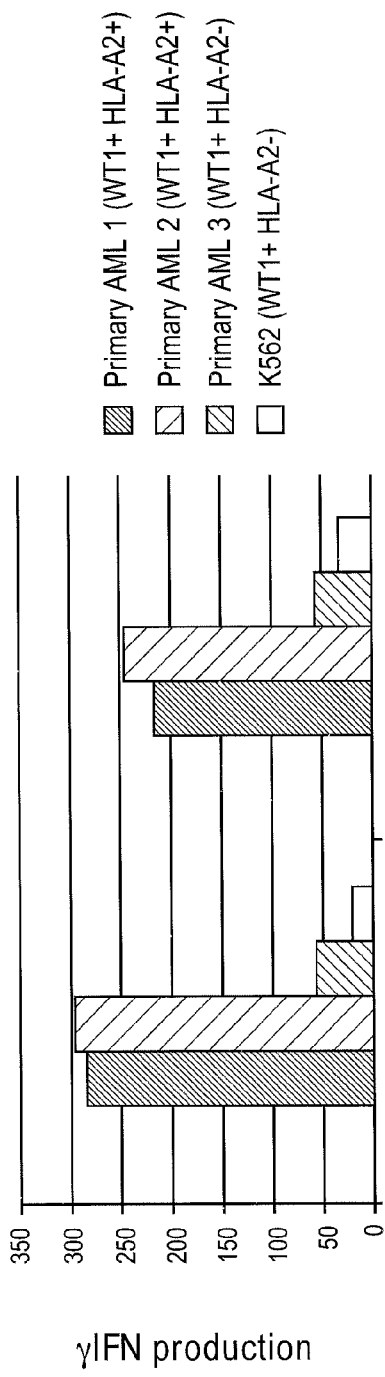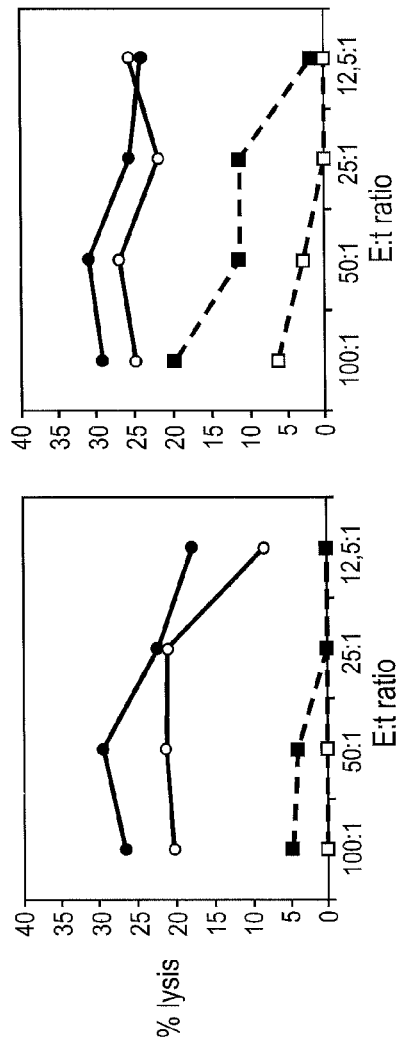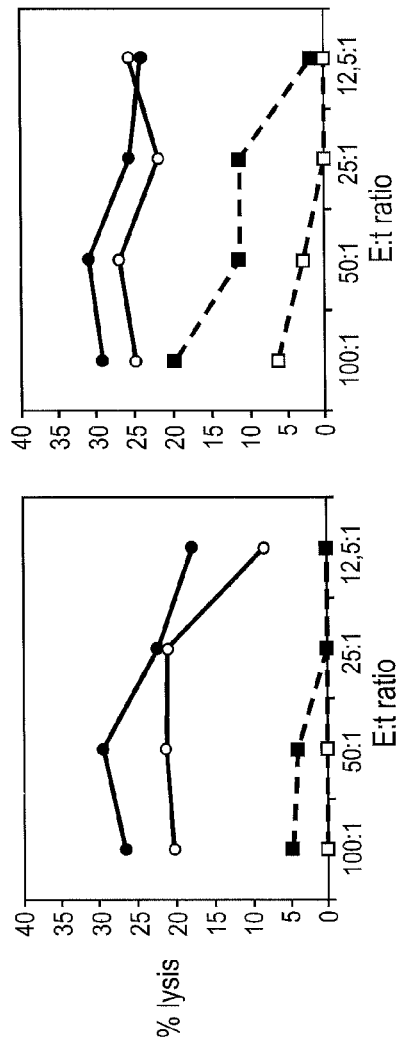
FIG. 2A
FIG. 2B
FIG. 2C

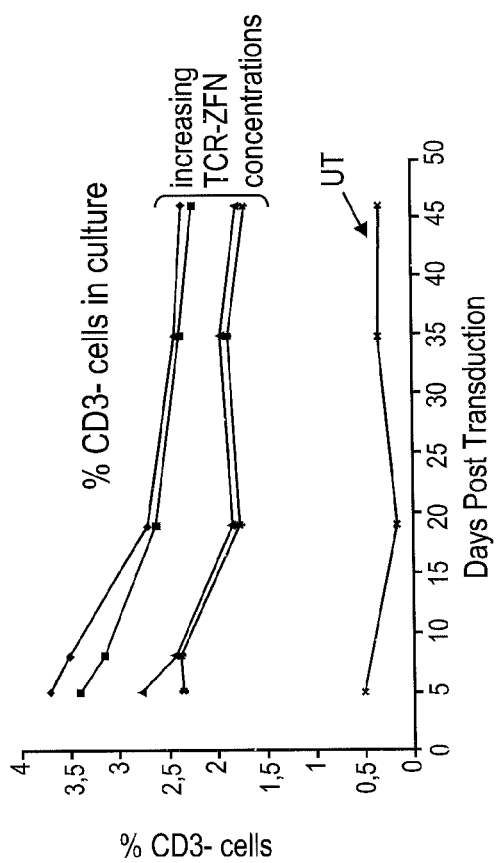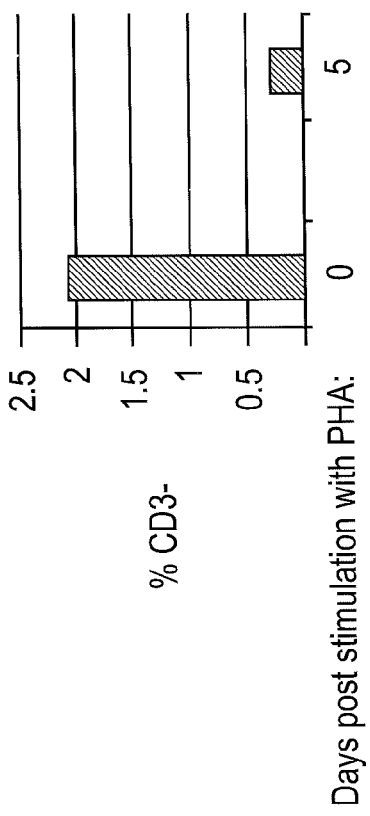

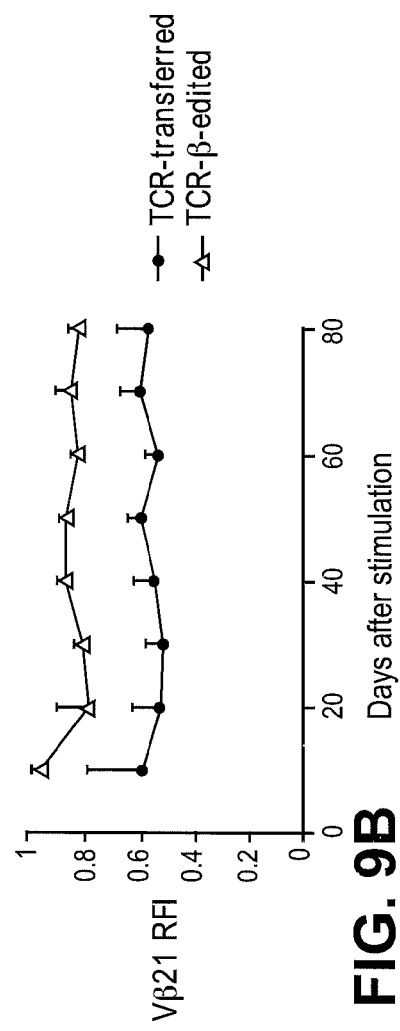
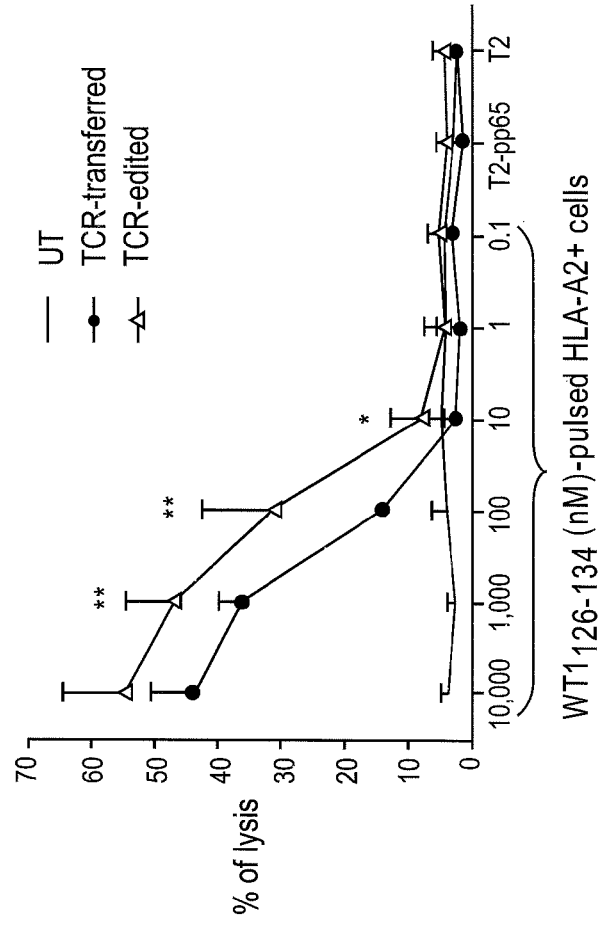
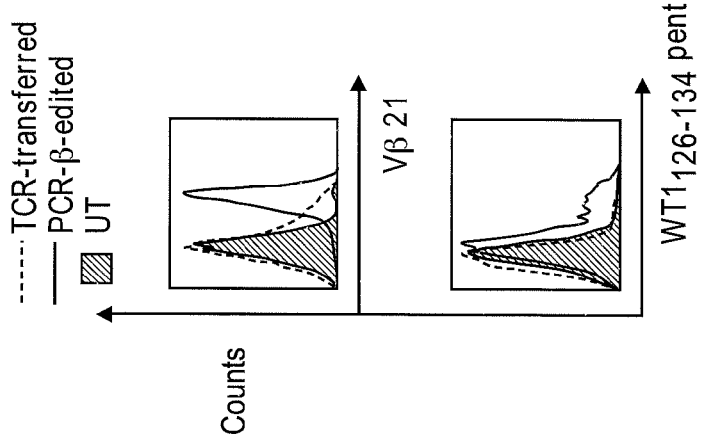
FIG. 9A
FIG. 9B
FIG. 9C

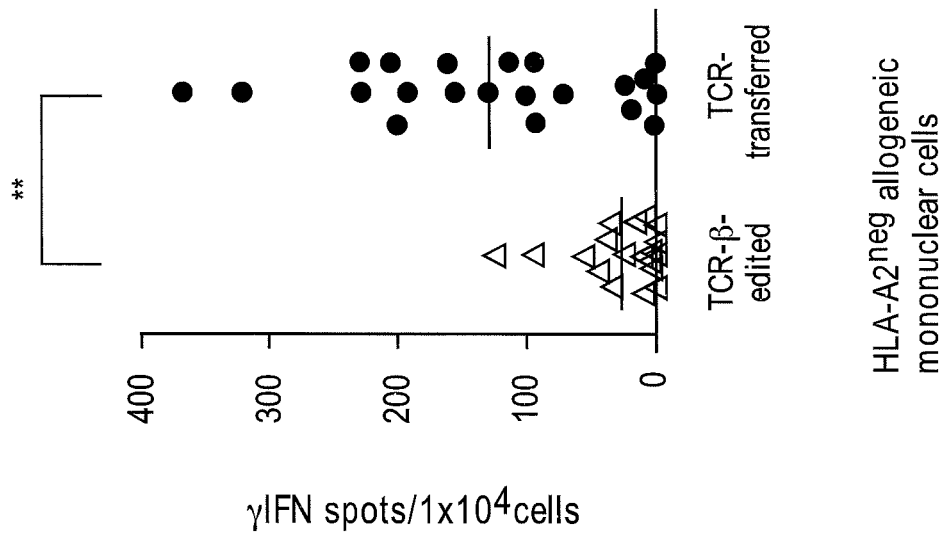
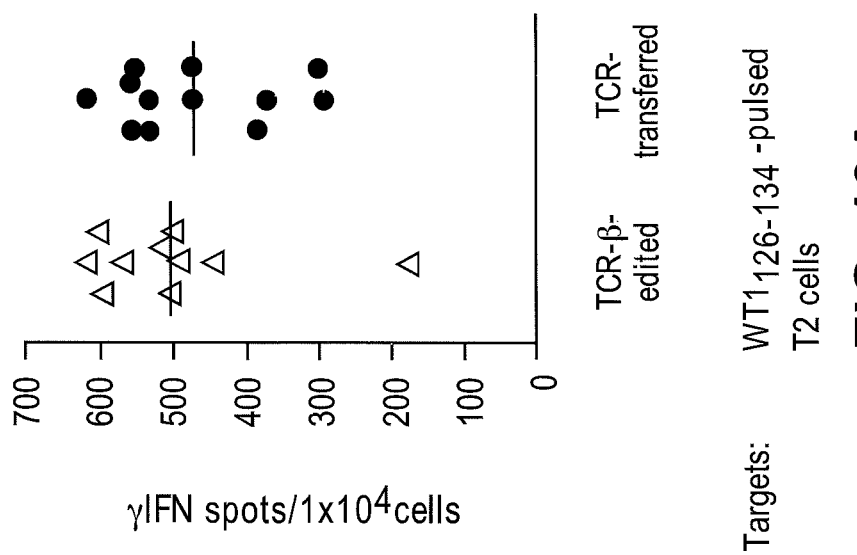
FIG. 10A
FIG. 10B

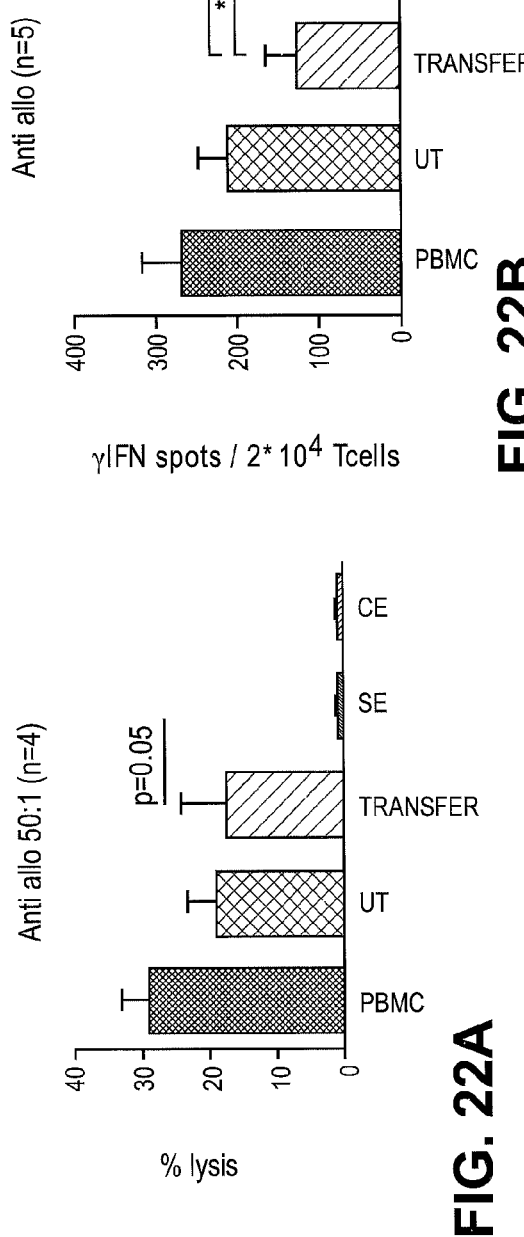
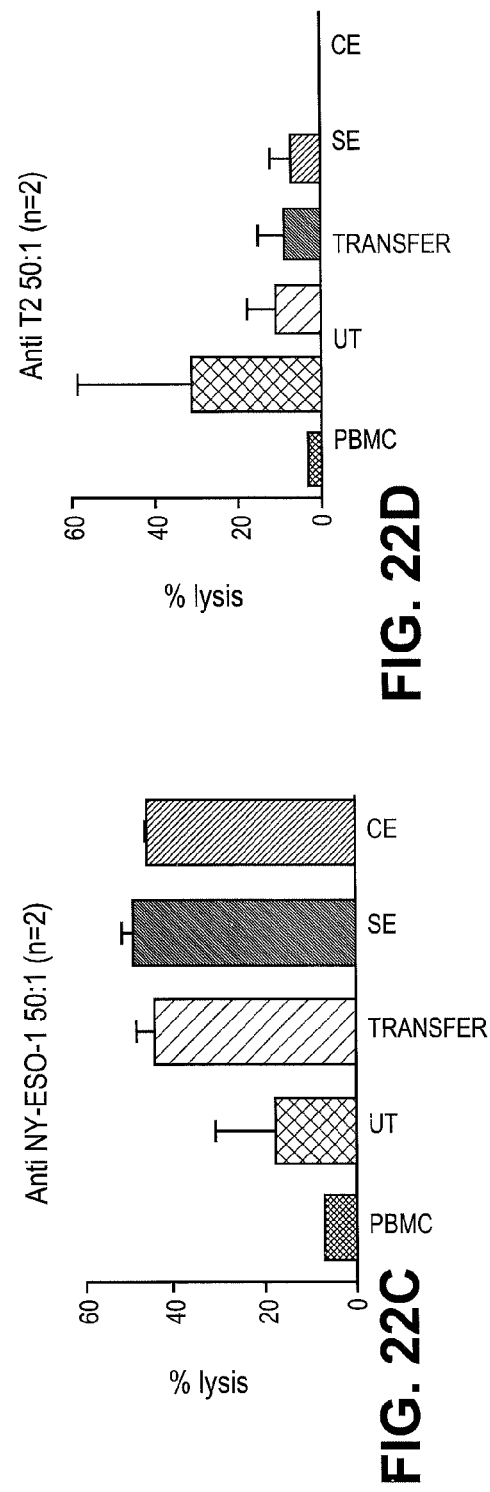
FIG. 22A
FIG. 22B
FIG. 22C
FIG. 22D

US 9,937,207 B2

TARGETED DISRUPTION OF T CELL RECEPTOR GENES USING TALENS

CROSS-REFERENCE TO RELATED APPLICATIONS

The present application claims the benefit of U.S. Provisional Application No. 61/804,076, filed Mar. 21, 2013, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Apr. 29, 2014, is named 8325-0105_SL.txt and is 33,784 bytes in size.

TECHNICAL FIELD

The present disclosure is in the field of genome modification of human cells, including lymphocytes and stem cells.

BACKGROUND

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20050064474; 20060063231; 201000218264; 20120017290; 20110265198; 20130137104; 20130122591; 20130177983; 20130177960 and 20150056705,the disclosures of which are incorporated by reference in their entireties for all purposes. These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage.

The T cell receptor (TCR) is an essential part of the selective activation of T cells. Bearing some resemblance to an antibody, the TCR is typically made from two chains, α and β, which co-assemble to form a heterodimer. The antibody resemblance lies in the manner in which a single gene encoding a TCR chain is put together. TCR chains are composed of two regions, a C-terminal constant region and an N-terminal variable region. The genomic loci that encode the TCR chains resemble antibody encoding loci in that the TCR α gene comprises V and J segments, while the β chain locus comprises D segments in addition to V and J segments. During T cell development, the various segments recombine such that each T cell has a unique TCR structure, and the body has a large repertoire of T cells which, due to their unique TCR structures, are capable of interacting with unique antigens displayed by antigen presenting cells. Additionally, the TCR complex makes up part of the CD3 antigen complex on T cells.

During T cell activation, the TCR interacts with antigens displayed as peptides on the major histocompatability complex (MHC) of an antigen presenting cell. Recognition of the antigen-MHC complex by the TCR leads to T cell stimulation, which in turn leads to differentiation of both T helper cells (CD4+) and cytotoxic T lymphocytes (CD8+) in memory and effector lymphocytes. These cells then can expand in a clonal manner to give an activated subpopulation within the whole T cell population capable of reacting to one particular antigen.

Cytotoxic T lymphocytes (CTLs) are thought to be essential in killing tumor cells. These cells typically are able to induce apoptosis in cancer cells when the cancer cell displays some antigen on its surface that was previously displayed on the MHC by an antigen presenting cell. Normally, following action against target cells, CTLs will apoptose when the cellular threat is cleared, with a subset of lymphocytes remaining that will further differentiate into memory T cells to persist in case the body is exposed to the antigen again. The pool of memory lymphocytes is possibly highly heterogeneous. Recently, two types of memory T-cells have been identified: effector memory T-cells (CD45RA− CCR7−, CD62L−) and central memory T-cells that are CD45RA negative cells characterized by the expression of CCR7 and CD62L, two molecules required for homing in T-cell areas of secondary lymphoid organs. Upon antigenic stimulation, central memory T-cells produce low levels of effector cytokines such as IL-4 and IFN-γ, but high levels of IL-2, which is able to sustain their rapid and consistent proliferation. Upon antigen encounter central memory T-cells undergo: 1) proliferation, resulting in an auto-regenerative process, aimed at increasing their pool, and 2) differentiation, resulting in the generation of effector memory T-cells, which are characterized by a low proliferative potential but are able to migrate to inflamed non-lymphoid tissues and mediate the effector phase of the immune response. Protocols enabling gene transfer into T lymphocytes, while preserving their central memory functional phenotype have been developed (see European Patent Publication No EP1956080, Kaneko et al., 2009 *Blood* 113(5):1006-15).

However, some tumor cells are able to escape surveillance by the immune system, perhaps through mechanisms such as poor clonal expansion of certain CTL subsets expressing the relevant TCR, and localized immune suppression by cancer cells (see Boon et al, (2006) *Annu Rev Immunol.* 24:175-208). The notion of a cancer vaccine is built upon the idea of using these cancer specific antigens to stimulate and expand the CTLs that express the appropriate TCR in vivo, in an attempt to overcome immune escape, however, these cancer vaccines have yet to show any marked success. In fact, an analysis done in 2004 examined 765 metastatic cancer patients that had been treated in over 35 different cancer vaccine trials, where an overall response was observed in only 3.8% of patients (see Rosenberg et at (2004) *Nat. Med.* 10(9): 909-915).

Adoptive immunotherapy is the practice of achieving highly specific T cell stimulation of a certain subpopulation of CTLs that possess a high-avidity TCR to the tumor antigen, stimulating and expanding them ex vivo, and then introducing them into the patient. Adoptive immunotherapy is particularly effective if native lymphocytes are removed from the patient before the infusion of tumor-specific cells. The idea behind this type of therapy is that if the introduced high-avidity CTLs are successful, once the tumor has been cleared, some of these cells will remain as memory T cells and will persist in the patient in case the cancer reappears. In 2002, a study was completed demonstrating regression of metastatic melanoma in patients that were treated under a regime of adoptive immunotherapy following immunodepletion with cyclophosphamide and fludarabine (Dudley et al, (2002) *Science,* 298(5594): 850-854). Response rate was even higher if adoptive immunotherapy was preceded by total body irradiation (Dudley et al 2008 *J Clin Oncol.* 26(32):5233-9).

However, adoptive immunotherapy cannot be performed when the T cells of interest containing high avidity TCRs cannot be readily expanded. In addition, it is often difficult to identify and isolate T cells with therapeutic value from cancer patients because tumor antigens are often self-antigens, against which the patient's immune system is made tolerant through mechanisms of deletion or anergy of those T cell clones with the highest avidity. Thus, transfer of genes encoding high avidity TCRs into patient derived T cells has been proposed and demonstrated (see Rubenstein et al, (2003) *J of Immunology* 170: 1209-1217). More recently, using a mouse model of malignant melanoma, a statistically significant decrease in tumor mass was found following introduction of normal lymphocytes that had been transduced with retroviral vectors carrying human TCR genes specific for the gp-100 melanoma antigen (Abad et al, (2008) *J Immunother.* 31(1): 1-6). TCR gene therapy is also described in Morgan et al. (2006) *Science* 314(5796):126-9 and Burns et al, 2009 *Blood* 114(14):2888-99.

However, transfer of any TCR transgenes into host T cells carries with it the caveats associated with most gene transfer methods, namely, unregulated and unpredictable insertion of the TCR transgene expression cassette into the genome, often at a low level. Such poorly controlled insertion of the desired transgene can result in effects of the transgene on surrounding genes as well as silencing of the transgene due to effects from the neighboring genes. In addition, the endogenous TCR genes that are co-expressed in the T cell engineered with the introduced TCR transgene could cause undesired stimulation of the T cell by the antigen recognized by the endogenous TCR, undesired stimulation of the T cell by unintended antigens due to the mispairing of the TCR transgene with the endogenous TCR subunits creating a novel TCR complex with novel recognition properties, or can lead to suboptimal stimulation against the antigen of interest by the creation of inactive TCRs due to heterodimerization of the transgene encoded TCR subunits with the endogenous TCR proteins. In fact, the risk of severe autoimmune toxicity resulting from the formation of self-reactive TCR from mispairing of endogenous and exogenous chains has been recently highlighted in a murine model (Bendle et al., (2010) Nature Medicine 16:565-570) and in human cells (van Loenen et al., (2010) *Proc Natl Acad Sci USA* 107:10972-7). Additionally, the tumor-specific TCR may be expressed at suboptimal levels on the cell surface, due to competition with the endogenous and mispaired TCR for the CD3 molecules, required to express the complex on the cell surface. Low TCR expression affects the avidity and efficacy of the transgenic T cell.

Wilms tumor antigen (WT1 antigen) is a transcription factor normally expressed in embryonic cells. After birth, its expression is limited to only a few cell types including hematopoietic stem cells. However, it has been found to be overexpressed in many types of leukemias and solid tumors (see Inoue et at (1997) *Blood* 89: 1405-1412) and may contribute to a lack of growth control in these cells. Due to the low expression of WT1 in normal tissues, its expression on cancer cells makes it an attractive target for T-cell mediated therapy. TCR variants with increased avidity to WT1 containing a modified cysteine to discourage mispairing between the endogenous TCR subunits and the transgene TCRs have been transduced into primary T cells and tested for functionality (Kuball et at (2007) *Blood* 109(6):2331-8). The data demonstrated that while T cells that had been freshly transduced with the WT1-TCR variants had an increased antigen response as compared to those transduced with a wildtype TCR domain, after several rounds of stimulation with the WT1 antigen, this improved antigen responsiveness was lost (see Thomas et at (2007) *J of Immunol* 179 (9): 5803-5810). It was concluded that even with the transgene-specific cysteine modification, mispairing with the endogenous TCR peptides may play a role in reducing anti-WT1 avidity seen in cells transduced with the WT1-specific TCRs. See, also, U.S. Patent Publication No. 20110158957.

Another tumor antigen is NY-ESO1. It is a member of the so-called 'CT' set of tumor antigens, meaning that it is expressed on cancer cells and in the testis. Originally identified from expression on an esophageal tumor, NY-ESO1 has now been found to be expressed on several tumor types, including bladder, breast, colorectal, gastric, hepatocarcinoma, head and neck, multiple myeloma, melanoma, non-small cell lung cancer, ovarian, pancreatic, prostate, sarcomas and synovial sarcoma (see Gnjatic et at (2006) *Advances in Cancer Research* p. 1), often when those tumors are in advanced stages. Because of its apparent lack of expression on most tissues, NY-ESO1 has been considered for use in a cancer vaccine. Thus, both full length NY-ESO1 protein and peptides derived from the sequence have been and are being used in clinical trials. It appears however that the vaccination method may have limited usefulness, perhaps due to the production of T cells that have limited avidity to the antigen. In addition, many cancer patients harboring NY-ESO1 positive tumors have detectable anti-NY-ESO1 antibodies in their blood, but their tumors are still able to evade the immune response. One potential solution may be the development of high affinity TCRs against the NY-ESO1 antigen. A study carried out using standard TCR transfer of NY-ESO1 specific TCRs made by three different T cell priming techniques into host T cells (see Sommermeyer et at (2012) *Int. J. Cancer* 132: 1360-1367) found that developing a robust TCR for adoptive immunotherapy will require overcoming a number of issues. There are also additional reports of NY-ESO1 specific TCRs that have been produced (see U.S. Pat. No. 8,367,804 and EP2016102B1 for specific examples). A clinical trial has also been carried out where NY-ESO1+ metastatic melanoma or metastatic synovial cell sarcoma patients were treated with autologous lymphocytes harvested from peripheral blood that had been transduced with a NY-ESO1 TCR. Clinical response was seen in 5 of 11 melanoma patients and 4 of 6 synovial cell sarcoma patients (Robbins et al, (2011) *J. Clin Oncol* 29(7): 917).

Thus, there remains a need for compositions that can introduce desired TCR transgenes into a known chromosomal locus. In addition, there is a need for methods and compositions that can selectively knock out endogenous TCR genes.

SUMMARY

Disclosed herein are compositions and methods for partial or complete inactivation or disruption of an endogenous TCR gene and compositions and methods for introducing and expressing to desired levels of exogenous TCR transgenes into T-lymphocytes, after or simultaneously with the disruption of the endogenous TCR gene.

In one aspect, provided herein are zinc finger nucleases (ZFNs), TALENs or a CRISPR/Cas system with an engineered single guide RNA that cleaves a TCR gene. In certain embodiments, the ZFNs, TALENs or CRIPSR/Cas nucleases bind to target sites in a human TCR α gene and/or target sites in a human TCR β gene. In some embodiments, cleavage within the TCR gene(s) with these nucleases results in permanent disruption (e.g., mutation/inactivation) of the TCR α and/or β gene(s).

In certain embodiments, the nuclease comprises a zinc finger protein. The zinc finger proteins may include 1, 2, 3, 4, 5, 6 or more zinc fingers, each zinc finger having a recognition helix that binds to a target subsite in the target gene. In certain embodiments, the zinc finger proteins comprise 4 or 5 or 6 fingers (designated F1, F2, F3, F4, F5 and F6 and ordered F1 to F4 or F5 or F6 from N-terminus to C-terminus) and the fingers comprise the amino acid sequence of the recognition regions shown in Table 4 and Table 5 and/or recognize the target sites shown in Tables 4 and 5. In other embodiments, the nucleases are TALENs that may comprise engineered repeat units with canonical or non-canonical repeat variable diresidues (RVDs), for example TRAC and TRBC-specific TALENs as shown in Table 14 operably linked to a nuclease domain (e.g., Type IIS Restriction endonuclease and/or meganuclease). The TALENs include a C-cap sequence, for example a C-terminal region that is less full-length of a wild-type TAL C-terminal sequence (e.g., a +17 or +63 C-cap). C-cap sequences are described in U.S. Pat. No. 8,586,526. Additional embodiments comprise use of the CRIPSR/Cas nuclease system where a single guide RNA has been made to target the nuclease to the target site in the TCR α and/or TCR β sequence.

Any of the nucleases described herein may further comprise a cleavage domain and/or a cleavage half-domain (e.g., a wild-type or engineered FokI cleavage half-domain or meganuclease domain with cleavage activity). Thus, in any of the nucleases described herein, the nuclease domain may comprise a wild-type nuclease domain or nuclease half-domain (e.g., a FokI cleavage half domain). In other embodiments, the nucleases (e.g., ZFNs and/or TALENs) comprise engineered nuclease domains or half-domains, for example engineered FokI cleavage half domains that form obligate heterodimers. See, e.g., U.S. Pat. Nos. 7,914,796; 8,034,598 and U.S. Patent Publication No. 20080131962.

In another aspect, the disclosure provides a polynucleotide encoding any of the nucleases described herein. Any of the polynucleotides described herein may also comprise exogenous sequences (donor or patch sequences) for targeted insertion into the TCR α and/or the TCR β gene. In certain embodiments, the donor sequence comprises tumor antigen specific TCR transgene wherein the TCR transgene is a TCR α transgene, a TCR β transgene and combinations thereof. In certain embodiments, the transgene comprises a NY-ESO1-specific transgene where the NY-ESO1-specific transgene is a TCR α transgene, a TCR β transgene and combinations thereof.

In yet another aspect, a gene delivery vector comprising one or more of the polynucleotides described herein is provided (e.g., donor and/or nuclease(s)). In certain embodiments, the vector is an adenoviral vector (e.g., an Ad5/F35 vector) or a lentiviral vector (LV) including integration competent or integration-defective lentiviral vectors. Thus, also provided herein are adenoviral (Ad) vectors or LVs comprising a sequence encoding at least one zinc finger nuclease (ZFN), TALEN or CRISPR/Cas nucleases and single guide RNA and/or a donor sequence for targeted integration into a target gene. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments the vector is pseudo-typed with a VSV-G envelope, or with other envelopes. In additional embodiments, the target gene is the human TCR α gene. In certain embodiments, the target gene is the human TCR β gene. The vectors described herein may also comprise donor sequences. In additional embodiments, the donor sequences comprise human TCR genes that are specific for an MHC/antigen complex of interest. In some embodiments, the donor sequences may comprise the human TCR α and/or the human TCR β genes that are specific for an MHC/antigen complex of interest. In certain embodiments, a single vector comprises sequences encoding one or more ZFNs, TALENs or CRISPR/Cas nuclease complex and the donor sequence(s). In other embodiments, the donor sequence(s) are contained in a first vector and the ZFN-, TALEN- or CRISPR/Cas encoding sequences are present in a second vector. In further embodiments, the ZFN-, TALEN-, or CRISPR/Cas-encoding sequences are present in a first vector and the TCR α gene of interest is present in a second vector and the TCR β gene of interest is present in a third vector. In some embodiments, the TCR genes of interest are inserted into the location of the endogenous TCR genes, and in other embodiments the TCR genes of interest are inserted into randomly selected loci, or into a separate locus after genome-wide delivery. In some embodiments, the separate locus for TCR transgene insertion is the PPP1R12C locus (also known as AAVS1, see U.S. Pat. No. 8,110,379). In other embodiments, the TCR transgene is inserted into a CCR-5 locus. See, U.S. Pat. No. 7,951,925.

In yet another aspect, the disclosure provides an isolated T-lymphocyte comprising an exogenous sequence stably integrated into the genome of the T-lymphocyte and in which an endogenous TCR gene is partially or completely inactivated by a zinc finger nuclease or C-cap TALEN (TALEN with a C-terminal truncation). In certain embodiments, the cell comprises any of the proteins, polynucleotides and/or vectors described herein. In certain embodiments, the cell is selected from the group consisting of a stem/progenitor cell, a T-cell (e.g., CD4$^+$ T-cell). In a still further aspect, the disclosure provides a cell or cell line which is descended from a cell or line as described herein, namely a cell or cell line descended (e.g., in culture) from a cell in which TCR has been inactivated by one or more ZFNs, TALENs or specific CRISPR/Cas nucleases and/or in which a TCR-encoding donor polynucleotide has been stably integrated into the genome of the cell. Thus, descendants of cells as described herein may not themselves comprise the proteins, polynucleotides and/or vectors described herein, but, in these cells, a TCR gene is inactivated and/or a TCR-encoding donor polynucleotide is integrated into the genome and/or expressed.

In another aspect, described herein are methods of inactivating a TCR gene in a cell by introducing one or more proteins, polynucleotides and/or vectors into the cell as described herein. In any of the methods described herein the ZFNs, TALENs or specific CRISPR/Cas nucleases may induce targeted mutagenesis, targeted deletions of cellular DNA sequences, and/or facilitate targeted recombination at a predetermined chromosomal locus. Thus, in certain embodiments, the ZFNs, TALENs or specific CRISPR/Cas nucleases delete or insert one or more nucleotides of the target gene. In some embodiments the TCR gene is inactivated by ZFN, TALEN or specific CRISPR/Cas nuclease cleavage followed by non-homologous end joining. In other embodiments, a genomic sequence in the target gene is replaced, for example using a ZFN, TALES or specific CRISPR/Cas nuclease (or vector encoding said ZFN, TALEN or specific CRISPR/Cas nuclease) as described herein and a "donor" sequence that is inserted into the gene following targeted cleavage with the ZFN, TALEN or specific CRISPR/Cas nuclease. In certain embodiments, the donor sequence comprises a NY-ESO1 sequence. The donor sequence may be present in the ZFN, TALEN or specific CRISPR/Cas nuclease vector, present in a separate vector (e.g., Ad or LV vector) or, alternatively, may be introduced into the cell using a different nucleic acid delivery mechanism.

In another aspect, methods of using the zinc finger proteins, TALENs or specific CRISPR/Cas nucleases and fusions thereof for mutating a TCR gene and/or inactivating TCR function in a cell or cell line are provided. Thus, a method for inactivating a TCR gene in a human cell is provided, the method comprising administering to the cell any of the proteins or polynucleotides described herein.

In yet another aspect, the disclosure provides a method for treating or preventing cancer, infections, autoimmune disorders, and/or graft-versus-host disease (GVHD) in a subject, the method comprising: (a) introducing, into a cell (e.g., lymphocyte, stem cell, progenitor cell, etc.), a first nucleic acid encoding a first polypeptide, wherein the first polypeptide comprises: (i) a zinc finger or TALE DNA-binding domain that is engineered to bind to a first target site in a TCR gene; and (ii) a cleavage domain; under conditions such that the polypeptide is expressed in the cell, whereby the polypeptide binds to the target site and cleaves the endogenous TCR gene; and (b) introducing, into the cell, a second nucleic acid encoding a second polypeptide, wherein the second polypeptide comprises: (i) a zinc finger or TALE DNA-binding domain that is engineered to bind to a second target site in a TCR gene; and (ii) a cleavage domain; under conditions such that the polypeptide is expressed in the cell, whereby the polypeptide binds to the target site and cleaves the endogenous TCR gene; and (c) introducing into the cell a third nucleic acid comprising a nucleic acid encoding a TCR gene or TCR genes, specific for a tumor specific antigen in an MHC complex, such that the third nucleic acid is introduced into the endogenous TCR gene and the cell with the introduced third nucleic acid treats or prevents cancer, infections, autoimmune disorders, and/or graft-versus-host disease (GVHD) in the subject. In certain embodiments, steps (a)-(c) are performed ex vivo and the method further comprises, following step (c), the step of introducing the cell into the subject. In certain embodiments, the third nucleic acid encoding the TCR gene(s) is expressed under the control of bi-directional promoters (e.g., PGK, EF1α, etc.). In other embodiments, the TCR gene(s) are expressed from bicistronic cassettes (e.g., using viral 2A peptides or an IRES sequence) or by multiple LVs expressing different TCR genes under monodirectional promoters. In certain embodiments, the cell is selected from the group consisting of a stem/progenitor cell, or a T-cell. In any of the methods describes herein, the first nucleic acid may further encode a second polypeptide, wherein the second polypeptide comprises: (i) a zinc finger or TALE DNA-binding domain that is engineered to bind to a second target site in the TCR gene; and (ii) a cleavage domain; such that the second polypeptide is expressed in the cell, whereby the first and second polypeptides bind to their respective target sites and cleave the TCR gene.

In another aspect, the disclosure also provides a method for treating or preventing cancer in a subject, the method comprising: (a) introducing, into a cell, a first nucleic acid encoding a first polypeptide, wherein the first polypeptide comprises: (i) a zinc finger or TALE DNA-binding domain that is engineered to bind to a first target site in a TCR gene; and (ii) a cleavage domain; under conditions such that the polypeptide is expressed in the cell, whereby the polypeptide binds to the target site and cleaves the endogenous TCR; and (b) introducing, into a cell, a second nucleic acid encoding a second polypeptide, wherein the second polypeptide comprises: (i) a zinc finger or TALE DNA-binding domain that is engineered to bind to a first target site in a safe harbor locus (e.g., PPP1R12C, CCR5); and (ii) a cleavage domain; under conditions such that the polypeptide is expressed in the cell, whereby the polypeptide binds to the target site and cleaves in the safe harbor locus (e.g., PPP1R12C, CCR5) and (c) introducing into the cell a third nucleic acid comprising a donor nucleic acid encoding a TCR gene or TCR genes specific for a tumor specific antigen in an MHC complex; and (d) introducing the cell into the subject. The nucleic acids comprising the TCR specific ZFN, TALEN or CRISPR/Cas nuclease system may be introduced simultaneously with the ZFN, TALEN or CRISPR/Cas nuclease system specific for the safe-harbor locus and the donor nucleic acid molecule, or the nucleic acid encoding the TCR-specific ZFN, TALEN or CRISPR/Cas nuclease system may be introduced into the cell in a first step, and then the safe harbor locus (e.g., PPP1R12C, CCR5)-specific ZFNs, TALENs or CRISPR/Cas nuclease system and the donor nucleic acid molecule may be introduced in a second step. In certain embodiments, the donor nucleic acid molecule encodes a tumor antigen such as NY-ESO1.

The disclosure also provides a method of preventing or treating a cancer in a subject comprising introducing, into a subject, a viral delivery particle wherein the viral delivery particle comprises (a) a first nucleic acid encoding a first polypeptide, wherein the first polypeptide comprises: (i) a zinc finger or TALE DNA-binding domain that is engineered to bind to a first target site in a TCR gene; and (ii) a cleavage domain; under conditions such that the polypeptide is expressed in the cell, whereby the polypeptide binds to the target site and cleaves the endogenous TCR; and (b) a second nucleic acid encoding a second polypeptide, wherein the second polypeptide comprises: (i) a zinc finger or TALE DNA-binding domain that is engineered to bind to a first target site in a safe harbor locus (e.g., AAVS1, CCR5, albumin, HPRT etc. (see co-owned U.S. Pat. Nos. 8,110,379 and 7,951,925, and Patent Publication Nos. 20130177983 and 20130137104); and (ii) a cleavage domain; under conditions such that the polypeptide is expressed in the cell, whereby the polypeptide binds to the target site and cleaves the safe harbor locus (e.g., AAVS1, CCR5, albumin, HPRT); and (c) a third nucleic acid encoding a third polypeptide, wherein the third polypeptide comprises: (i) a zinc finger or TALE DNA-binding domain that is engineered to bind to a second target site in a safe harbor locus (e.g., AAVS1, CCR5, albumin, HPRT); and (ii) a cleavage domain; under conditions such that the polypeptide is expressed in the cell, whereby the polypeptide binds to the target site and cleaves at the safe harbor locus (e.g., AAVS1, CCR5, albumin, HPRT); and (d) a third nucleic acid comprising a donor nucleic acid encoding a TCR gene or TCR genes specific for a tumor specific antigen in an MHC complex; such that the endogenous TCR gene is cleaved and rendered inactive, and the safe harbor gene (e.g., AAVS1, CCR5, albumin, HPRT) is cleaved and the TCR gene specific for a tumor specific antigen in an MHC complex becomes inserted into the endogenous TCR gene. In certain embodiments, the method further comprises, following step (d), the step of introducing the cell into the subject. In certain embodiments, the donor nucleic acid molecule encodes a tumor antigen such as NY-ESO1.

In any of the methods described herein, a viral delivery particle can be used to deliver one or more of the polynucleotides (ZFN- or TALEN-encoding and/or donor polynucleotides). Furthermore, in any of the methods and compositions described herein, the cell can be, for example, a stem/progenitor cell (e.g., a $CD34^+$ cell), or a T-cell (e.g., a $CD4^+$ cell).

Furthermore, any of the methods described herein can be practiced in vitro, in vivo and/or ex vivo. In certain embodiments, the methods are practiced ex vivo, for example to modify PBMCs, e.g., T-cells, to make them specific for a tumor antigen/MHC complex of interest to treat a tumor in a subject. Non-limiting examples of cancers that can be treated and/or prevented include lung carcinomas, pancreatic cancers, liver cancers, bone cancers, breast cancers, colorectal cancers, leukemias, ovarian cancers, lymphomas, brain cancers and the like.

BRIEF DESCRIPTION OF THE DRAWINGS

FIG. 1, panels A and B, depict construction and expression of a Wilms tumor antigen (WT1) specific lentiviral vector.

FIG. 2, panels A to C, are graphs depicting results of cells transduced with TCR constructs. FIG. 2A depicts induction of γIFN production by stimulation of the cells with WT1+ HLA-A2+ and WT1+/HLAA2− cells (the indicated primary AML or K562 cells (right most bar in graph)) transduced with vectors expressing the transgenic TCRs either from the PGK/mCMV dual promoter combination (left side group of 4 bars) or the EF1α/mCMV dual promoter (right side group of 4 bars) following exposure to WT1+HLA-A2+ or WT1+ HLA-A2− (negative control) primary leukemic blasts from AML patients (designated as AML1 (left most bar), AML2 (second bar from the left) and AML3 (third bar from the left)). FIGS. 2B and 2C demonstrate the percent killing of the leukemic blasts from AML1 and AML2 (solid lines, closed circles) by the TCR modified cells. Dotted lines represent residual killing of the leukemic blasts by the TCR modified cells in the presence of an excess of cold (not labeled) HLA-A2 target cells, loaded with the WT1 proper peptide.

FIG. 3, panels A and B, are graphs depicting GFP expression following introduction of ZFNs targeted to a safe harbor locus together with a GFP donor.

FIG. 4, panels A and B, depict diagrams of exemplary TCR-α and TCR-β donor molecules (FIG. 4A) and the TCR-β genes (FIG. 4B).

FIG. 6A depicts the results from a Cel-I assay on cells where the ZFNs were targeted to Exon 1. FIG. 6B depicts the results of a Cel I mismatch assay where the ZFNs were targeted to Exon 3. "GFP" indicates cells transduced with GFP only vectors. Percent alteration (NHEJ) is indicated at the bottom of the lanes. As shown, sorted CD3− lymphocytes survive in the presence of IL7 and IL15.

FIG. 7, panels A to F, depict ZFN-mediated cleavage of TCR-β. Untransduced and transduced Jurkat cells using the TCR-β specific ZFN pair 16783 and 16787 at two concentrations of vector demonstrated the loss of CD3 signal at the cell surface (from 2.7% CD3(−) to 20.2% CD3(−) (see Example 6). FIG. 7E is a graph depicting percent CD3− cells and demonstrates the persistence of CD3− cells over time (percent of CD3− cells stays fairly constant even up to 45 days) in cells treated with increasing concentrations of ZFNs. FIG. 7F is a graph depicting that CD3− cells have lost TCR/CD3 functionality since they do not appear to divide in response to non-specific mitogens. As shown, CD3− cells survive and are stable in culture in the presence of IL7 and IL15 for more than 40 days, do not respond to polyclonal mitogens, and maintain a TCM phenotype.

FIG. 9, panels A to C, depict expression of Vβ21 TCR. FIG. 9A depicts Vβ21 TCR expression (upper histogram) and $WT1_{126-434}$ pentamer binding (lower histogram) in $CD8^+$ TCR β chain disrupted and WT1 transduced cells (TCR-β-edited), unedited WT1 LV transduced cells (TCR-transferred), and untransduced lymphocytes treated with the same culture conditions. FIG. 9B shows a time course of surface expression of Vβ21 TCR. Average+SD (n=2) of Vβ21 RFI is represented. RFI is calculated from the ratio of the MFI of Vβ21 measured in $CD8^+$ TCR-edited (open triangle) or TCR-transferred (dark circle) lymphocytes/the MFI of Vβ21 measured in $CD8^+$ T cells naturally expressing Vβ21. FIG. 9C depicts the results of a cytotoxicity assay with TCR-edited and TCR-transferred cells. Functional activity is measured by a $^{51}$Chromium release assay for lysis of labeled T2 cells pulsed with increasing concentrations of the $WT1_{126-134}$ HLA-A2 restricted peptide, or with the irrelevant CMV-derived $pp65_{495-503}$ HLA-A2 restricted peptide (10 μM) as negative control, at an Effector/Target (E/T) ratio of 12. Results are represented as average+SD of % of lysis (**, p<0.01, *, p<0.05 with Mann-Whitney test, TCR-edited n=6, TCR-transferred n=4).

FIG. 10, panels A and B, depict the functional activity of WT1 TCR-positive T cell clones as tested by γIFN ELISpot assay. Clones were exposed to T2 cells pulsed with 10 nM of the $WT1_{126-134}$ HLA-A2 restricted peptide (10A), or to allogeneic PBMC (10B) at a stimulator/responder ratio of 1:1. The number of specific spots (open triangles and dark circles) observed is shown on the y axis as number of spots produced in presence of stimulators minus the number of spots produced by effectors alone. The results show that the TCR-β edited clones exhibit a higher degree of antigen specificity than the TCR transferred cells which contain both the endogenous and the exogenous TCR genes.

FIG. 12, panels A to C, depict CD3 expression in primary lymphocytes treated with ZFN targeting TCR α genes. FIG. 12A discloses the protein sequence as SEQ ID NO: 109 and the DNA sequence as SEQ ID NO: 108.

FIG. 13 depicts partial sequence of the genomic TRAC ZFN target site in ZFN-treated human lymphocytes was amplified, cloned and sequenced to confirm ZFN-induced modification. Sequence alignment revealed several ZFN-induced deletions and insertions (indels) within the target region. The left column indicates the number of clones retrieved while the right column indicates the number of deleted or inserted nucleotides. FIG. 13 discloses SEQ ID NOs: 110-143, respectively, in order of appearance.

FIG. 19, panels A to C, demonstrate expression of the NY-ESO1-specific TCR and binding to the appropriate target.

FIG. 20, panels A to D, depict binding and activity of the T cell populations described in FIG. 19. FIG. 20A depicts the binding of the different T cell groups against a peptide derived from the NY-ESO1 target, while

FIG. 21, panels A and B, depict growth inhibition of cells in a co-culture experiment by the different T cell populations.

FIG. 22, panels A to D, are graphs depicting the alloreactivity of NY-ESO1 T-cells. FIG. 22A shows the percent of cell lysis in the indicated cell types at the effector/target ratio of 50:1. FIG. 22B shows results of an γ-interferon (γ-IFN) ELISPOT assay in the indicated cells. FIG. 22C shows the percent cell lysis in the indicated cells pulsed with the NY-ESO-1 specific peptide while FIG. 22D shows the lysis detected when the cells are not pulsed.

FIG. 24, panels A to C, depict TCR editing by ZFN-encoding mRNA electroporation.

FIG. 25, panels A to D, depict double TCR editing by ZFN mRNA electroporation.

DETAILED DESCRIPTION

Figure 1A:
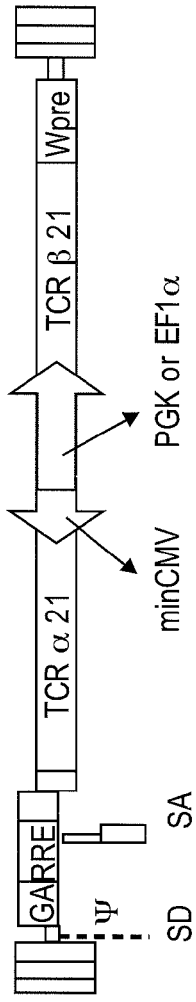
FIG. 1A depicts a diagram of the genes encoding a codon-optimized, cysteine-modified TCR specific for an HLA-A2-restricted peptide from the Wilms tumor antigen 1 (WT1) cloned into a third generation lentiviral vector (LV) under the control of a bi-directional PGK or EF1α promoter. See, Amendola et at (2005) Nature Biotechnology 23(1): 108-116 and U.S. Patent Publication No US2006200869.

Disclosed herein are zinc finger nucleases (ZFNs) and TALENs targeting a TCR gene (TCR-ZFNs and TCR-TALENs). These nucleases efficiently generate a double strand break (DSB), for example at a predetermined site in a TCR coding region. ZFN- or TALEN-mediated introduction of a site-specific double strand break (DSB) in genes that encode for the TCR gene can result in the specific and permanent disruption of the endogenous TCR complex in human cells, including human T cells. These cells can be selected from a pool by selecting for CD3(−) cells, and culturing them on IL7 and IL15. In addition, disclosed herein are methods and compositions for the replacement of the endogenous TCR genes with TCR transgenes of one's choice, either via random integration or by site directed targeted integration.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. TALENs preferably include C-terminal and/or N-terminal truncations (e.g., C-cap and/or N-cap). See, e.g., U.S. Pat. No. 8,586,526, incorporated by reference herein in its entirety.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526; 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs can be found at the following internet address: http://www.ncbi.nlm.gov/cgi-bin/BLAST. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598; 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value there between or there above), preferably between about 100 and 1,000 nucleotides in length (or any integer there between), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

A "safe harbor locus" is a location within a genome that can be used for integrating exogenous nucleic acids. The addition of exogenous nucleic acids into these safe harbor loci does not cause any significant effect on the growth of the host cell by the addition of the DNA alone. Non-limiting examples of safe harbor genes include, for example, a CCR5 gene, a CXCR4 gene, a PPP1R12C (also known as AAVS1) gene, an albumin gene or a Rosa gene. See, e.g., U.S. Pat. Nos. 7,951,925 and 8,110,379; U.S. Publication Nos. 201000218264; 20100291048; 20120017290; 20110265198; 20130137104; 20130122591; 20130177983 and 20130177960.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Modulation may also be complete, i.e., wherein gene expression is totally inactivated or is activated to wild-type levels or beyond; or it may be partial, wherein gene expression is partially reduced, or partially activated to some fraction of wildtype levels.

"Eucaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain (ZFP, TALE) is fused to a cleavage domain (e.g., endonuclease domain such as FokI, meganuclease domain, etc.), the DNA-binding domain and the cleavage domain are in operative linkage if, in the fusion polypeptide, the DNA-binding domain portion is able to bind its target site and/or its binding site, while the cleavage (nuclease) domain is able to cleave DNA in the vicinity of the target site. The nuclease domain may also exhibit DNA-binding capability (e.g., a nuclease fused to a ZFP or TALE domain that also can bind to DNA). Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

Nucleases

Described herein are nucleases (e.g., ZFNs or TALE nucleases) that can be used for inactivation of a TCR gene The nuclease may be naturally occurring or may be a chimera of a DNA-binding domain and a cleavage domain. It will be apparent that within the chimera, the component DNA-binding and cleavage domains may both be naturally occurring, may both be non-naturally occurring or one may be naturally occurring and the other may be non-naturally occurring.

Thus, any nuclease can be used in the methods disclosed herein. For example, naturally-occurring homing endonucleases and meganucleases have very long recognition sequences, some of which are likely to be present, on a statistical basis, once in a human-sized genome. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66. The DNA-binding domains of the homing endonucleases and meganucleases may be altered in the context of the nuclease as a whole (i.e., such that the nuclease includes the cognate cleavage domain) or may be fused to a heterologous DNA-binding domain (e.g., zinc finger protein or TALE) or to a heterologous cleavage domain. DNA-binding domains derived from meganucleases may also exhibit DNA-binding activity.

In certain embodiments, the nuclease comprises a zinc finger DNA-binding domain and a restriction endonuclease nuclease domain, also referred to as as zinc finger nucleases (ZFNs).

In other embodiments, the nuclease comprises an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises a endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et at (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs).

Thus, any naturally occurring or engineered nuclease having a unique target site can be used in the methods described herein.

A. DNA-Binding Domains

The nucleases described herein typically include a DNA-binding domain and a cleavage domain. Any DNA-binding domain can be used in the practice of the present invention, including but not limited to a zinc finger DNA-binding domain, a TALE DNA binding domain, or a DNA-binding domain from a meganuclease.

In certain embodiments, zinc finger binding domains that are engineered to bind to a sequence of choice are employed. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. Similarly, a TALE DNA-binding domain can be engineered to bind to a sequence of choice. See, e.g., 8,586,526. Engineered zinc finger or TALE DNA binding domains can have a novel binding specificity, compared to a naturally-occurring zinc finger or TALE protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 8,586,526; 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. Enhancement of binding specificity for zinc finger binding domains has been described, for example, in co-owned WO 02/077227.

In other embodiments, the DNA binding domain comprises a TALE DNA binding domain (see, co-owned U.S. Pat. No. 8,586,526, incorporated by reference in its entirety herein). A TALE DNA-binding domain comprises one or more TALE "repeat units." A single "repeat unit" (also referred to as a "repeat") is typically 33-35 amino acids in length, where positions 12 and/or 13 (referred to as hypervariable diresidue region or "RVD") are involved in binding to a DNA nucleotide. An "atypical" RVD is an RVD sequence (positions 12 and 13) that occurs infrequently or never in nature, for example, in less than 5% of naturally occurring TALE proteins, preferably in less than 2% of naturally occurring TALE proteins and even more preferably less than 1% of naturally occurring TALE proteins. An atypical RVD can be non-naturally occurring. The TALE DNA-binding domains preferably include a C-cap sequence and, optionally, an N-cap sequence. The "cap" sequences are preferably a fragment (truncation) of a polypeptide found in full-length TALE proteins, for example any truncation of a C- and/or N-terminal region flanking the TALE repeat domain in a naturally occurring TALE protein. The C-cap may be, for example, truncations as compared to a wild-type C-terminal TALE protein (which is numbered as starting at C−20) including but not limited, C−19, C−18, C−17, C−16, C−15, C−14, C−13, C−12, C−11, C−10, C−9, C−8, C−7, C−6, C−5, C−4, C−3, C−2, C−1, increments to C+1, and then increments to C+2, C+3, etc. towards the C-terminus of the polypeptide (e.g., C+63, which is 83 amino acids in length as it extends from C−20 to C+63).

In addition, as disclosed in these and other references, zinc finger domains and/or multi-fingered zinc finger proteins or TALEs may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

Selection of target sites; ZFPs or TALEs and methods for design and construction of fusion proteins (and polynucleotides encoding same) are known to those of skill in the art and described in detail in U.S. Pat. Nos. 6,140,081; 5,789, 538; 6,453,242; 6,534,261; 5,925,523; 6,007,988; 6,013, 453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496, the disclosures of which are incorporated by reference in their entireties for all purposes.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

In certain embodiments, the DNA binding domain is an engineered zinc finger protein that typically includes at least one zinc finger but can include a plurality of zinc fingers (e.g., 2, 3, 4, 5, 6 or more fingers). Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, wherein these regulatory domains can be transcriptional activation or repression domains.

In other embodiments, the DNA-binding domain comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay et at (2007) *Science* 318:648-651 and U.S. Patent Publication No. 20110239315). These proteins contain a DNA binding domain and a transcriptional activation domain. One of the most well characterized TALEs is AvrBs3 from *Xanthomonas campestgris* pv. *Vesicatoria* (see Bonas et at (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et at (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et at (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. The zinc finger nucleases described herein bind in a TCR gene. Tables 5 and 6 (see Example 4) describe a number of zinc finger binding domains that have been engineered to bind to nucleotide sequences in the human TCR gene. Each row describes a separate zinc finger DNA-binding domain. The DNA target sequence for each domain is shown in the first column (DNA target sites indicated in uppercase letters; non-contacted nucleotides indicated in lowercase), and the second through fifth columns show the amino acid sequence of the recognition region (amino acids −1 through +6, with respect to the start of the helix) of each of the zinc fingers (F1 through F4 or F5 or F6) in the protein. Also provided in the first column is an identification number for each protein.

Also described are TALENs that bind in a TCR gene. Table 14 (see, Example 10) describe TALENs that have been engineered to bind to a nucleotide sequence in a human TCR gene. Each row describes a separate TALE DNA binding protein with the indicated number of RVD-containing domains. The DNA target sequence for each domain is shown in the first column (DNA target sites indicated in uppercase letters; non-contacted nucleotides are in lowercase). Also provided in the first column is an identification number for each protein.

As described below, in certain embodiments, a four- or five-finger binding domain as shown in Tables 5 and 6, or a TALE DNA binding domain as shown in Table 14 is fused to a cleavage half-domain, such as, for example, the cleavage domain of a Type IIs restriction endonuclease such as FokI. A pair of such zinc finger or TALE/nuclease half-domain fusions are used for targeted cleavage, as disclosed, for example, in U.S. Pat. No. 8,586,526 and U.S. Publication No. 20050064474.

For targeted cleavage, the near edges of the binding sites can separated by 5 or more nucleotide pairs, and each of the fusion proteins can bind to an opposite strand of the DNA target.

In addition, domains from these naturally occurring or engineered nucleases can also be isolated and used in various combinations. For example, the DNA-binding domain from a naturally occurring or engineered homing endonucleases or meganuclease can be fused to a heterologous cleavage domain or half domain (e.g., from another homing endonuclease, meganuclease or TypeIIS endonuclease). These fusion proteins can also be used in combination with zinc finger nucleases described above.

The nucleases described herein can be targeted to any sequence in any TCR genomic sequence.

B. Cleavage Domains

The nuclease may comprise heterologous DNA-binding and cleavage domains (e.g., zinc finger nucleases; TALENs, meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site). In certain embodiments, the nuclease is a meganuclease (homing endonuclease). Naturally-occurring meganucleases recognize 15-40 base-pair cleavage sites and are commonly grouped into four families: the LAGLIDADG family ('LAGLIDADG' disclosed as SEQ ID NO: 155), the GIY-YIG family, the His-Cyst box family and the HNH family Exemplary homing endonucleases include I-SceI,I-CeuI,PI-PspI,PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argastet al. (1998) *J. Mol. Biol.* 280:345-353 and the New England Biolabs catalogue.

DNA-binding domains from naturally-occurring meganucleases, primarily from the LAGLIDADG family ('LAGLIDADG' disclosed as SEQ ID NO: 155), have been used to promote site-specific genome modification in plants, yeast, Drosophila, mammalian cells and mice, but this approach has been limited to the modification of either homologous genes that conserve the meganuclease recognition sequence (Monet et al. (1999), *Biochem. Biophysics. Res. Common.* 255: 88-93) or to pre-engineered genomes into which a recognition sequence has been introduced (Route et al. (1994), *Mol. Cell. Biol.* 14: 8096-106; Chilton et al. (2003), *Plant Physiology.* 133: 956-65; Puchtaet al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622). Accordingly, attempts have been made to engineer meganucleases to exhibit novel binding specificity at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62; Chevalier et al. (2002) *Molec. Cell* 10:895-905; Ashworth et al. (2006) *Nature* 441:656-659; Pâques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI).

In other embodiments, the nuclease is a zinc finger nuclease (ZFN). ZFNs comprise a zinc finger protein that has been engineered to bind to a target site in a gene of choice and cleavage domain or a cleavage half-domain.

As noted above, zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in U.S. Pat. No. 6,794,136.

Selection of target sites; ZFNs and methods for design and construction of fusion proteins (and polynucleotides encoding same) are known to those of skill in the art and described in detail in U.S. Pat. Nos. 7,888,121 and 8,409,861, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some embodiments, the nuclease is an engineered TALEN. Methods and compositions for engineering these proteins for robust, site specific interaction with the target sequence of the user's choosing have been published (see U.S. Pat. No. 8,586,526).

Nucleases such as ZFNs, TALENs and/or meganucleases also comprise a nuclease (cleavage domain, cleavage half-domain). As noted above, the cleavage domain may be heterologous to the DNA-binding domain, for example a zinc finger or TALE DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

One or more of these enzymes (or functional fragments thereof) can be used as a source of cleavage domains and cleavage half-domains. Similarly, a cleavage half-domain can be derived from any nuclease or portion thereof, as set forth above, that requires dimerization for cleavage activity.

In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 20070134796, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,888,121; 8,409,861; and U.S. Patent Publication No. 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in certain embodiments, the mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Pat. No. 7,888,121, the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in U.S. Pat. No. 7,888,121.

The engineered cleavage half-domains described herein may be obligate heterodimer mutants in which aberrant cleavage is minimized or abolished. See, e.g., Example 1 of WO 07/139898. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). Engineered cleavage half-domains described herein can be prepared using any suitable method, for example, by site-directed mutagenesis of wild-type cleavage half-domains (Fok I) as described in U.S. Pat.

No. 7,888,121; and U.S. Patent Publication Nos. 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Alternatively, the FokI nuclease domain variant known as "Sharkey" may be used (see Guo et al, (2010) *J. Mol. Biol.* doi:10.1016/j.jmb.2010.04.060).

Nuclease expression constructs can be readily designed using methods known in the art. See, e.g., U.S. Pat. Nos. 7,888,121 and 8,409,861 and U.S. Patent Publication Nos. 20030232410; 20050208489; 20050026157; 20060063231; and 20070134796. In certain embodiments, expression of the nuclease is under the control of an inducible promoter, for example the galactokinase promoter which is activated (de-repressed) in the presence of raffinose and/or galactose and repressed in presence of glucose. In particular, the galactokinase promoter is induced and the nuclease(s) expressed upon successive changes in the carbon source (e.g., from glucose to raffinose to galactose). Other non-limiting examples of inducible promoters include CUP1, MET15, PHO5, and tet-responsive promoters.

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et at (2012) *Science* 337, p. 816-821, Jinek et al, (2013), *eLife* 2:e00471, and David Segal, (2013) *eLife* 2:e00563). Thus, the CRISPR/Cas system can be engineered to create a DSB at a desired target in a genome, and repair of the DSB can be influenced by the use of repair inhibitors to cause an increase in error prone repair.

A. Target Sites

As described in detail above, DNA domains in ZFNs and TALENs can be engineered to bind to any sequence of choice in a locus. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, U.S. Pat. Nos. 8,586,526; 6,453,242 and 6,534,261, incorporated by reference herein in their entireties. Rational design of TAL-effector domains can also be performed. See, e.g., U.S. Pat. No. 8,586,526.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; and WO 01/88197.

Selection of target sites; nucleases and methods for design and construction of fusion proteins (and polynucleotides encoding same) are known to those of skill in the art and described in detail in U.S. Pat. Nos. 7,888,121 and 8,409,861, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Pat. No. 8,586,526.

Additionally, single guide RNAs can be engineered to bind to a target of choice in a genome by commonly known methods known in the art for creating specific RNA sequences. These single guide RNAs are designed to guide the Cas9 to any chosen target site.

Donors

As noted above, insertion of an exogenous sequence (also called a "donor sequence" or "donor"), for example for correction of a mutant gene or for increased expression of a wild-type gene also can be carried out. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest. Alternatively, a donor molecule may be integrated into a cleaved target locus via non-homologous end joining (NHEJ) mechanisms. See, e.g., U.S. Patent Publication Nos. 20110207221 and 20130326645.

The donor polynucleotide can be DNA or RNA, single-stranded or double-stranded and can be introduced into a cell in linear or circular form. See, e.g., U.S. Patent Publication Nos. 20100047805; 20110281361; and 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889.

Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted (e.g., AAVS1, CCR5, albumin, HPRT etc. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an endogenous locus such that some (N-terminal and/or C-terminal to the transgene) or none of the endogenous sequences are expressed, for example as a fusion with the transgene. In other embodiments, the transgene (e.g., with or without additional coding sequences such as for the endogenous gene) is integrated into any endogenous locus, for example a safe-harbor locus.

When endogenous sequences (endogenous or part of the transgene) are expressed with the transgene, the endogenous sequences may be full-length sequences (wild-type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Delivery

The compositions (e.g. ZFPs, TALEs, CRISPR/Cas), polynucleotides encoding same, any donor polynucleotides described herein may be delivered to a target cell containing a TCR gene by any suitable means. Methods of delivering the compositions comprising DNA-binding domains are described, for example, in U.S. Pat. Nos. 6,453,242; 6,503, 717; 6,534,261; 6,599,692; 6,607,882; 6,689,558; 6,824, 978; 6,933,113; 6,979,539; 7,013,219; and 7,163,824, the disclosures of all of which are incorporated by reference herein in their entireties.

Zinc finger, TALE or CRISPR/Cas proteins as described herein may also be delivered using vectors containing sequences encoding one or more of the zinc finger, TALE or CRISPR/Cas protein(s). Donor encoding polynucleotides may be similarly delivered. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824, 978; 6,933,113; 6,979,539; 7,013,219; and 7,163,824, incorporated by reference herein in their entireties. Furthermore, it will be apparent that any of these vectors may comprise one or more zinc finger protein-encoding sequences, one or more CRISPR/Cas-encoding sequences or one or more TALE-encoding sequences. Thus, when one or more nucleases or nuclease systems and/or donors are introduced into the cell, the nucleases or nuclease systems and/or donors may be carried on the same vector or on different vectors. When multiple vectors are used, each vector may comprise a sequence encoding one or multiple ZFPs, TALEs, CRISPR/Cas system and/or donors.

Conventional viral and non-viral based gene transfer methods can be used to introduce nucleic acids encoding engineered ZFPs, TALEs, CRISPR/Cas and/or donors in cells (e.g., mammalian cells) and target tissues. Such methods can also be used to administer nucleic acids encoding ZFPs, TALES, CRISPR/Cas and/or donors to cells in vitro. In certain embodiments, nucleic acids encoding ZFPs, TALEs, CRISPR/Cas and/or donors are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel&Felgner, *TIBTECH* 11:211-217 (1993); Mitani&Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer &Perricaudet, *British Medical Bulletin* 51(1):31-44 (1995); Haddadaet al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See US patents U.S. Pat. Nos. 7,074,596 and 8,153,773, incorporated by reference herein.

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene*

Ther. 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) *Nature Biotechnology* 27(7) p. 643).

The use of RNA or DNA viral based systems for the delivery of nucleic acids encoding engineered ZFPs, TALEs and/or donors take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700). In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors is described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Vectors suitable for introduction of polynucleotides described herein also include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zufferyet al. (1998) *J. Virol.* 72:9873-9880; Follenzi et al. (2000) *Nature Genetics* 25:217-222; U.S. Patent Publication No 20090117617.

Recombinant adeno-associated virus vectors (rAAV) are a promising alternative gene delivery systems based on the defective and nonpathogenic parvovirus adeno-associated type virus. The vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6 and AAV8, AAV 8.2, AAV9, and AAV rh10 and pseudotyped AAV such as AAV2/8, AAV2/5 and AAV2/6 can also be used in accordance with the present invention.

In certain embodiments, the vector is a lentiviral vector. A lentiviral vector, as used herein, is a vector which comprises at least one component part derivable from a lentivirus. A detailed list of lentiviruses may be found in Coffin et at (1997) "*Retroviruses*" Cold Spring Harbour Laboratory Press Eds: J M Coffin, S M Hughes, H E Varmus pp 758-763). Lentiviral vectors can be produced generally by methods well known in the art. See, e.g., U.S. Pat. Nos. 5,994,136; 6,165,782; and 6,428,953. Preferably, the lentiviral vector is an integrase deficient lentiviral vector (IDLV). See, e.g., U.S. Patent Publication 2009/0117617. IDLVs may be produced as described, for example using lentivirus vectors that include one or more mutations in the native lentivirus integrase gene, for instance as disclosed in Leavitt et al. (1996) *J. Virol.* 70(2):721-728; Philippe et al. (2006) *Proc. Natl Acad. Sci USA* 103(47): 17684-17689; and WO 06/010834. In certain embodiments, the IDLV is an HIV lentiviral vector comprising a mutation at position 64 of the integrase protein (D64V), as described in Leavitt et al. (1996) *J. Virol.* 70(2):721-728.

In certain embodiments, the vector is an adenovirus vector. Non-limiting examples of Ad vectors that can be used in the present application include recombinant (such as E1-deleted), conditionally replication competent (such as oncolytic) and/or replication competent Ad vectors derived from human or non-human serotypes (e.g., Ad5, Ad11, Ad35, or porcine adenovirus-3); and/or chimeric Ad vectors (such as Ad5/F35) or tropism-altered Ad vectors with engineered fiber (e.g., knob or shaft) proteins (such as peptide insertions within the HI loop of the knob protein). Also useful are "gutless" Ad vectors, e.g., an Ad vector in which all adenovirus genes have been removed, to reduce immunogenicity and to increase the size of the DNA payload. This allows, for example, simultaneous delivery of sequences encoding ZFNs and a donor sequence. Such gutless vectors are especially useful when the donor sequences include large transgenes to be integrated via targeted integration.

Replication-deficient recombinant adenoviral vectors (Ad) can be produced at high titer, and they readily infect a number of different cell types. Most adenovirus vectors are engineered such that a transgene replaces the Ad E1a, E1b, and/or E3 genes; subsequently the replication defective vector is propagated in cells that provide one or more of the deleted gene functions in trans. For example, human 293 cells supply E1 function. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-1089 (1998)).

Packaging cells are used to form virus particles that are capable of infecting a host cell. Such cells include 293 cells, which package adenovirus, AAV, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

Additional examples of the use of adenovirus vectors for gene transfer in clinical trials include Rosenecker et al., *Infection* 24:1 5-10 (1996); Welsh et al., *Hum. Gene Ther.* 2:205-18 (1995); Alvarez et al., *Hum. Gene Ther.* 5:597-613 (1997); Topf et al., *Gene Ther.* 5:507-513 (1998).

In certain embodiments, the Ad vector is a chimeric adenovirus vector, containing sequences from two or more different adenovirus genomes. For example, the Ad vector can be an Ad5/F35 vector. Ad5/F35 is created by replacing one or more of the fiber protein genes (knob, shaft, tail, penton) of Ad5 with the corresponding fiber protein gene from a B group adenovirus such as, for example, Ad35. The Ad5/F35 vector and characteristics of this vector are described, for example, in Ni et al. (2005) "Evaluation of biodistribution and safety of adenovirus vectors containing group B fibers after intravenous injection into baboons," *Hum Gene Ther* 16:664-677; Nilsson et al. (2004) "Functionally distinct subpopulations of cord blood CD34+ cells are transduced by adenoviral vectors with serotype 5 or 35 tropism," *Mol Ther* 9:377-388; Nilsson et al. (2004) "Development of an adenoviral vector system with adenovirus serotype 35 tropism; efficient transient gene transfer into primary malignant hematopoietic cells," *J Gene Med* 6:631-641; Schroers et al. (2004) "Gene transfer into human T lymphocytes and natural killer cells by Ad5/F35 chimeric adenoviral vectors," *Exp Hematol* 32:536-546; Seshidhar et al. (2003) "Development of adenovirus serotype 35 as a gene transfer vector," *Virology* 311:384-393; Shayakhmetov et al. (2000) "Efficient gene transfer into human CD34(+) cells by a retargeted adenovirus vector," *J Virol* 74:2567-2583; and Soya et al. (2004), "A tumor-targeted and conditionally replicating oncolytic adenovirus vector expressing TRAIL for treatment of liver metastases," *Mol Ther* 9:496-509. As noted above, ZFNs and polynucleotides encoding these ZFNs may be delivered to any target cell. Generally, for inactivating a gene CCR-5, the cell is an immune cell, for example, a lymphocyte (B-cells, T-cells such as T helper ($T_H$) and T cytotoxic cells ($T_C$), null cells such as natural killer (NK) cells); a mononuclear cell (monocytes, marcophages); a granulocytic cell (granulocytes, neutrophils, eosinophils, basophils); a mast cell; and/or a dendritic cell (Langerhans cells, interstitial dendritic cells, interdigitating dendritic cells, circulating dendritic cells). Macrophages, B lymphocytes and dendritic cells are exemplary antigen-presenting cells involved in $T_H$ cell activation. In certain embodiments, the target cell is a $T_H$ cell, characterized by expression of CD4 on the surface. The target cell may also be a hematopoietic stem cell, which may give rise to any immune cell.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the nucleases (e.g. ZFNs or TALENs) or nuclease systems (e.g. CRISPR/Cas). Suitable primary cells include peripheral blood mononuclear cells (PBMC), and other blood cell subsets such as, but not limited to, T-lymphocytes such as CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see, Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176:1693-1702 (1992)).

Stem cells that have been modified may also be used in some embodiments. For example, stem cells that have been made resistant to apoptosis may be used as therapeutic compositions where the stem cells also contain the ZFPs, TALEs, CRISPR/Cas systems and/or donors of the invention. Resistance to apoptosis may come about, for example, by knocking out BAX and/or BAK using BAX- or BAK-specific nucleases (see, U.S. Patent Publication No. 2010/0003756) in the stem cells, or those that are disrupted in a caspase, again using caspase-6 specific ZFNs for example. Alternatively, resistance to apoptosis can also be achieved by the use of caspase inhibitors like Z-VAD-FMK (carbobenzoxy-valyl-alanyl-aspartyl-[O-methyl]-fluoromethyl-ketone).

Vectors (e.g., retroviruses, adenoviruses, liposomes, etc.) containing therapeutic ZFP, TALE, CRISPR/Cas system and/or donor nucleic acids can also be administered directly to an organism for transduction of cells in vivo. Alternatively, naked DNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34$^+$ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

Applications

The disclosed methods and compositions can be used for inactivation of a TCR genomic sequence. As noted above, inactivation includes partial or complete repression of the endogenous TCR α and/or β gene expression in a cell (e.g., T-lymphocyte). Inactivation of a TCR gene can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) or another coding sequence of interest into the gene or its regulatory region, so as to disrupt the gene or regulatory region, or by targeting recombination of a splice acceptor sequence into an intron to cause missplicing of the transcript. Inactivation of an endogenous TCR gene can also be accomplished by targeted recombination of a TCR gene(s) specific for a tumor antigen/MHC complex of interest.

There are a variety of applications for nuclease-mediated inactivation (knockout or knockdown) of a TCR gene. For example, the methods and compositions described herein allow for the generation and/or modification of cells lines (for therapeutic and non-therapeutic uses). Inactivation of the endogenous TCR gene(s) may be coupled with the insertion of genes encoding high avidity TCRs or chimeric antigen receptors (CARS, see Cartellieri et at (2010) *J Biomed and Biotech*, Vol 2010, Article ID 956304) against a known target, and the resultant transgenic cells (or descendants of these cells having the same characteristics) may be used as cellular therapeutics. Alternatively, the re-targeting of the T cell may occur in vivo, using viral vectors to deliver both the genes encoding the TCR-specific nucleases and the high avidity TCR on a donor nucleic acid. In either case, the materials and methods of the invention may be used in the treatment of cancer. Cells modified in vitro may also be used for modeling studies or for screening to find other types of therapeutics that may also work in concert with the TCR modification. Any type of cancer can be treated, including, but not limited to lung carcinomas, pancreatic cancers, liver cancers, bone cancers, breast cancers, colorectal cancers, ovarian cancers, leukemias, lymphomas, brain cancers and the like. Other diseases that may be treated with the technology of the invention include fungal, bacterial and viral infections as well as autoimmune diseases and graft-versus-host disease (GvHD).

In addition, the methods and compositions described herein can be used to generate model organisms and cell lines, including the generation of stable knock-out cells in any given organism. While ZFN/TALENs/CRISPR/Cas systems offer the ability to knock-out any given gene in cell lines or model organism, in the absence of selection marker these events however can be very rare. Accordingly, the methods described herein, which significantly increase the rate of targeted gene disruption, can be used to generate cell line with new properties. This includes cell lines used for the production of biologicals like Hamster (CHO) cell lines or cell lines for the production of several AAV serotypes like human HEK 293 cells or insect cells like Sf9 or Sf21.

The methods and compositions of the invention can also be used in the production of transgenic organisms. Transgenic animals can include those developed for disease models, as well as animals with desirable traits. Embryos may be treated using the methods and compositions of the invention to develop transgenic animals. In some embodiments, suitable embryos may include embryos from small mammals (e.g., rodents, rabbits, etc.), companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a *Drosophila* embryo or a mosquito embryo.

EXAMPLES

Example 1

Expression of an Optimized, High Affinity WT-1 TCR Construct

Genes encoding for a codon-optimized, cysteine-modified TCR specific for an HLA-A2-restricted peptide from the Wilms tumor antigen 1 (WT1), specifically the WT1$_{126\text{-}134}$ peptide (Kuball et al (2007) *Blood* 109(6):2331-8) and single α21 or β21 WT1 specific TCR chains were cloned into bidirectional self-inactivating transfer vectors pCCLsin.PPT.ΔLNGFR.minCMV.WPGK.eGFP.Wpre or pCCLsin.cPPT.ΔLNGFR.min.CMV.hEF1a.eGFP.Wpre as described in Amendola et al (2005) *Nature Biotechnology* 23(1): 108-116, Thomas et al (2007) *J. Immunol* 179 (9): 5803-5810, and U.S. Patent Publication No US2006200869 (see FIG. 1A)

The vectors were packaged using an integrase-competent third generation lentivirus vector system, and pseudotyped by VZV envelope, essentially as described in Follenzi and Naldini (2002) *Methods in Enzymology* 346: 454-465. The lentiviral vectors were then used to transduce cells using standard techniques (see below) and cells were characterized by FACs analysis to determine if the exogenous TCRs were being expressed on the cell surface.

As shown below in Table 1, the WT-1 specific TCR construct was highly expressed, whether driven from the PGK/mCMV dual promoter combination or the EF1α/mCMV dual promoter construct. Numbers in Table are presented as percent of total signal present in the quadrant gated for VB21 expression and WT1-HLA-A2 pentamer binding.

TABLE 1

Expression of WT-1 TCR

| Promoter | Day 14 | Day 22 |
| --- | --- | --- |
| PGK | 12.1 | 21.3 |
| EF1α | 1.48 | 5.16 |

Untransduced = 0.085

Figure 1B:
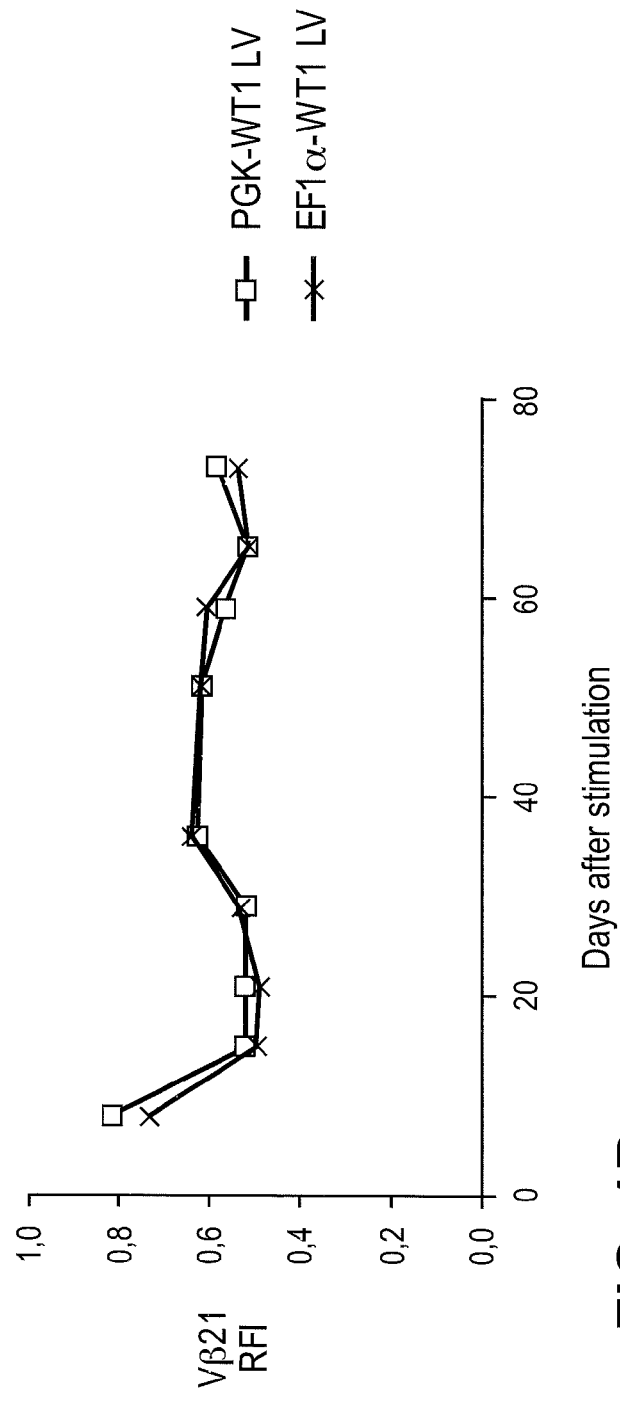
FIG. 1B is a graph depicting a time course of Vβ21 TCR expression in lentivirus transduced $CD8^+$ cells cultured in the presence of 5 ng/ml of IL7 and IL15. Vβ21 relative fluorescence intensity (RFI) was calculated as the ratio of the mean fluorescence intensity (MFI) of Vβ21 measured in PGK-WT1 (open squares) or EF1α-WT1 ("X") genetically modified lymphocytes/the MFI of Vβ21 measured in T cells naturally expressing Vβ21.

Transduction of T cells was accomplished by activating the cells with anti-CD3/anti-CD28 antibody-conjugated magnetic beads (Clin ExVivo CD3/CD28; Invitrogen) (baCD3/CD28) where the cells were cultured in IMDM (GIBCO-BRL), 10% FCS with low dose IL-7/IL-15 as described in European Patent Publication No EP1956080 and Kaneko et at (2009) *Blood* 113: 1006-1015. This procedure preserved an early T cell differentiation phenotype (CD45RA−/+CD62L+, CD28+CD27+, IL7Ra+, IL-2+ γIFN−/+), and the cells proliferated indistinguishably from untransduced lymphocytes. In these conditions, the PGK dual promoter proved to be superior to the EF1α dual promoter in sustaining stochiometric expression of WT1-specific TCR chains, suggesting that the PGK bi-directional promoter exerts a higher activity in the antisense direction than the bi-directional EF1α promoter. Both promoters however, when tested in the context of a lentiviral vector, supported TCR expression at levels appropriate for efficient HLA-A2/WT1 pentamer binding (16%), for >70 days after initial stimulation (see FIG. 1B).

TCR transduced cells were also able to exhibit specific γIFN production and cytotoxic activity against WT1+HLA-A2+ primary leukemic blasts from AML patients. In particular, γIFN production in cells transduced with vectors expressing the transgenic TCRs either from the PGK/mCMV dual promoter combination or the EF1α/mCMV dual promoter was increased (FIG. 2A) as was % killing (lysis) by the TCR modified cells (FIGS. 2B and 2C). In addition, γIFN production was inhibited in the edited lymphocytes (FIG. 2D), in the presence of unlabelled targets expressing the HLA-restriction element and pulsed with the target peptide.

Example 2

Efficient Integration of a Transgene into the CCR5 Locus of Central Memory T Cells To test the idea of integrating the WT-1 specific TCR genes into a central memory T cell, GFP was used first as a donor nucleic acid to monitor transduction efficiency and GFP expression from the site of integration. The CCR5 locus was chosen because it has been shown that CCR5 knockout cells are fully functional (see U.S. Pat. No. 7,951,925). In addition, the PPP1R12C (AAVS1) locus was similarly targeted (see US Patent Publication 20080299580) The GFP-encoding donor was transduced into the cell using an IDLV vector and the CCR5-specific ZFNs or AAVS1-specific ZFNs were introduced using an Ad5/F35 vector as described above. GFP expression was measured 20 days following transduction.

Figure 3A:
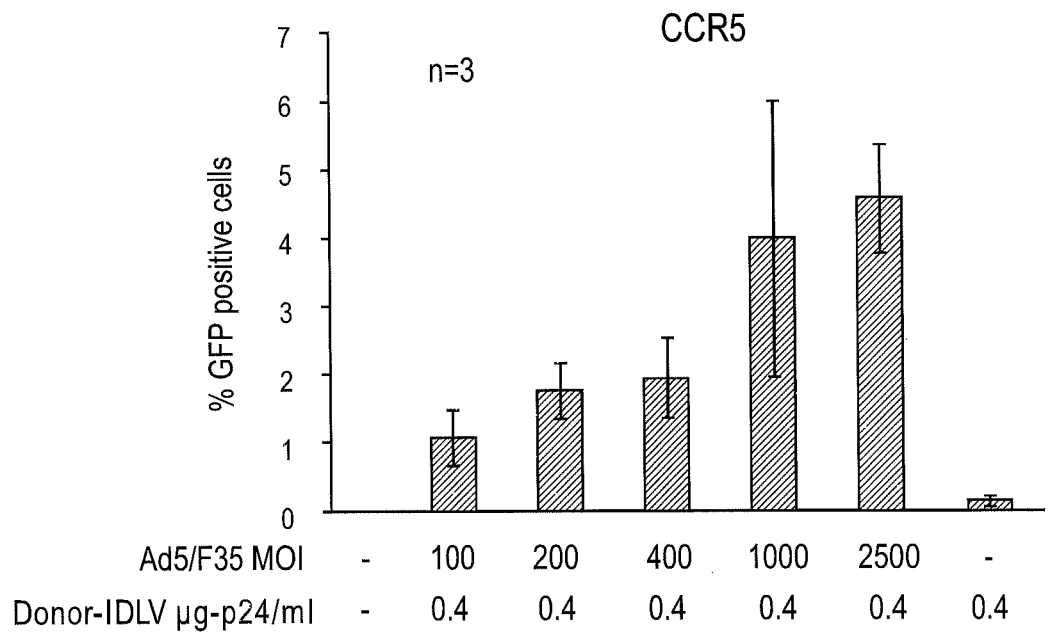
FIGS. 3A and 3B demonstrate the increase in the percentage of GFP positive cells in relation to the amount of Ad5/F35 CCR5-specific ZFN (FIG. 3A) or Ad5/F35 AAVS1-specific ZFN (FIG. 3B) and -IDLV GFP donor DNA cassette used.
Figure 3B:
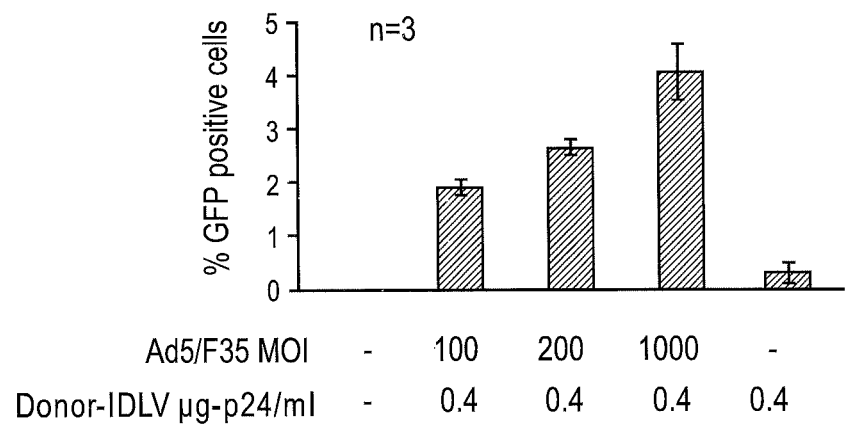

As shown in FIG. 3, ZFN-mediated integration of GFP transgenes resulted in increased GFP signals, including in relation to the amount of Ad5/F35 donor used (FIGS. 3A and 3B). Table 2 below shows the increase in the percent of GFP positive cells in the presence of donor or donor plus ZFNs.

TABLE 2

| | GFP signal, percent positive cells | | |
|---|---|---|---|
| Insert site | UT | +donor | donor + ZFN |
| CCR5 | 0.038 | 0.083 | 6.11 |
| AAVS1 | 0.015 | 0.18 | 4.38 |

Example 3

Integration of WT-1 Specific TCR Transgenes into the CCR5 Locus of Jurkat TCR β-negative Cells The WT-1 specific TCR transgene construct was then used for targeted integration into the CCR5 locus of Jurkat cells that are TCR β-negative following treatment with TCR-β specific ZFNs. Cells were transfected using standard techniques with WT-1 TCR construct similar to that described in Example 1.

As seen in Table 3, after introduction of the WT-1 TCR donor (WT1-TCR IDLV) and the CCR5-specific ZFNs (Ad-ZFNs), there is a marked increase in Vβ21 staining or signal, while without the donor or the ZFNs, only background Vβ21 signal is seen. Thus, ZFN-mediated integration of the WT-1 specific TCR into the CCR5 locus occurred in a substantial percentage of the cells.

TABLE 3

| Percent of total signal from VB21 + expression | | | | |
|---|---|---|---|---|
| WT1-TCR IDLV | + | + | + | − |
| Ad ZFNs | + | ++ | − | − |
| Percent VB21+ | 16.6 | 18.7 | 2.27 | 0.81 |

Example 4

Design of TCR-specific ZFNs

TCR-specific ZFNs were constructed to enable site specific introduction of double strand breaks at either the TCRα and/or TCRβ genes. ZFNs were designed and incorporated into plasmids or IDLV vectors essentially as described in Urnov et al. (2005) *Nature* 435(7042):646-651, Lombardo et at (2007) *Nat Biotechnol*. November; 25(11):1298-306, and U.S. Patent Publication 2008/0131962. The recognition helices for exemplary ZFN pairs as well as the target sequence are shown below in Tables 4 and 5. Target sites of the TCR zinc-finger designs are shown in the first column. Nucleotides in the target site that are contacted by the ZFP recognition helices are indicated in uppercase letters; non-contacted nucleotides indicated in lowercase.

TABLE 4

| TCR-α Zinc-finger Designs | | | | | | |
|---|---|---|---|---|---|---|
| ZFN Name Target sequence | F1 | F2 | F3 | F4 | F5 | F6 |
| 25529 (ex 1) ctATGGACtT CAAGAGCAa cagtgctgt (SEQ ID NO: 1) | QSGDLTR (SEQ ID NO: 2) | QRTHLKA (SEQ ID NO: 3) | QSGDRNK (SEQ ID NO: 4) | DRSNLSR (SEQ ID NO: 5) | RSDALTQ (SEQ ID NO: 6) | N/A |
| 25528 (ex 1) ctCATGTCTA GcACAGTTttg tctgtga (SEQ ID NO: 7) | TSGSLSR (SEQ ID NO: 8) | QSSVRNS (SEQ ID NO: 9) | RSDNLST (SEQ ID NO: 10) | DRSALAR (SEQ ID NO: 11) | LKQNLDA (SEQ ID NO: 12) | N/A |
| 25535 (ex 1) gtGCTGTGGC CtGGAGCAac aaatctga (SEQ ID NO: 13) | DRSALSR (SEQ ID NO: 14) | QSGHLSR (SEQ ID NO: 15) | DRSDLSR (SEQ ID NO: 16) | RSDALSR (SEQ ID NO: 17) | DRSDLSR (SEQ ID NO: 16) | N/A |
| 25534 (ex 1) ttGCTCTTGA AGTCcATAG ACctcatgt (SEQ ID NO: 18) | DRSNLSR (SEQ ID NO: 5) | QKTSLQA (SEQ ID NO: 19) | DRSALSR (SEQ ID NO: 14) | QSGNLAR (SEQ ID NO: 20) | GKEELNE (SEQ ID NO: 21) | RSSDLSR (SEQ ID NO: 22) |

TABLE 4-continued

TCR-α Zinc-finger Designs

| ZFN Name Target sequence | F1 | F2 | F3 | F4 | F5 | F6 |
|---|---|---|---|---|---|---|
| 25537 (ex 1) gcTGTGGCCT GGAGCAAca aatctgact (SEQ ID NO: 23) | GNVDLIE (SEQ ID NO: 24) | RSSNLSR (SEQ ID NO: 25) | RSDALSV (SEQ ID NO: 26) | DSSHRTR (SEQ ID NO: 27) | WRSCRSA (SEQ ID NO: 28) | N/A |
| 25536 (ex 1) ctGTTGCTcT TGAAGTCCat agacctca (SEQ ID NO: 29) | DSSDRKK (SEQ ID NO: 30) | RSDNLSV (SEQ ID NO: 31) | RRFILRG (SEQ ID NO: 32) | QSGDLTR (SEQ ID NO: 2) | TSGSLTR (SEQ ID NO: 33) | N/A |
| 25538 (ex 1) ctGTGGCCtG GAGCAACAa atctgactt (SEQ ID NO: 34) | QSGDLTR (SEQ ID NO: 2) | QTSTLSK (SEQ ID NO: 35) | QSGHLSR (SEQ ID NO: 15) | DRSDLSR (SEQ ID NO: 16) | RSDALAR (SEQ ID NO: 36) | N/A |
| 25540 (ex 1) ctGACTTTGC ATGTGCAaac gccttcaa (SEQ ID NO: 37) | QSGDLTR (SEQ ID NO: 2) | WRSSLAS (SEQ ID NO: 38) | QSGDLTR (SEQ ID NO: 2) | HKWVLRQ (SEQ ID NO: 39) | DRSNLTR (SEQ ID NO: 40) | N/A |
| 25539 (ex 1) ttGTTGCTcC AGGCCACA GCActgttgc (SEQ ID NO: 41) | QSGDLTR (SEQ ID NO: 2) | QWGTRYR (SEQ ID NO: 42) | ERGTLAR (SEQ ID NO: 43) | RSDNLRE (SEQ ID NO: 44) | QSGDLTR (SEQ ID NO: 2) | TSGSLTR (SEQ ID NO: 33) |
| 22199 (ex 3) tgAAAGTGG CCGGGtttaatct gctcat (SEQ ID NO: 45) | RSAHLSR (SEQ ID NO: 46) | DRSDLSR (SEQ ID NO: 16) | RSDHLSV (SEQ ID NO: 47) | QNNHRIT (SEQ ID NO: 48) | N/A | N/A |
| 22189 (ex 3) agGAGGATT CGGAAcccaat cactgaca (SEQ ID NO: 49) | QRSNLVR (SEQ ID NO: 50) | RNDDRKK (SEQ ID NO: 51) | TSGNLTR (SEQ ID NO: 52) | TSANLSR (SEQ ID NO: 53) | N/A | N/A |
| 25572 (ex 3) gaGGAGGAtT CGGAACCCa atcactgac (SEQ ID NO: 54) | DRSTLRQ (SEQ ID NO: 55) | QRSNLVR (SEQ ID NO: 50) | RNDDRKK (SEQ ID NO: 51) | RSAHLSR (SEQ ID NO: 46) | QSGHLSR (SEQ ID NO: 15) | N/A |
| 25573 (ex 3) gaGGAGGAtT CGGAAcccaat cactgac (SEQ ID NO: 54) | QRSNLVR (SEQ ID NO: 50) | RNDDRKK (SEQ ID NO: 51) | QSGHLAR (SEQ ID NO: 56) | QSGHLSR (SEQ ID NO: 15) | N/A | N/A |
| 22199 (ex 3) tgAAAGTGG CCGGGtttaatct gctcat (SEQ ID NO: 57) | RSAHLSR (SEQ ID NO: 46) | DRSDLSR (SEQ ID NO: 16) | RSDHLSV (SEQ ID NO: 47) | QNNHRIT (SEQ ID NO: 48) | N/A | N/A |

TABLE 5

TCR-β Zinc-finger Designs

| ZFN Name Target sequence | F1 | F2 | F3 | F4 | F5 | F6 |
|---|---|---|---|---|---|---|
| 16783 ccGTAGAACT GGACTTGaca gcggaagt (SEQ ID NO: 58) | RSDVLSA (SEQ ID NO: 59) | DRSNRIK (SEQ ID NO: 60) | RSDVLSE (SEQ ID NO: 61) | QSGNLAR (SEQ ID NO: 20) | QSGSLTR (SEQ ID NO: 62) | N/A |
| 16787 tcTCGGAGAA TGACGAGTG Gacccagga (SEQ ID NO: 63) | RSDHLST (SEQ ID NO: 64) | RSDNLTR (SEQ ID NO: 65) | DRSNLSR (SEQ ID NO: 5) | TSSNRKT (SEQ ID NO: 66) | RSANLAR (SEQ ID NO: 67) | RNDDRKK (SEQ ID NO: 51) |
| 22409 tcTCGGAGAA TGACGAGTG Gacccagga (SEQ ID NO: 63) | RSDHLST (SEQ ID NO: 64) | RSDNLTR (SEQ ID NO: 65) | DRSNLSR (SEQ ID NO: 5) | LQFNRNQ (SEQ ID NO: 68) | RSANLAR (SEQ ID NO: 67) | RNDDRKK (SEQ ID NO: 51) |
| 22449 tcTCGGAGAA TGACGAGTG Gacccagga (SEQ ID NO: 63) | RSDHLST (SEQ ID NO: 64) | RSDNLTR (SEQ ID NO: 65) | DSSNLSR (SEQ ID NO: 69) | LRFNLSN (SEQ ID NO: 70) | RSANLAR (SEQ ID NO: 67) | RNDDRKK (SEQ ID NO: 51) |
| 22454 tcTCGGAGAA TGACGAGTG Gacccagga (SEQ ID NO: 63) | RSDHLST (SEQ ID NO: 64) | RSDNLTR (SEQ ID NO: 65) | DSSNLSR (SEQ ID NO: 69) | LHFQLTG (SEQ ID NO: 71) | RSANLAR (SEQ ID NO: 67) | RNDDRKK (SEQ ID NO: 51) |
| 25814 ccGTAGAACT GGACTTGaca gcggaagt (SEQ ID NO: 58) | RSDVLSA (SEQ ID NO: 59) | DRSNRIK (SEQ ID NO: 60) | RSDVLSE (SEQ ID NO: 61) | QSGNLAR (SEQ ID NO: 20) | QSGSLTR (SEQ ID NO: 62) | N/A |
| 25818 ccGTAGAACT GgaCTTGACa gcggaagt (SEQ ID NO: 58) | DRSNLSR (SEQ ID NO: 5) | LKFALAN (SEQ ID NO: 72) | RSDVLSE (SEQ ID NO: 61) | QSGNLAR (SEQ ID NO: 20) | QSGSLTR (SEQ ID NO: 62) | N/A |
| 25820 ccGTAGAACT GGACTTGaca gcggaagt (SEQ ID NO: 58) | RSDVLSA (SEQ ID NO: 59) | DRSNRIK (SEQ ID NO: 60) | RSDVLSE (SEQ ID NO: 61) | QSGNLAR (SEQ ID NO: 20) | QSGALAR (SEQ ID NO: 73) | N/A |
| 25822 ccGTAGAACT GGACTTGaca gcggaagt (SEQ ID NO: 58) | RLSVLTI (SEQ ID NO: 74) | DRANLTR (SEQ ID NO: 75) | RSDVLSE (SEQ ID NO: 61) | QSGNLAR (SEQ ID NO: 20) | QSGALAR (SEQ ID NO: 73) | N/A |

Example 5

ZFN Activity In Vitro

The ZFNs described in Tables 4 and 5 were used to test nuclease activity in K562 cells. To test cleavage activity, plasmids encoding the pairs of human TCR-specific ZFNs described above were transfected into K562 cells. K562 cells were obtained from the American Type Culture Collection and grown as recommended in RPMI medium (Invitrogen) supplemented with 10% qualified fetal bovine serum (FBS, Cyclone). For transfection, one million K562 cells were mixed with 2 μg of the zinc-finger nuclease plasmid and 100μL Amaxa Solution V. Cells were transfected in an Amaxa Nucleofector II™ using program T-16 and recovered into 1.4 mL warm RPMI medium+10% FBS.

Genomic DNA was harvested and a portion of the TCR locus encompassing the intended cleavage site was PCR amplified using the Accuprime HiFi polymerase from Invitrogen as follows: after an initial 3 minute denaturation at 94° C., 30 cycles of PCR were performed with a 30 second denaturation step at 94° C. followed by a 30 second annealing step at 58° C. followed by a 30 second extension step at 68° C. After the completion of 30 cycles, the reaction was incubated at 68° C. for 7 minutes, then at 4° C. indefinitely.

The genomic DNA from the K562 TCR-specific ZFN-treated cells was examined by the Cel-I assay as described, for example, in U.S. Patent Publication Nos. 20080015164; 20080131962 and 20080159996.

Figure 4A:
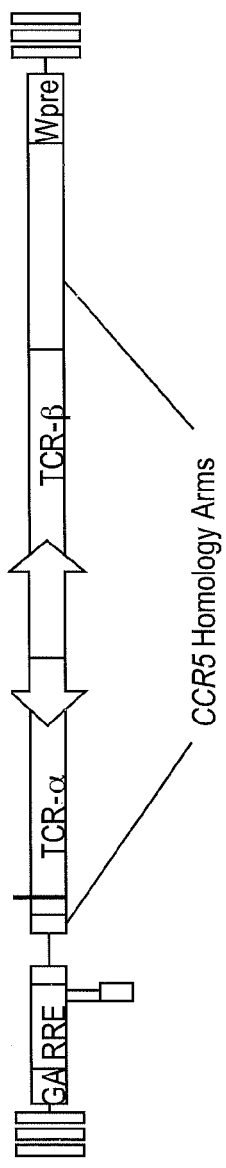
FIG. 4A depicts a cassette containing WT1-specific TCR-α and TCR-β donor molecules and shows the regions of homology to the CCR5 integration site.
Figure 4B:
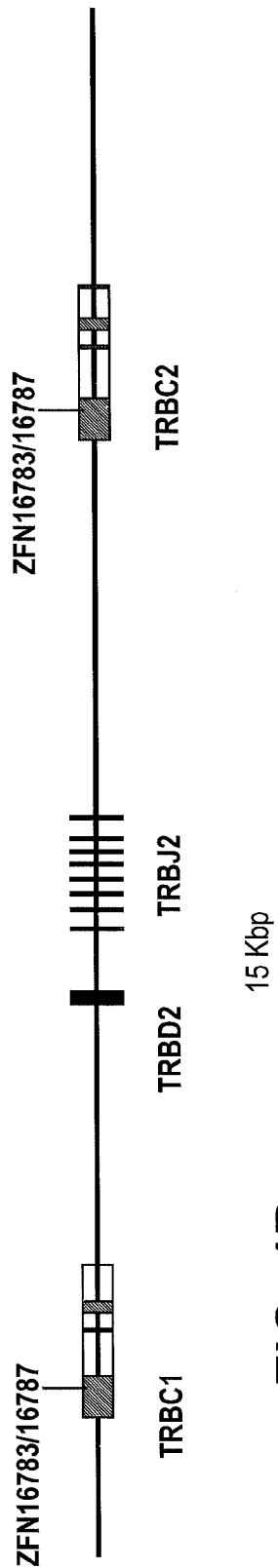
FIG. 4B depicts the genomic arrangement of the two TCR-β constant regions in K562 cells (TRBC1 and TRBC2).

The TCR beta locus in K562 cells has two functional copies with high sequence similarity (TRBC1 and TRBC2) which are both targeted by TCR beta specific ZFNs. See, FIG. 4B. Thus, initially, PCR primers that would specifically amplify the regions around the intended ZFN cleavage sites specifically from either the TRBC1 or the TRBC2 genes were used to separately analyze NHEJ activity following ZFN driven cleavage for both genes. Exemplary results are presented in Table 6 below for ZFN pair 16787 and 16783.

TABLE 6

NHEJ activity for pairs of TCR beta-specific ZFNs: analysis of TRBC1 and TRBC2

| | NHEJ in TRBC2 | | | | NHEJ in TRBC1 | | |
|---|---|---|---|---|---|---|---|
| TRBC2 | ZFN1 | ZFN2 | % NHEJ | TRBC1 | ZFN1 | ZFN2 | % NHEJ |
| | 16787 | 16783 | 8.68 | | 16787 | 16783 | 8.73 |
| | GFP | | 0.00 | 21 | GFP | | 0.00 |
| | Mock | | 0.00 | 22 | Mock | | 0.00 |
| | Water control | | 0.00 | 23 | Water control | | 0.00 |

The data presented in Table 6 demonstrate that the ZFNs cleave the TRBC1 and TRBC2 genes essentially equally.

In addition, we tested persistence of ZFN mediated modification of TRBC in K562 cells by harvesting samples at 3 and 10 days after transfection. Results are presented in Table 7 below and demonstrate that with the ZFN pair, 16787 and 16783, target gene modification is stable 10 days following transfection.

TABLE 7

TCR beta-specific ZFNs in K562 cells

| ZFN 1 | ZFN 2 | % NHEJ | |
|---|---|---|---|
| 22449 | 16783 | 20.1 | Day 3 |
| 22454 | 16783 | 17.7 | |
| 16787 | 16783 | 12.1 | |
| GFP | | 0.0 | |
| 22409 | 16783 | 14.7 | Day 10 |
| 22449 | 16783 | 8.1 | |
| 22454 | 16783 | 12.1 | |
| 16787 | 16783 | 15.6 | |
| GFP | | 0.0 | |

Figure 5:
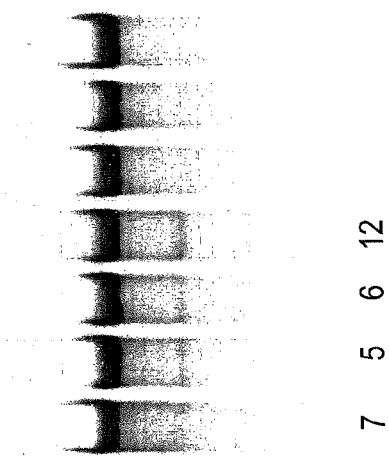
FIG. 5 depicts the percent modification for several pairs of TCR-β-specific ZFNs in K562 cells as measured by a Cel-I Surveyor™ mismatch assay ("Cel-I assay" Transgenomic) The cells were incubated initially at 30° C. following transfection, with either 0.1 or 0.4 μg of ZFN plasmid. Percent modification is shown at the bottom of the lanes.

Several ZFN pairs targeting TRBC were analyzed for NHEJ activity following varying amounts of input ZFN (either 0.4 or 0.1 μg of each ZFN). As shown in FIG. 5, all ZFN pairs tested exhibited high activity. In this experiment, the cells were treated with a 30° C. incubation period following transduction with the ZFNs (see U.S. Patent Publication No: 20110129898). Following analysis of TCR beta-specific ZFN cleavage in K562 cells, several ZFN pairs were tested in either CD4+ or CD8+ mature T cells. Briefly, CD8+ or CD4+ cells were purchased from AllCells and were cultured in RPMI+10% FBS+1% L-Glutamine (30 mg/mL)+IL-2 (30 μg/mL, Sigma) and allowed to rest for 4-24 hours.

Lentiviral vectors were constructed containing the ZFN pairs of interest. They were generated from the HIV derived self-inactivating vector construct and packaged using an HIV integrase carrying the D64V mutation and pseudotyped with the VSV-G envelope as described above. The Ad5/F35 adenoviral vectors were generated as described previously (Perez et al, (2008) *Nature Biotechnology* 26: 808-816) after cloning the two sets of ZFNs using a 2A sequence and a cytomegalovirus internal promoter. See, e.g., Holst J et at (2006) *Nat Protoc.* 1(1):406-17. 1e6 cells/nucleofection were used with the Amaxa™ Nucleofection kit as specified by the manufacturer for each transduction. Cells were activated 12-24 hours post nucleofection with anti-CD3/CD28 beads according to manufacturer's protocol (Invitrogen) and grown in IMDM (GIBCO-BRL), 10% FCS media supplemented with 5 ng/mL of IL-7 and IL-15 (Peprotech).

Cells were harvested 3 days after nucleofection and gene modification efficiency was determined using a Cel-I assay, performed as described in International Patent Publication WO 07/014275. See, also, Oleykowski et al. (1998) *Nucleic Acids Res.* 26:4597-4602; Qui et al. (2004) *BioTechniques* 36:702-707; Yeung et al. (2005) *BioTechniques* 38:749-758. Several of the ZFN pairs had good activity as measured by the Cel-I assay (NHEJ from 4-11.9%).

Figure 6:
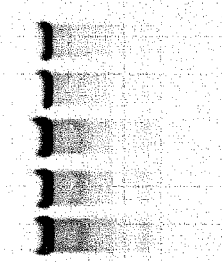
FIG. 6, panels A and B, depict percent modification for TCR-α specific ZFNs in K562 cells as measured by a Cel-I assay.
Figure 6:
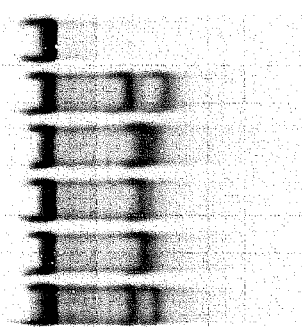

TCR-α-specific ZFNs were also tested in vitro as described above. The cells were incubated at 37° C. for 1 day following the transduction prior to shifting the incubation temperature to 30° C. as described above. See, U.S. Patent Publication No. 20110129898. These ZFNs target the TRAC gene, results of a Cel-I assay performed on K562 cells that received various combinations of these ZFNs as described above showed high activity. See, FIG. 6.

Example 6

Disruption of TCR-β in Cells

The TCR-β-specific ZFNs were then used in experiments to specifically target the TCR locus. Initial experiments were designed to disrupt the TCR locus in Jurkat cells. TCR-β-specific ZFNS 16783 and 16787 were introduced on integrase-defective lentiviral vectors (IDLV) to transiently express the TRBC-targeting ZFNs. Transductions were performed with 0.25 μg or 0.5 μg doses of IDLV, based on measurements of HIV Gag p24 in the vector preparations, 48 hours after activation. Vector infectivity ranged from 1 to $5 \times 10^4$ transducing units/ng p24 by vector DNA titration on 293T cells. Cells were then assayed by FACS analysis for loss of the CD3 marker and CD3(−) cells were enriched using LD columns with anti-CD3 MACS Microbeads (Miltenyi Biotec) according to the manufacturer's instructions.

As shown below in Table 8, following transduction with the ZFNs, there was a vector dose-dependent abrogation of cell surface expression of the TCR/CD3 complex reaching up to 20% of treated cells.

TABLE 8

Loss of CD3 signal in Jurkat cells treated with TCR-β specific ZFN IDLVs

|  | Untransformed | 0.25 μg IDLV | 0.5 μg IDLV |
|---|---|---|---|
| Percent CD3(−) | 2.7 | 13.4 | 20.2 |

Figures 7A, 7B:
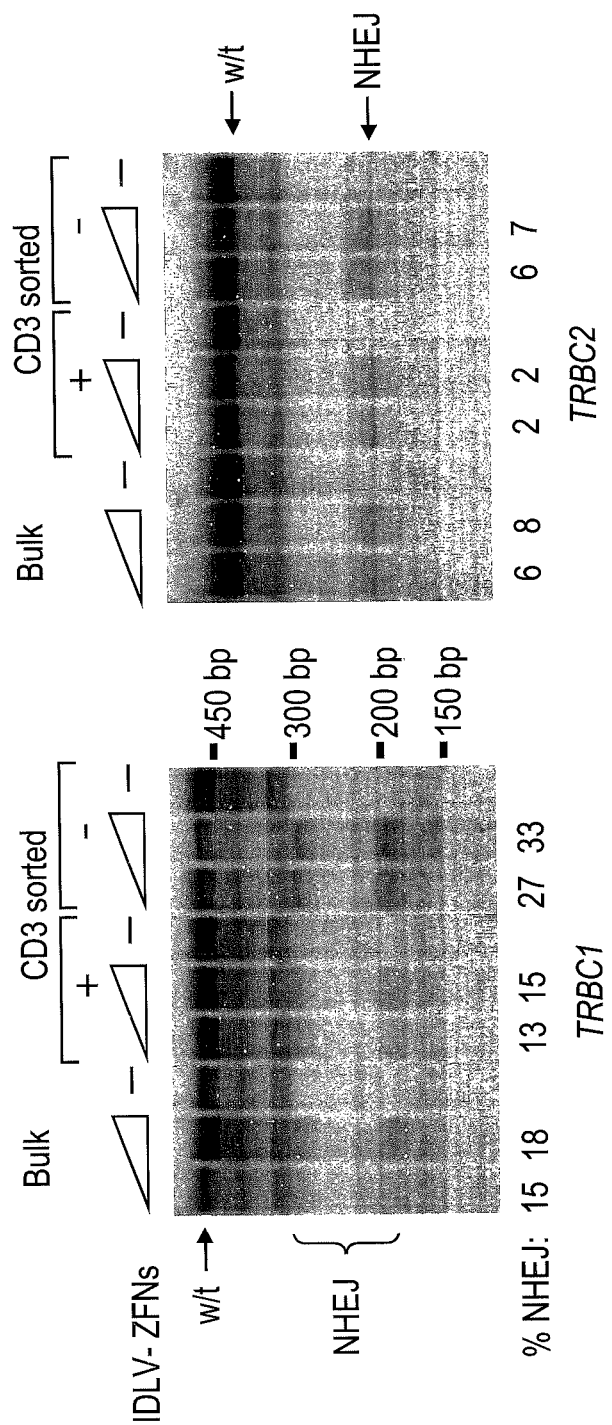
FIGS. 7A and 7B show the results of Cel-I assays at the TRBC1 (FIG. 7A) and the TRBC2 (FIG. 7B) locus in Jurkat cells and demonstrate that cleavage has occurred. The measured % gene modification is indicated at the bottom of each lane.

A Cel-I assay was performed and confirmed these results with up to 26% of the TRBC alleles (18% TRBC1 and 8% of TRBC2) disrupted in the ZFN treated cells (see FIGS. 7A and 7B, "Bulk").

Next, The TRBC ZFNs (16783 and 16787) were introduced into primary human T lymphocytes, and a similar level of CD3 disruption was observed by FACS, as seen in Jurkat cells. Peripheral blood T cells were harvested from healthy donors and activated with CD3 and CD28 conjugated beads. 48 hours post activation the cells were exposed to increasing doses of IDLVs containing the TRBC-specific ZFNs. The cells were then cultured in the presence of low dose (5 ng/mL) IL-7 and IL-15 to promote cell survival and growth. In the primary lymphocytes, up to 7% of the treated cells were CD3 negative while almost no CD3(−) cells were observed in the untreated control and the data is presented below in Table 9.

TABLE 9

Loss of CD3 signal in primary human T lymphocytes treated with TCR-β specific ZFN IDLVs

|  | UT | 2.5 μg IDLV | 5 μg IDLV | 18.5 μg IDLV |
|---|---|---|---|---|
| Percent CD3 (−) | 0.17 | 2.94 | 3.26 | 7.07 |

Figures 7C, 7D:
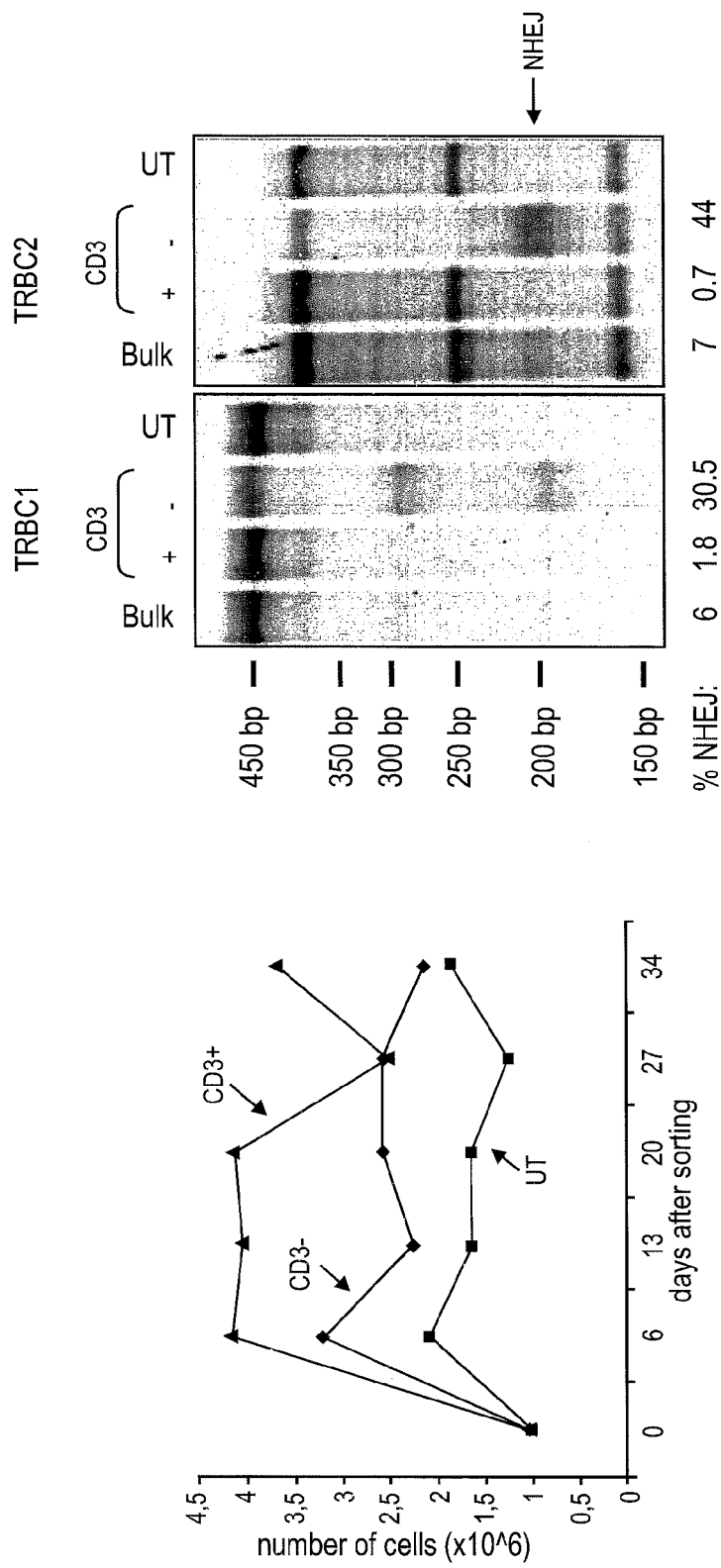
FIG. 7C is a graph depicting that sorted CD3− primary human lymphocytes can survive in the presence of IL7 and IL15. "UT" indicates untreated cells.
FIG. 7D shows the percent modification (NHEJ), as assayed by the Cel-I assay observed in the primary T-cell cell pools treated with TCR-beta specific ZFNs. "Bulk" indicates percent of NHEJ observed for the ZFN treated cell pool, while CD3+ or CD3− shows the NHEJ observed for cells that were sorted either as CD3+ or CD3−. "UT" indicates cells that were not treated. The percent NHEJ detected by the assay is indicated at the bottom of the lanes.

Sorted CD3(−) lymphocytes could be expanded and survived over time in the presence of IL7 and ILL5 (see FIGS. 7C and 7D), where percent modification is indicated in FIG. 7D. FIG. 7E further demonstrates that the CD3(−) cells persist in the population for at least 45 days and also show that the percent of CD3(−) cells in the population stays fairly constant over that time period. The CD3(−) cells do not appear to respond to non-specific mitogen stimulation since, PHA stimulation results in a decrease in the percent of CD3(−) cells in the pool due to expansion of the CD3(+) lymphocytes (FIG. 7F). This result demonstrates absence of CD3 functional signaling in the CD3(−) cells. No phenotypic differences were observed in the CD3(+) and CD3(−) lymphocytes which displayed a similar CD4/CD8 ratio. CD3(−) cells also maintain a central memory phenotype since they remain positive for CD62L, CD28 and IL-7RA (see Table 10 below).

TABLE 10

CD3(−) cells maintain a Central Memory Phenotype- percent of total fluorescence

|  | CD3(−) | CD3(+) |
|---|---|---|
| CD62L(+)/CD3(−) | 97.6 | 0 |
| CD62L(+)/CD3(+) | 1.25 | 98.4 |

TABLE 10-continued

CD3(−) cells maintain a Central Memory Phenotype- percent of total fluorescence

|  | CD3(−) | CD3(+) |
|---|---|---|
| CD62L(−)/CD3(−) | 1.11 | 0 |
| CD62L(−)/CD3(+) | 0 | 1.61 |
| CD28(+)/CD27(−) | 4.66 | 3.23 |
| CD28(+)/CD27(+) | 93.4 | 94.7 |
| CD28(−)/CD27(−) | 0.87 | 0.68 |
| CD28(−)/CD27(+) | 0.97 | 1.43 |
| IL-7RA(+)/CD8(−) | 38.8 | 40.7 |
| IL-7RA(+)/CD8(+) | 47 | 47 |
| IL-7RA(−)/CD8(−) | 3.83 | 2.84 |
| IL-7RA(−)/CD8(+) | 10.4 | 9.42 |

Memory T lymphocytes are less dependent upon TCR signals for homeostatic proliferation than naive T cells; we thus investigated whether homeostatic cytokines could promote survival and growth of previously activated cells, in the absence of TCR expression. Remarkably, the TRBC-ZFNs treated cells could be expanded in culture by supplementation with low dose IL-7 and IL-15, with the proportion of CD3(−) cells remaining stable for more than 50 days in the absence of TCR triggering. Thus, ZFN exposure was well-tolerated in primary lymphocytes and resulted in the stable disruption of the targeted TRBC gene. Therefore, CD3(−) cells were sorted to near purity and further expanded with IL-7 and IL-15 for more than 3 weeks with growth rates similar to CD3(+) cells, demonstrating that homeostatic cytokines do not require TCR signaling functions to promote survival/proliferation of previously activated cells.

These data demonstrate the successful generation of a novel population of CD8 T cells with phenotypic characteristics of $T_{CM}$ but with surface expression of the endogenous TCR permanently disrupted.

Example 7

Introduction of aWT-1 Specific TCR in Cells that had Previously had the Endogenous TCR Permanently Disrupted CD3(−) T lymphocytes were sorted after treatment with the TCR β-specific ZFNs and a lentivirus used to randomly integrate the WT1-TCR β transgene as described in FIG. 1 (49.5±30% mean±SD transduction efficiency, n=4). Thus, in TCR-β-edited cells, expression of the transferred WT1-TCR from an integrated vector rescued surface translocation of CD3 (FIG. 8, $1^{st}$ row).

Figure 8:
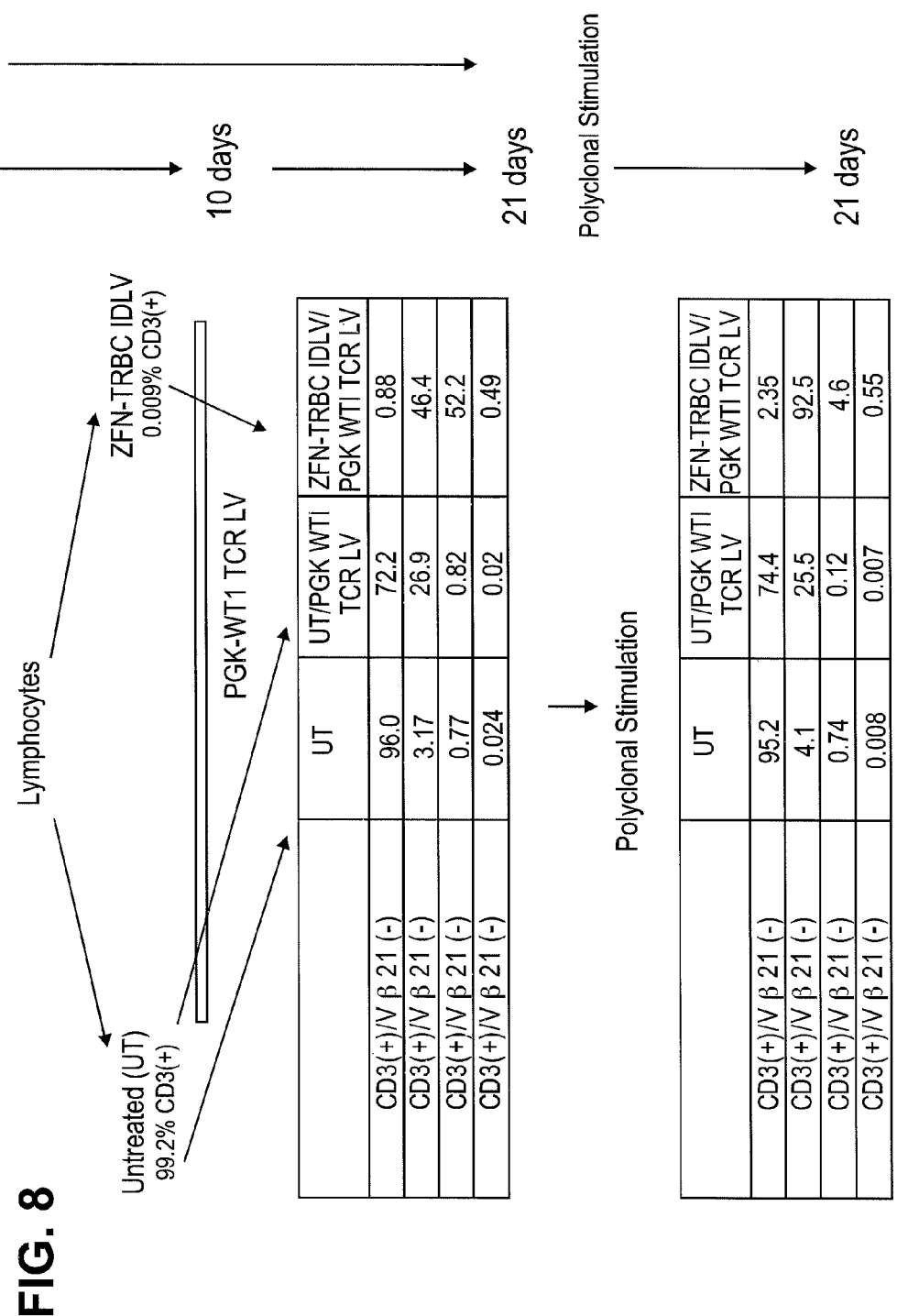
FIG. 8 depicts the experimental outline and the FACS results for editing of the TCR-β locus in primary T lymphocytes and the re-introduction of a specific TCR transgene. Cells used were either untreated primary T cells lymphocytes or lymphocytes pre-treated with the TCR-β-specific ZFNs carried by an IDLV and then sorted for CD3(−) primary T cells. Gene transfer was achieved after stimulation of T cells with cell-sized beads coated with antibodies directed to CD3 and to CD28, and cell culture in the presence of IL7 (5 ng/ml) and IL15 (5 ng/ml) to facilitate the generation of genetically modified central memory lymphocytes, according to European Patent Publication No EP1956080. As shown, cells that were sorted for being CD3(−) after treatment with the TCR-β specific ZFNs and then have the WT1-TCRβ V21.3 and WT1.TCRα transgenes randomly integrated into the genome using a lentiviral vector, show an increase in staining for both CD3 and for Vβ21.3, indicating primary T lymphocytes can undergo endogenous TCR disruption via NHEJ using the TCR-β-specific ZFNs and then be re-targeted to recognize a specific antigen via the introduction of a new TCR encoded by a transgene cassette (PGK-WT1). As a control, UT cells also had the PGK-WT1 cassette inserted and showed a smaller percentage of cells expressing Vβ 21.3 (26%) as compared to the ZFN-treated, CD3(−) population (46%, 92% after polyclonal stimulation), indicating the disruption of the endogenous TCR may improve the cell-surface expression and functionality of the TCR expressed from the transgene.

In contrast to unedited TCR-transferred lymphocytes in which there was no inherent growth advantage to expression of the introduced TCR (FIG. 8, $2^{nd}$ row) with respect to the untransduced cells on polyclonal expansion, TCR β chain disrupted cells containing the WT1-TCR could be enriched to >90% purity by polyclonal stimulation, indicating that surface expression of the transferred TCR/CD3 complex in TCR-β-edited cells was necessary and sufficient to promote TCR-mediated expansion of genetically modified cells (FIG. 8, $1^{st}$ row). The exogenous WT1-TCR Vβ chain (Vβ21) was expressed in TCR-β chain disrupted lymphocytes at approximately 2-fold higher mean levels than in unedited TCR-transferred cells and reached expression levels similar to those of the endogenous Vβ21 chain of control T cells and was stably maintained in culture (FIG. 9A and FIG. 9B). Accordingly, after transduction with the same dose of PGK-WT1 LV, up to 22% of TCR-β-edited lymphocytes bound the WT1$_{126-134}$ pentamer as compared to only 2.6% of unedited cells. (FIG. 9A, lower histogram).

Thus, in the absence of competition from the endogenous TCR β chain, surface expression of the transgenic TCR β chain reaches physiological levels. To verify the function and avidity of TCR-β-edited lymphocytes, we compared TCR β chain disrupted cells with unedited cells transduced with the same PGK-WT1 LV for the ability to lyse HLA-A2$^+$ targets pulsed with increasing WT1$_{126-434}$ peptide concentrations (see FIG. 9C). This functional assay measures activity by a $^{51}$Chromium release assay for lysis of labeled T2 cells pulsed with increasing concentrations of the WT1$_{126-134}$HLA-A2 restricted peptide, or with the irrelevant CMV-derived pp65$_{494-503}$ HLA-A2 restricted peptide (10 µM, Proimmune) as a negative control, at an Effector/Target (E/T) ratio of 12.

Edited T cells were stimulated and 3 weeks later were tested for recognition of the labeled T2 cells by co-incubation for 5 hours. TCR β chain disrupted cells (denoted TCR-edited in FIG. 9C) killed targets more effectively than unedited (denoted TCR-transferred) WT1 LV transduced cells (EC50: edited cells: 90.51 nM, with 95% CI: 48.84-167.7; unedited TCR-transferred cells: 269.1 nM, with 95% CI: 175.1-413.5), likely reflecting the higher frequency and expression level of the transgenic WT1 TCR in the TCR-β edited samples. EC50 was calculated by non-linear regression analysis of $^{51}$Chromium release data by using the sigmoidal dose-response equation of the GraphPad Prism Software.

Results are represented as average SD of % lysis (*=p<0.05, **=p<0.01, TCR-edited n=6, TCR transferred, n=4). To assess reactivity at a single cell level, cell were analyzed for Vβ21 expression (see Table 11 below) which showed that, despite fairly equal copy number of the vectors, Vβ21 expression was greater in the TCR-edited cells.

TABLE 11

TCR expression and vector copy number/cell in TCR transferred and TCR edited lymphocytes

| | Disruption endogenous β chain by TRBC-ZFN | PGK-WT1 LV or EF1α-WT1 LV | Vβ21 RFI* | % Vβ21+ cells | CpC§ |
|---|---|---|---|---|---|
| TCR-transferred | No | EF1α-WT1 LV | 0.41 | 36.7 | 1.9 |
| | | PGK-WT1 LV | 0.54 | 62.7 | 2.1 |
| TCR-edited | Yes | PGK-WT1 LV | 0.91 | 97.3 | 1.2 |
| UT | No | None | 1 | 3.2 | 0 |

*TCR expression was measured by flow cytometry and was plotted as relative fluorescence intensity (RFI = Vβ21 MFI of transduced cells/Vβ MFI of untransduced cells).
§Vector copy per cell (CpC) was measured by quantitative PCR as described (Kessels et al, (2001) *Nature Immunol* 2 (10): 957-61).

To assess alloreactivity at a single cell level, clones were isolated and expanded from both TCR-β edited and TCR-transferred cells, previously sorted for WT1$_{126-134}$ pentamer binding to enrich for cells displaying optimal exogenous TCR expression. Clones were exposed to T2 cells pulsed with 10 nM of the WT1$_{125-134}$ HLA-A2 restricted peptide (left panel) or to allogenic PRMC (right panel) at a stimulator/responder ratio of 1. The number of specific spots is shown on the y axis as the number of spots produced in the presence of stimulators minus the number of spots produced by effectors alone (**=p<0.01). TCR β-edited clones displayed reduced alloreactivity, compared to TCR-transferred cells (see FIG. 10, compare the 10A to 10B), possibly reflecting the reduced risk of TCR mispairing in the absence of one endogenous TCR chain.

These data demonstrate the functional advantage offered by expression of a tumor specific exogenous TCR in a host CTL with abrogated endogenous TCR-β chain expression.

Figure 11:
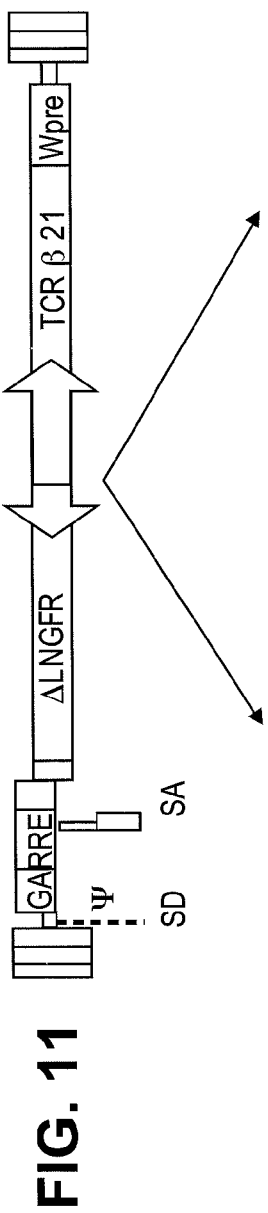
FIG. 11 depicts Vβ21 expression in ZFN-edited and unedited cells. CD3(−) cells sorted from TRBC-disrupted lymphocytes and unedited cells and were transduced at increasing MOI by LV encoding the Vβ21 gene of the WT1-specific TCR and the ΔLNGFR gene (see diagram at the top of figure showing dual expression of the Vβ21 gene and the ΔLNGFR gene). Transduction efficiency was assessed as % of $ΔLNGFRP^{pos}$ lymphocytes and is shown. Vβ21 expression was measured on $ΔLNGFRP^{pos}$ cells and demonstrates that the transduced Vβ21 gene can be expressed and form active CD3 complexes with the endogenous TCR α chain. The mean fluorescence intensity (MFI) of Vβ21 is shown.

Theoretically, surface re-expression of the unedited endogenous TCR α chain may still occur in TCR-β edited cells, following TCR gene transfer. To directly assess the potential for mispairing in TCR-β chain disrupted lymphocytes, CD3(-) cells were transduced with a LV encoding only the WT1-specific TCR β chain gene and the ΔLNGFR marker (WT1-β-ΔLNGFR-LV). Transduction efficiency was assessed as a percentage of the ΔLNGFR$^{pos}$ lymphocytes (see FIG. 11). Vβ21 expression was measured on ΔLNGFR$^{pos}$ cells. The mean fluorescent intensity (MFI) of Vβ21 is indicated. Despite the absence of WT1-specific α chain, Vβ21 expression was detected in up to 83% of ΔLNGFR$^{pos}$ TRBC-disrupted cells, demonstrating that even a cysteine-modified TCR β chain inserted into a cell with a TRBC disruption is capable of mispairing with the endogenous TCR α chain.

Next, CD3(-) lymphocytes are used to introduce the WT1-TCR β donor construct into the endogenous TCR locus. The donor is constructed as described above and used in conjunction with the TCR-β-specific ZFNs to cause integration of the TCR-β transgene at the endogenous locus. The cells become positive for both CD3 and the Vβ 21.3 TCR β chain.

Example 8

Disruption and Targeted Integration of the TCR-α Chain

Figure 12A:
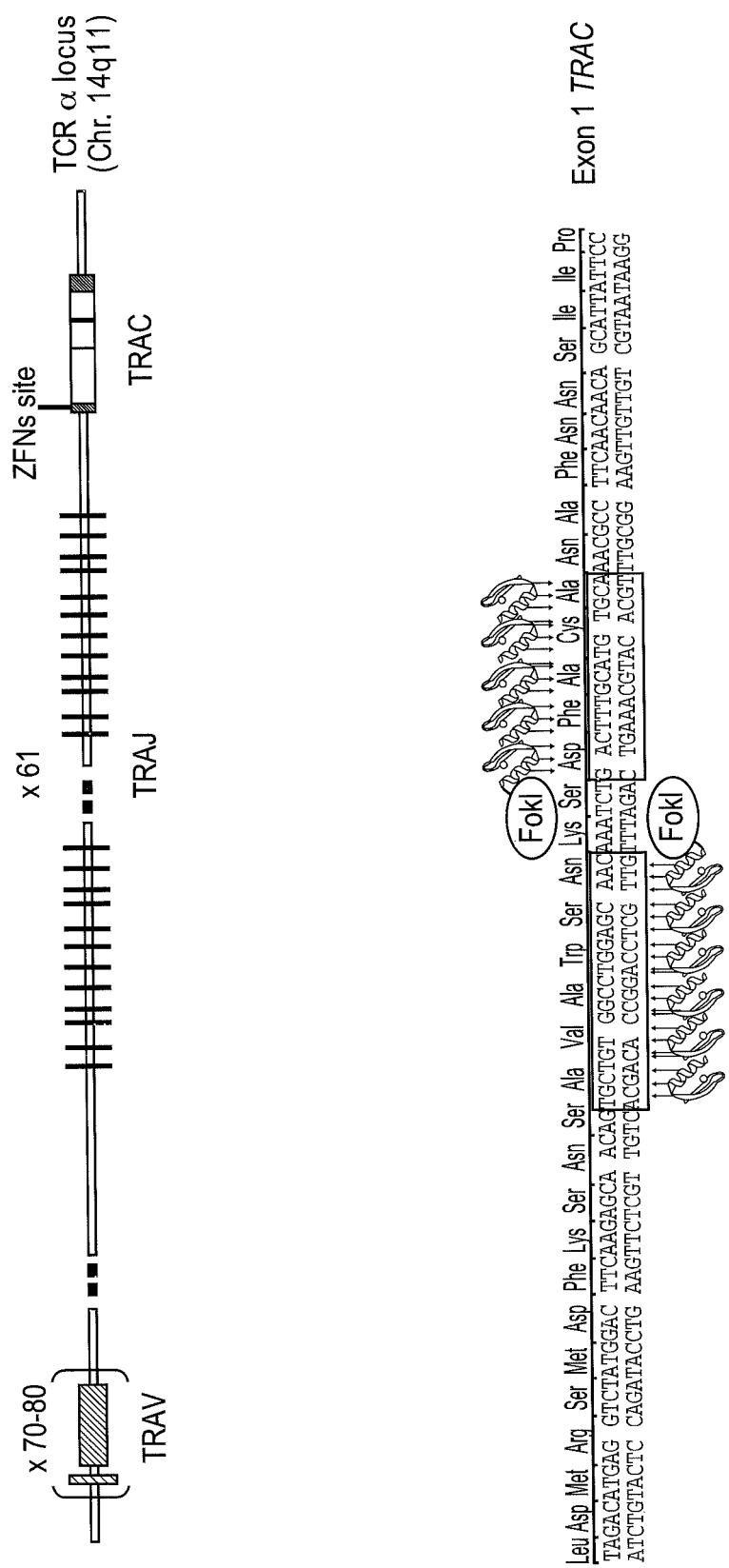
FIG. 12A depicts a diagram of the human locus encoding the TCR α, total length 18 kb; TRAV, variable region genes, TRAD, diversity region genes, TRAC, constant region gene. Displayed above the scheme of the locus are the genomic DNA sequences in TRAC targeted by each TRAC-ZFN.
Figures 12B, 12C:
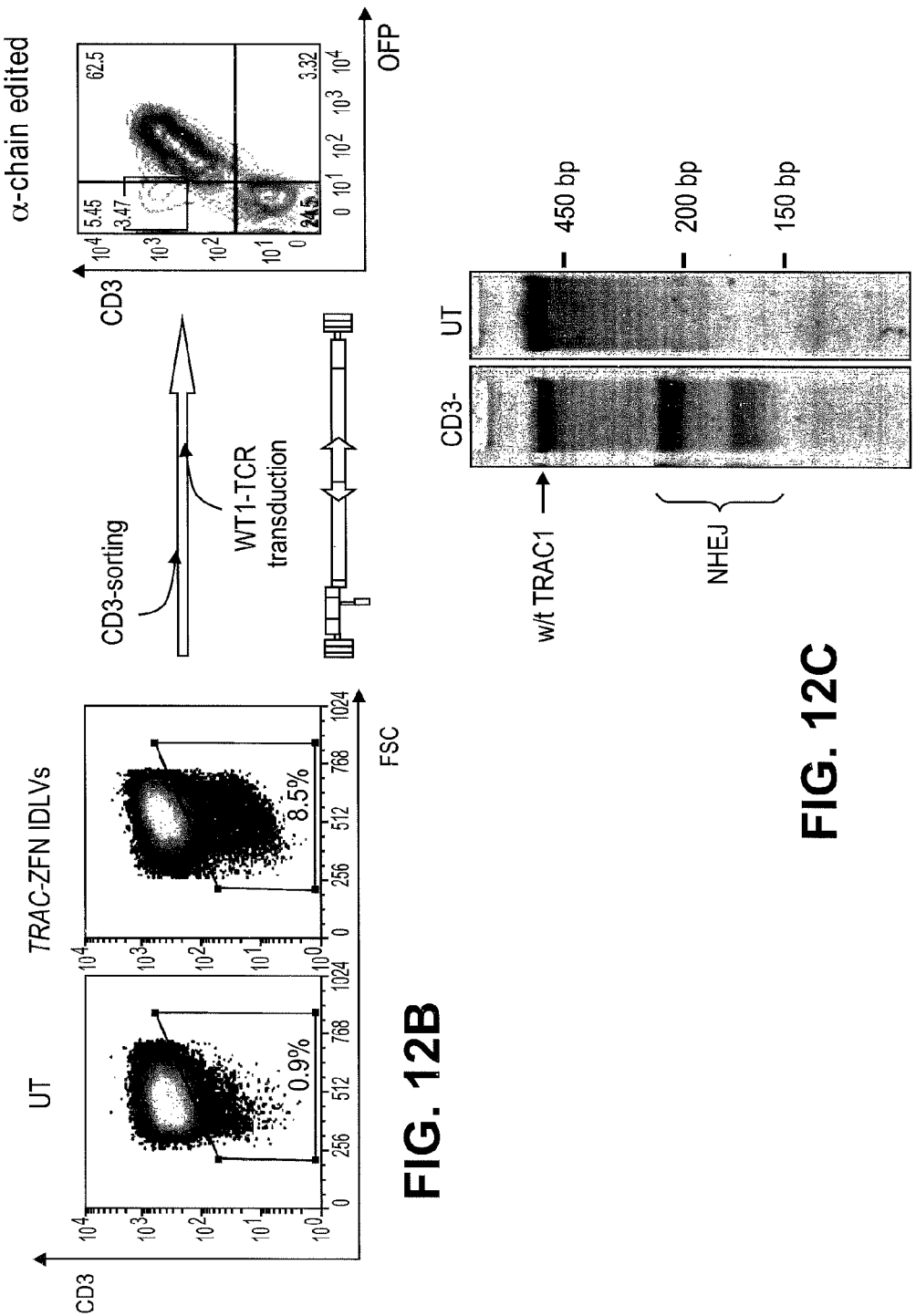
FIG. 12B depicts down-regulation of cell surface CD3 expression measured by flow cytometry in primary human lymphocytes stimulated with baCD3/CD28, cultured with 5 ng/ml IL-7, 5 ng/ml IL-15, and exposed to TRAC-ZFN IDLVs. The percent of CD3(−) cells is plotted. UT, Untransduced cells. Sorted CD3(−) cells were transduced with WT1-α OFP-LV resulting in expression of CD3 on transduced lymphocytes.
FIG. 12C depicts a gel showing the level of targeted gene disruption measured by the Cel-I assay in primary lymphocytes exposed to TRAC-ZFN. The higher migrating product indicating wild type (w/t) gene is shown. Lower migrating products (NHEJ) indicate ZFN-directed gene disruption. "UT" refers to untransduced cells.
Figure 13:
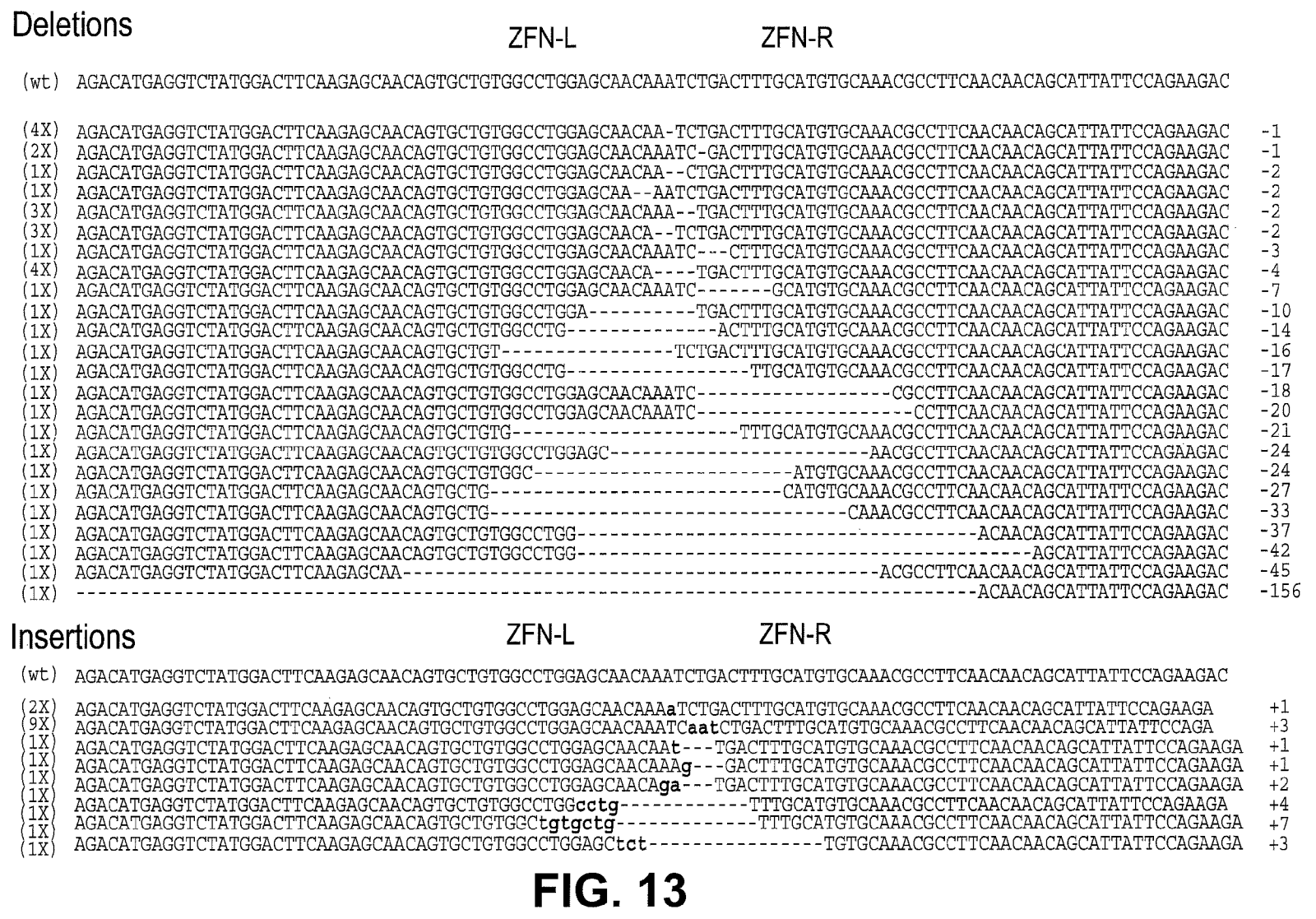

To eliminate the potential for TCR chain mispairing, we designed a pair of ZFNs targeting the constant region of the TCR α chain (TRAC) gene (FIG. 6) and obtained TCR-α-edited T lymphocytes (see FIG. 12A), following the same protocol described to TCR-β editing) and obtained TCR-α-edited T lymphocytes, following the same protocol described for TCR-β-editing (FIG. 12B, 12C, 13). To design a complete α/β TCR editing protocol that permits rapid isolation of engineered cells at each step of chain disruption/replacement, we generated a set of LV carrying a single α or β WT1-specific TCR chain, and used IDLV or adenoviral vectors (AdV) to transiently express TRBC- or TRAC-targeting ZFNs in lymphocytes (FIG. 14 for timeline and representative flow conditions/results for full TCR editing)

CD3(-) cells were efficiently generated with every ZFN-containing vector tested and sequencing at the site of nuclease cleavage reveals the small insertions and deletions (indels) present after repair by NHEJ (FIG. 13). AdVs, which proved more efficient in mediating TCR gene disruption than IDLVs, were selected for the purpose of complete TCR editing. T cells harvested from healthy donors were first exposed to TRAC-ZFN-Ad5/F35 48 hrs post-activation with baCD3/CD28, cultured in the presence of IL-7 and IL-15, and the resulting CD3(-) cells isolated by sorting were transduced (49±29& mean±SD transduction frequency, n=3) with a LV encoding the WT1-α chain (WT1-α LV).

Figure 14:
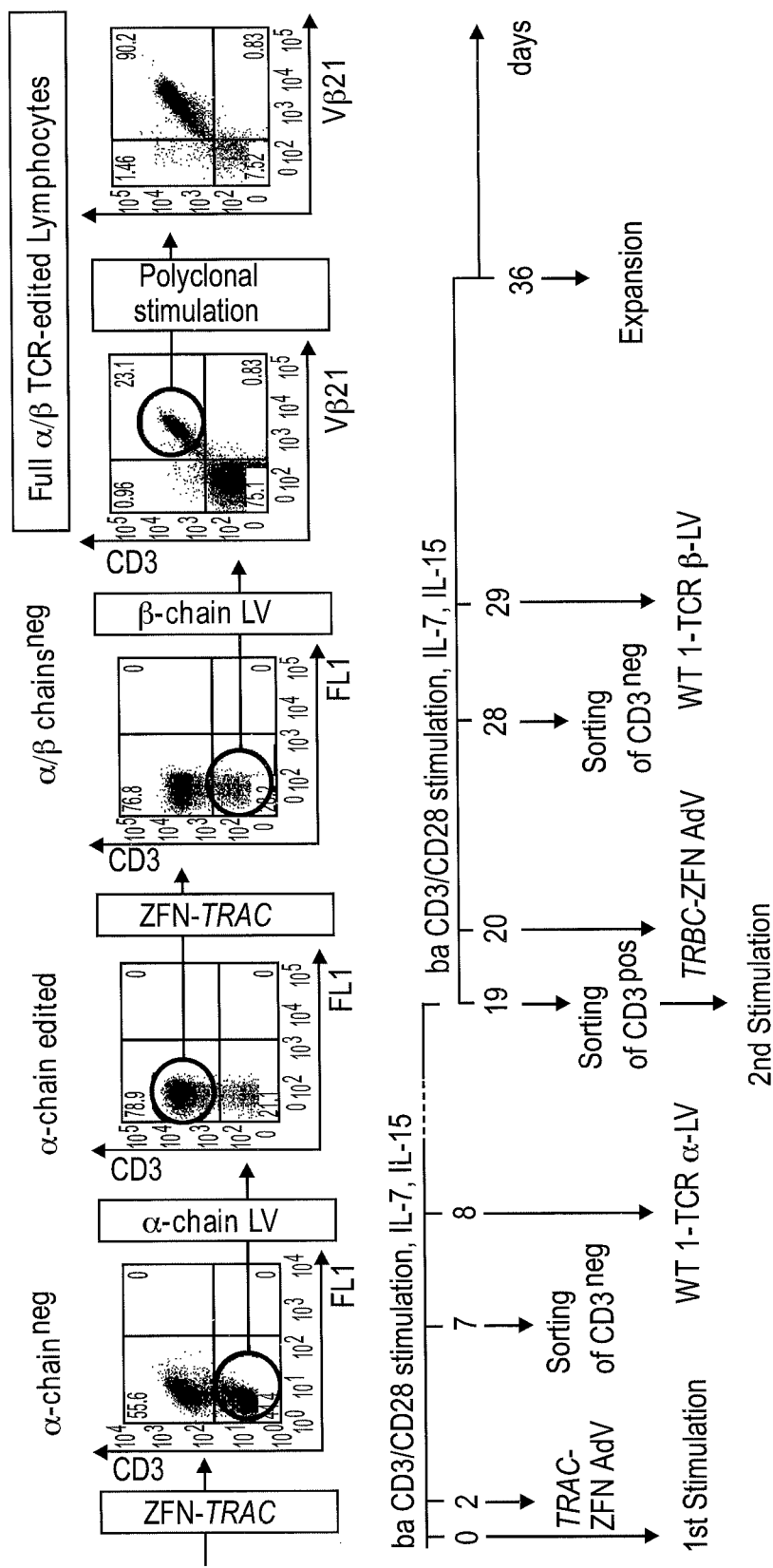
FIG. 14 depicts expression of CD3 in following ZFN editing. Upper panels shows results of studies in which activated T lymphocytes were treated with TRAC-ZFN-AdV (MOI 1000), and CD3(−) lymphocytes were sorted and transduced with 3 μg-p24/$10^6$ cells of PGK-WT1-α LV and CD3(+) cells were sorted. Surface expression of CD3 in transduced cells is shown. After one cycle of polyclonal stimulation, α-edited lymphocytes were treated with TRBC-ZFN-AdV (MOI $10^4$) and CD3(−) cells sorted and transduced with 3 μg-p24/$10^6$ cells of PGK-WT1-β LV. Surface expression of Vβ21 TCR and CD3 is shown on transduced cells before and after one cycle of polyclonal stimulation. Percent of events measured in each quadrant are shown, and the experimental timeline is shown on the bottom.
Figure 15:
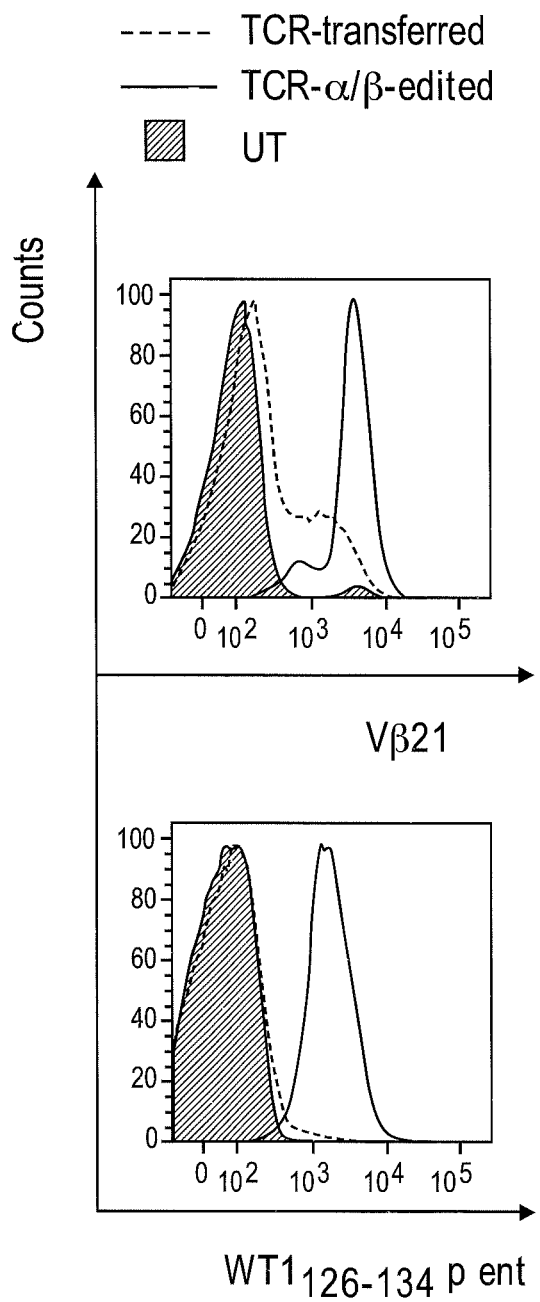
FIG. 15 depicts Vβ21 TCR expression (upper histogram) and $WT1_{126-134}$ pentamer binding (lower histogram) are shown in CD8(+) T cells with TCR α/β chains disrupted via introduction of ZFNs and sorting for CD3− cells followed by transduction with the WT1 TCR chains and sorting for CD3+ cells (TCR-edited), unedited WT1 LV transduced cells (TCR-transferred), and untransduced lymphocytes treated with the same culture conditions. The data show that the TCR edited cells have a higher level of Vβ21 expression than those clones wherein both the endogenous and the exogenous TCR genes are present. It also demonstrates that the TCR edited cells display higher binding to the WT1 peptide than those cells that have both sets of TCR genes.

Cells with rescued CD3 expression were then sorted, stimulated with baCD3/CD28 for one cycle, and then exposed to TRBC-ZFN-Ad5/F35. The second round of ZFN exposure yielded up to 23±4% newly CD3(-) cells, indicating that primary T lymphocytes are permissive to multiple rounds of ZFN manipulation. The CD3(-) cells were sorted and transduced (18±7% mean±SD transduction efficiency, n=3) with a WT1 TCR-β chain LV. Expression of the transferred WT1-β chain again rescued surface translocation of CD3, which was now co-expressed in balanced proportion with the WT1-TCR Vβ chain in TCR-edited cells (FIG. 14 and FIG. 15). In contrast to unedited TCR-transferred lymphocytes, TCR-α/β disrupted cells could be enriched to near purity by polyclonal stimulation following TCR gene transfer, and homogenously expressed the high levels of WT1-specific TCR required to bind the WT1$_{126-434}$ pentamer (see FIG. 15).

These results indicate that surface expression of the transferred TCR/CD3 complex in TCR-edited cells was necessary and sufficient to promote expansion of the cells with the desired specificity for WT1 (FIG. 14, right plot). Disruption of the α and β TCR chains was confirmed in TCR-α/β edited cells by Cel-I analysis. No phenotypic differences were observed in TCR-transferred and TCR α/β-edited lymphocytes, which displayed a $T_{CM}$ surface phenotype, as evidenced by high expression of CD62L, CD27, CD28 and IL-7rα. To verify the function and allogenic response of the fully edited lymphocytes, TCR α/β-edited and TCR transferred lymphocytes were polyclonally stimulated.

Figure 16A:
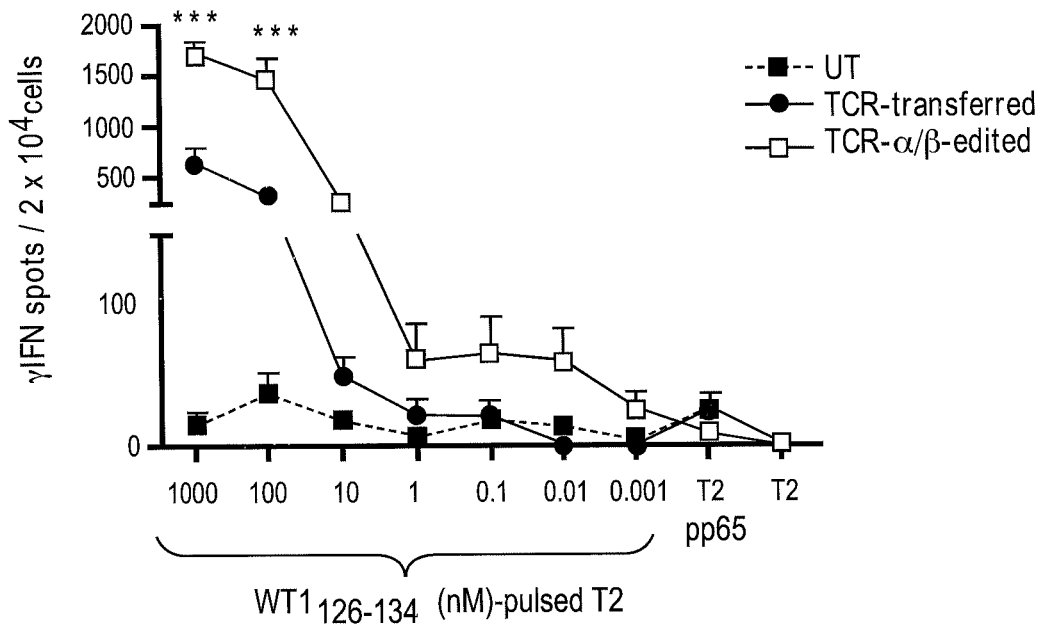
FIG. 16, panels A to C, are graphs depicting functional activity of genetically modified lymphocytes was tested by the γIFN ELISpot assay. Three weeks after polyclonal stimulation, TCR-α/β-edited and TCR transferred lymphocytes were exposed to either i) T2 cells pulsed with increasing concentrations of the $WT1_{126-134}$ HLA-A2 restricted peptide, or with the irrelevant CMV-derived $pp65_{495-503}$ HLA-A2 peptide (see FIG. 16A, right side of figure) or ii) $WT1^+$ HLA-A2(+) (black in FIG. 16B) or HLA-A2(−) (grey) leukemic cells harvested from AML patients with (dashed symbols) or without (full symbols) pulsing with WT1$_{126-134}$ peptide (50 nM).
FIG. 16C shows similar results where allogenic PBMC were used as target. All assays were performed at a stimulator/responder ratio of 1:1. The number of specific spots is shown on the y axis as the number of spots produced in the presence of stimulators minus the number of spots produced by effectors alone. *=p<0.05, =p<0.01, *=p<0.001.
Figure 16B:
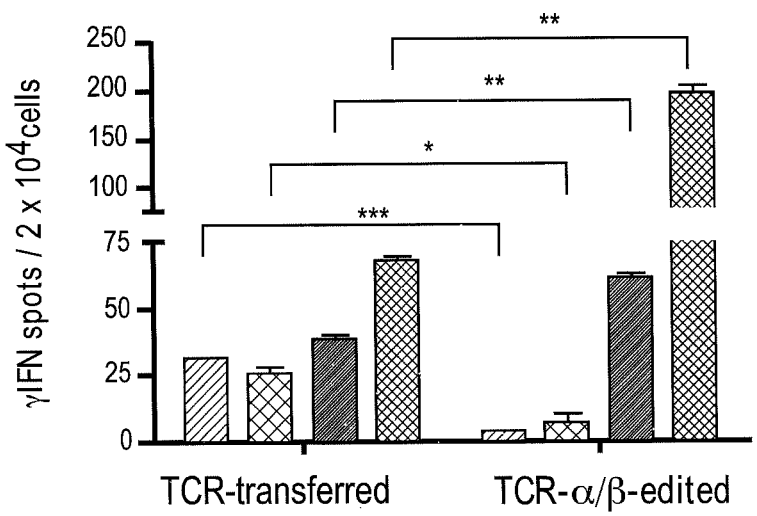
Figure 16C:
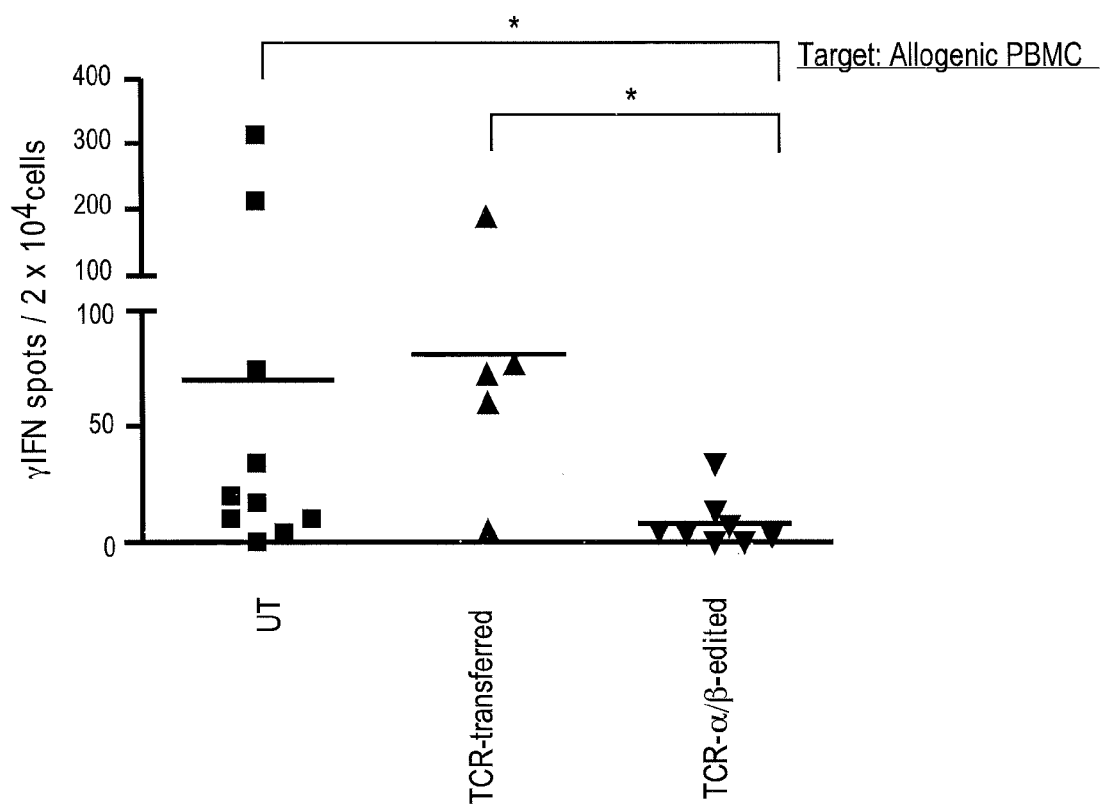

Three weeks after polyclonal stimulation, TCR-α/β-edited and TCR transferred lymphocytes were exposed to either i) T2 cells pulsed with increasing concentrations of the WT1$_{126-134}$ HLA-A2 restricted peptide, or with the irrelevant CMV-derived pp65$_{495-503}$ HLA-A2 peptide (see FIG. 16A) or ii) WT1$^+$ HLA-A2$^+$ (black in FIG. 16B) or HLA-A2$^-$ (grey) leukemic cells harvested from AML patients with (dashed symbols) or without (full symbols) pulsing with WT1$_{126-134}$ peptide (50 nM). FIG. 16C shows similar results where allogenic PBMC were used as target. All assays were performed at a stimulator/responder ratio of 1. Specific spots are shown on the y axis as spots produced in presence of stimulators minus spots produced by effectors alone. *=p<0.05, =p<0.01, *=p<0.001.

Example 9

Potential Off Target Cleavage Analysis

In silico analysis was used to identify the most likely potential off-target cleavage sites for both the TRAC- and TRBC-specific ZFN pairs as described in Perez et at (ibid). Sites were identified that contained up to 10 recognition site mismatches for either heterodimer ZFN pairs or homodimer pairs, although the most likely potential off target sites for these ZFN pairs were all targets for ZFN homodimers. The most likely potential off target sites identified are shown below in Tables 12 (TRAC) and 13 (TRBC).

TABLE 12

Potential off target sites for TRAC-specific ZFNs

| Label | Chromosome | Start site | Sequence | # mismatches | Gene |
|---|---|---|---|---|---|
| OT1 | 20 | 20683361 | AGGCACAaGCAAtGTCAC AAGtACcaTGCtTGTACTT (SEQ ID NO: 76) | 6 | RALGAPA2 |
| OT2 | 6 | 10525974 | AGGTACAaGtAAAGaCGT ATGaACTTTGCtTGTACTT (SEQ ID NO: 77) | 5 | GCNT2 |
| OT3 | X | 135000000 | AAaTACAaGCcAAGcCAA GGTGgCTTTGCGTGTAaA T (SEQ ID NO: 78) | 6 | — |
| OT4 | 18 | 60239118 | ATaTACAattAAAGTCAGC TTTtACTTTGCagtTACTT (SEQ ID NO: 79) | 8 | ZCCHC2 |
| OT5 | 7 | 48500931 | TAGaACAtcCAAAcTCTGG ACCGACTTTGCaTGTcCA G (SEQ ID NO: 80) | 6 | ABCA13 |
| OT6 | 7 | 141000000 | ATtCAaACaCAAAGTCCCG TGGAtTTTGCtTtTAaAT (SEQ ID NO: 81) | 7 | — |
| OT7 | 8 | 2463159 | ATGCAggaGCAAgGTCAC TCTGACcTTcCtTtgcCTT (SEQ ID NO: 82) | 10 | — |
| OT8 | 18 | 4312947 | ATGCACACaCAAAcTCAT TTAagCTTTGCtTtTcCAT (SEQ ID NO: 83) | 7 | — |
| OT9 | 11 | 70854569 | CAGCcCAtGgAAtGTCATT CTcACaTTGCtTGTGCTT (SEQ ID NO: 84) | 7 | SHANK2 |
| OT10 | 13 | 57970961 | AAGCAaAaGaAAAaTCAA TATGACTTgGCtTtgGCTT (SEQ ID NO: 85) | 8 | — |
| OT11 | 2 | 69188623 | AAGgtCACtCActGTCTGTG TGGAgTTTGCGTGTcCTC (SEQ ID NO: 86) | 7 | — |

TABLE 12-continued

Potential off target sites for TRAC-specific ZFNs

| Label | Chromosome | Start site | Sequence | # mismatches | Gene |
|---|---|---|---|---|---|
| OT12 | X | 78538296 | AAGCAggaGCAAAGTCAC ATCTtACaTTGCGgcgGCA T (SEQ ID NO: 87) | 8 | — |
| OT13 | 2 | 108000000 | ATGTAattcCAAAGTCCTC CATGACcTgGCtTcTACCT (SEQ ID NO: 88) | 8 | — |
| OT14 | 8 | 28249779 | CTaCAaAttCAAtGaCAGTA GAGACTTTGCtTtTACTT (SEQ ID NO: 89) | 8 | — |
| OT15 | 9 | 93810846 | ATGCAacaGCAAgagCAGC ATGACTTTGttTtTcCTT (SEQ ID NO: 90) | 10 | — |
| TRAC | 14 | 23016627 | GTGCTGTgGCCTGGaGcA ACAAATCTGACTTTGCaT GTGCAA (SEQ ID NO: 91) | 4 | TRAC |

TABLE 13

Potential off target sites for TRBC-specific ZFNs

| Label | chromosome | Start site | Sequence | # mismatches | Gene |
|---|---|---|---|---|---|
| C1 | 1 | 236659757 | CCcAagCCAGggCTACTGCT GGGTgGAACTGGACATGC (SEQ ID NO: 92) | 6 | — |
| C10 | 10 | 90573967 | CCcTGTgCgGTTCTgCTTAA CAGTAGAACaGGACActT (SEQ ID NO: 93) | 7 | LIPM |
| C5 | 5 | 165037707 | ACATGTCagaTTCTACATG AGGTAGAACTGttCTTGT (SEQ ID NO: 94) | 5 | — |
| C2 | 2 | 71186796 | ACAAGggCAGcTCTgtCCA AGGTAGcACTGGgCCTGT (SEQ ID NO: 95) | 7 | ATP6V1B1 |
| C15 | 15 | 75401377 | CgATGTCCAGaTgTACCTC AGGaAGgACTGGcCCTGG (SEQ ID NO: 96) | 6 | — |
| C3 | 3 | 159730398 | CCAAGTCCtccTCTAgGAA GGGGTAGAACTGGAaTTtG (SEQ ID NO: 97) | 6 | — |
| C1.2 | 1 | 60766812 | GaAGGTCCAGTgCAAtGTT GAaTAGAAgTGGACATcT (SEQ ID NO: 98) | 7 | — |
| C17 | 17 | 11136639 | AgAGGcCCAcTcCTAgAAG GGGTAGAcCTGGAtCTGG (SEQ ID NO: 99) | 7 | — |
| C15.2 | 15 | 67440002 | CCAGGTCCAGTTCTACCA GCCacAGAtgTGagCATGT (SEQ ID NO: 100) | 6 | SMAD3 |
| C2.2 | 2 | 120313989 | ACAAtTCCAGTTCaAgAAT CTTtTAaAggTGGACATGG (SEQ ID NO: 101) | 7 | PCDP1 |
| C6 | 6 | 166419926 | GCtGGTgCAGcTCTACACG GATGcAGAgCTGGtCCTcC (SEQ ID NO: 102) | 7 | — |

TABLE 13-continued

Potential off target sites for TRBC-specific ZFNs

| Label | chromosome | Start site | Sequence | # mismatches | Gene |
|---|---|---|---|---|---|
| C2.3 | 2 | 114733178 | CCtGGgCCAGTgCTgCTTGT CcTtGAACcGGgCCTGG (SEQ ID NO: 103) | 8 | — |
| C7.2 | 7 | 4224762 | GgAGaTCCAGTgCgACAGT CAGaAGAAggGGACTcGG (SEQ ID NO: 104) | 8 | SDK1 |
| CX | X | 73070675 | CTaCAaAttCAAtGaCAGTA GAGACTTTGCtTtTACTT (SEQ ID NO: 105) | 8 | XIST |
| CX.2 | X | 130414175 | CCAGGTCagGTTCCggAAA GAAGTAGAACTtGACCccT (SEQ ID NO: 106) | 8 | AGSF1 |
| TRBC | 7 | 142499011 | TCAAGTCCAGTTCTACGG GCTCtCGGAGaATGACGA GTGGA (SEQ ID NO: 107) | 2 | TRBC |

Figure 17:
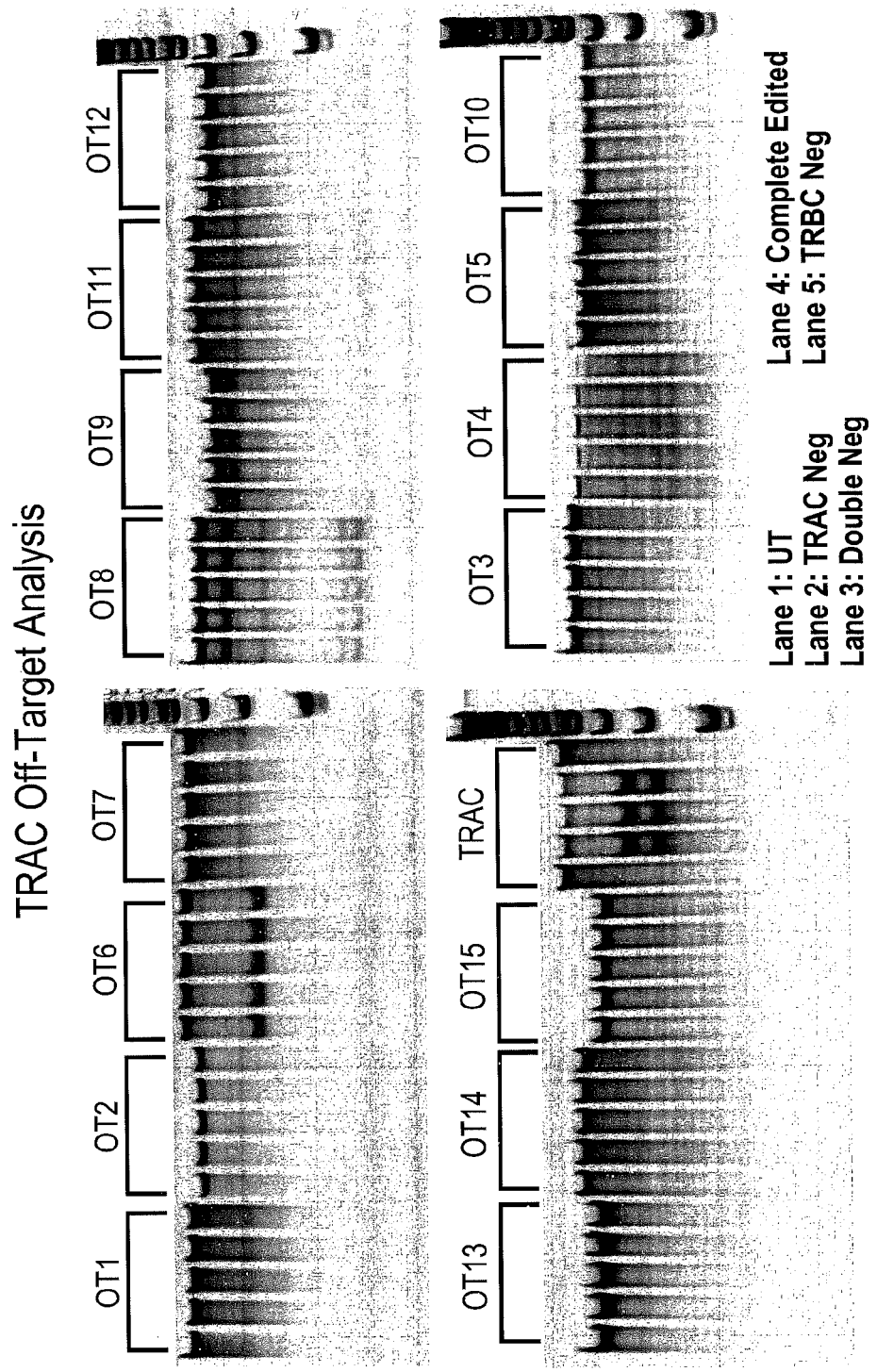
FIG. 17 depicts analysis for off-target cleavage by TRAC-specific ZFNs. The 15 most likely potential off target sites for the TRAC-specific ZFNs (identified by in silicio analysis) were analyzed following ZFN treatment for cleavage by the Cel-I mismatch assay. Each potential off target site was analyzed in 5 samples: untransduced samples (UT), samples that were TRAC negative following TRAC-specific ZFN treatment and sorting (TRAC neg), cells that were TRAC and TRBC negative following sequential treatment with TRAC-specific ZFNs, the TRAC transgene and TRBC-specific ZFNs with sequential rounds of sorting (Double Neg), cells that were negative for the endogenous TRAC and TRBC loci following ZFN treatment as well as modified to comprise non-wild type TRAC and TRBC transgenes (Complete Edited), or TRBC negative following treatment with TRBC-specific ZFNs alone and sorting (TRBC Neg). Potential off target sites are as labeled in Table 12.
Figure 18:
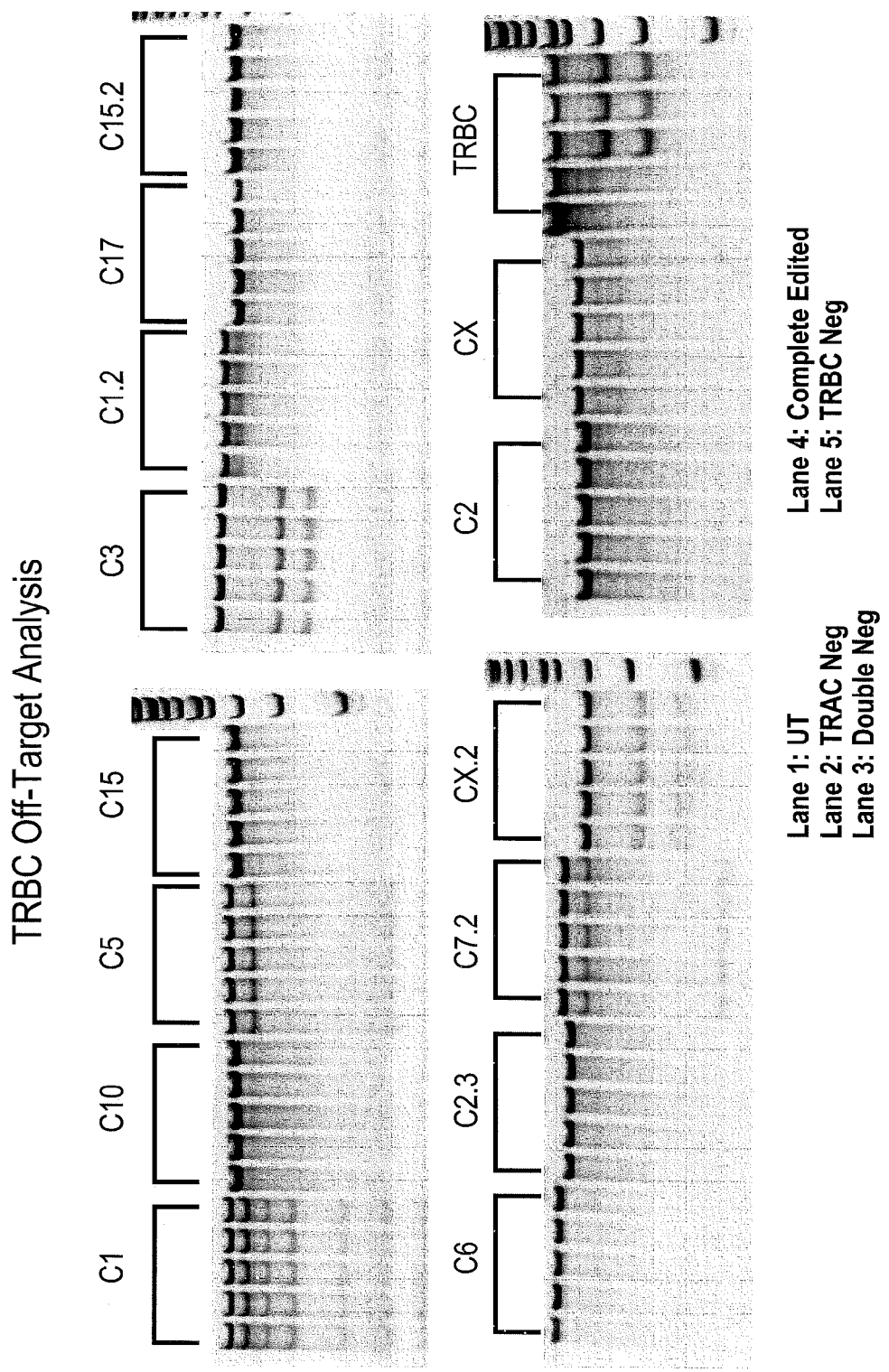
FIG. 18 depicts analysis for off-target cleavage by TRBC-specific ZFNs. 15 potential off target sites for the TRBC-specific ZNS (identified by in silico analysis) were analyzed following ZFN treatment for cleavage by the Cel-I mismatch assay. Each potential off target site was analyzed in 5 samples: untransduced samples (UT), samples that were TRAC negative following TRAC-specific ZFN treatment and sorting (TRAC neg), cells that were TRAC and TRBC negative following sequential treatment with TRAC-specific ZFNs, the TRAC transgene and TRBC-specific ZFNs with sequential rounds of sorting (Double Neg), cells that were negative for the endogenous TRAC and TRBC loci following ZFN treatment as well as modified to comprise non-wild type TRAC and TRBC transgenes (Complete Edited), or TRBC negative following treatment with TRBC-specific ZFNs alone and sorting (TRBC Neg). Off target sites are as labeled in Table 13. TRBC depicts modification of the intended target site in these samples.

As shown in FIGS. 17 and 18, there are no additional bands present in the off-site samples that have been treated with the ZFNs as compared to those that have not been transduced with the ZFN expression vectors (also compare with the TRAC and TRBC loci). Thus, it appears that the TRAC- and TRBC-specific ZFNs are specific for their intended targets.

Example 10

TRAC and TRBC-specific TALENs

TRAC- and TRBC-specific TALENs were developed and assembled essentially as described in U.S. Pat. No. 8,586,526. Base recognition was achieved using the canonical RVD-base correspondences (the "TALE code": NI for A, HD for C, NN for G (NK in half repeat), NG for T). The TALENs were constructed in the "+63" C-cap (C-terminal truncation) of the TAL-effector DNA-binding domain within the TALEN backbone as described in U.S. Pat. No. 8,586,526. The targets and numeric identifiers for the TALENs tested are shown below in Table 14.

TABLE 14

TRAC and TRBC-specific TALENs

| SBS # | Site (5'-3') | # of RVDs | SEQ ID NO (target site): | TRAC/TRBC |
|---|---|---|---|---|
| 101511 | gtGCTGTGGCCTGGAGCaa | 15 | 144 | TRAC |
| 101512 | gtGCTGTGGCCTGGAGCAac | 16 | 145 | TRAC |
| 101513 | ctGTGGCCTGGAGCAACaa | 15 | 146 | TRAC |
| 101514 | ttGAAGGCGTTTGCACATGca | 17 | 147 | TRAC |
| 101515 | gtTGAAGGCGTTTGCACATgc | 17 | 148 | TRAC |
| 101516 | gtTGAAGGCGTTTGCACAtg | 16 | 149 | TRAC |
| 101536 | ttCCGCTGTCAAGTCCAGTtc | 17 | 150 | TRBC |
| 101537 | ctGTCAAGTCCAGTTCta | 14 | 151 | TRBC |

TABLE 14-continued

TRAC and TRBC-specific TALENs

| SBS # | Site (5'-3') | # of RVDs | SEQ ID NO (target site): | TRAC/TRBC |
|---|---|---|---|---|
| 101539 | ctGGGTCCACTCGTCATTct | 16 | 152 | TRBC |
| 101540 | ctGGGTCCACTCGTCATtc | 15 | 153 | TRBC |
| 101541 | atCCTGGGTCCACTCGTCAtt | 17 | 154 | TRBC |

The TALENs were then tested in pairs in K562 cells for the ability to induce modifications at the endogenous TRAC and TRBC chromosomal targets, analyzed by the Cel-I assay as described above in Example 5. The results showed that nearly all protein pairs were active, and that the TALENs and ZFNs have activities that are in the same approximate range. Tables 15 and 16 show matrix comparisons of pairs of the TALENs in terms of % NHEJ detected by the Cel 1 assay.

TABLE 15

TRAC and TRBC- specific TALENs activity 16A- TRAC (% NHEJ)

|  | 101511 | 101512 | 101513 |
|---|---|---|---|
| 101514 | 3.4 | 5.3 | 5.9 |
| 101515 | 5.9 | 8.9 | 8.3 |
| 101516 | 5.3 | 12.0 | 16.4 |

TABLE 16

TRBC (% NHEJ)

|  | 101536 | 101537 |
|---|---|---|
| 101539 | 8.5 | 0.0 |
| 101540 | 9.9 | 9.6 |
| 101541 | 15.0 | 9.9 |

Example 11

NY-ESO-1 TCR Modified T Cells

T cells were modified with a NY-ESO-1 specific TCR Vβ3 (see, for example Robbins et at (2011) *J Clin Oncol* 29(7): 917-924) and expression of the engineered TCR was monitored. In this experiment, T lymphocytes were isolated from healthy volunteers and were activated with CD3 and CD28-antibody conjugated beads. The cells were then cultured in the presence of 5 ng/mL IL-7 and 5 ng/mL IL-15 according to the method in Kaneko et at (*Blood* (2009) 113(5) p. 1006) and in Bondanza et at (*Blood* (2011) 117(24) p. 6469). The cells were then treated in one of three ways: Group 1 was transduced with a third generation bi-directional lentiviral vector (see Amendola et at (2005) *Nat. Biotechnol* 23:108-116) comprising the NY-ESO1 specific, HLA-A2 restricted α and β TCR chains (TCR-PGK-NYESO1 LV) to generate TCR 'transferred' "TR" T cells. Group 2 was treated prior to LV transduction with adenvirus comprising ZFNs specific for TRAC (see Example 6, ZFNs 25539 and 25540), and then were sorted for loss of CD3 signal. $CD3^{neg}$ cells were then transduced with the TCR-PGK-NYESO1 LV vector to generate the "single edited" or "SE" population of cells. Group 3 were treated first with adenovirus comprising the TRAC ZFN pair 25539/25540 as above and sorted for CD3 signal. $CD3^{neg}$ cells were then transduced with a LV vector comprising the NY-ESO-1 TCR α chain and sorted again for CD3 signal. In this instance, $CD3^{pos}$ cells were then stimulated with the baCD3/CD28 beads and exposed to adenovirus comprising the TRBC ZFN pair 16787/16783 and cells were sorted for absence of surface translocation of CD3. $CD3^{neg}$ cells were then transduced with a LV vector comprising the NY-ESO-1 TCR β chain. Thus, Group 3 expressed uniquely the NY-ESO-1 specific TCR without any endogenous TCR complex and was termed the "complete edited" or "CE" population.

Figure 19A:
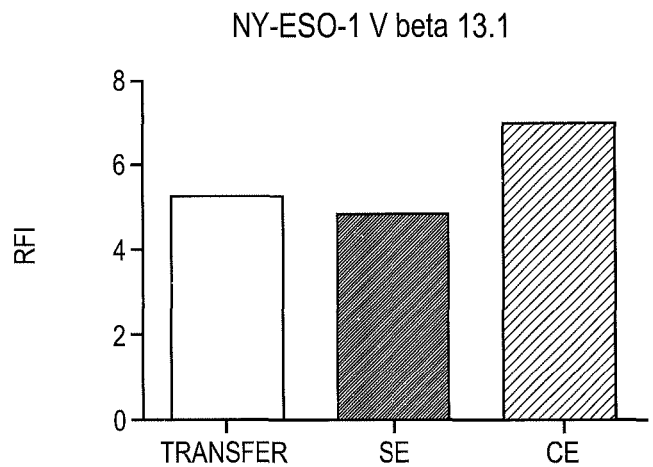
FIG. 19A shows a comparison of T cells transduced with the NY-ESO1 specific TCR ("Transfer") to cells that prior to TCR transduction, were first treated with TRAC-specific ZFNs to knock out the endogenous TCR-alpha chain ("SE") or cells that had both the TCR-alpha and the TCR-beta chains knocked out prior ("CE") prior to NY-ESO1 specific TCR transduction. Expression of the specific TCR is shown in the three T cell populations.

The three groups of cells were analyzed for expression of the exogenous V1313 TCR by a cytofluorimetric analysis where antibodies against NY-ESO-1 specific V beta 13.1 chain were used to label the protein. Untransduced T cells were used as control, and the data was expressed as the Mean Fluorescence Intensity (MFI) observed in the transduced T cells versus the controls. The complete edited population demonstrated the highest expression (see, FIG. 19A).

Figure 19B:
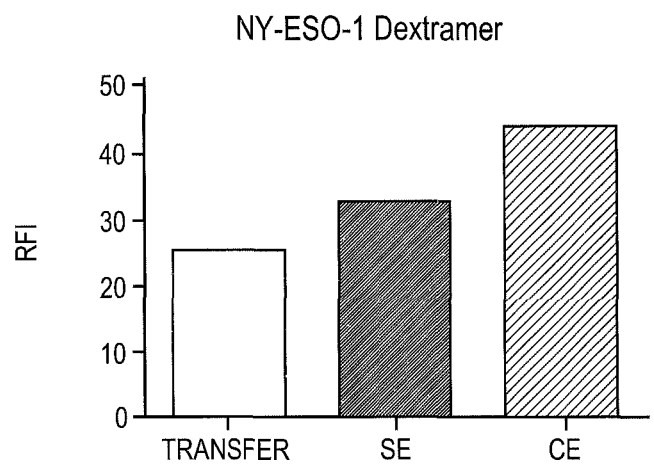
FIG. 19B shows the binding affinity for a dextramer comprised of NY-ESO1 peptides, and shows that the cell population that has had all the endogenous TCR chains deleted (CE) has the highest binding affinity of the T cell populations tested.
Figure 19C:
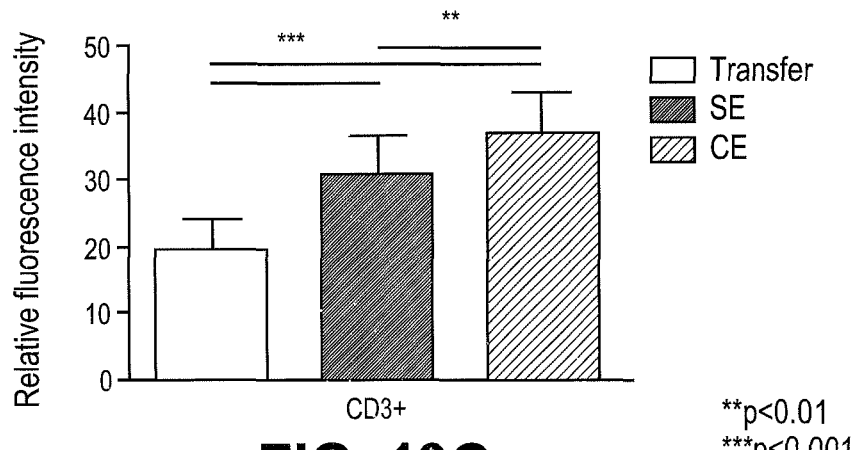
FIG. 19C is a graph depicting the average of 3 consecutive experiments from 3 different donors. The left most bar shows "Transfer" results, the middle bar shows "SE" results and the right most bar shows "CE" results.

The T cell populations were also tested for binding to a MHC HLA-A2-NY-ESO1 dextramer. The MHC Dextramer consists of a dextran polymer backbone carrying an optimized number of MHC and fluorochrome molecules. MHC Dextramer reagents carry more MHC molecules and more fluorochromes than conventional MHC multimers. This increases avidity for the specific T-cell and enhances staining intensity, thereby increasing resolution and the signal-to-noise ratio. For staining, the protocol supplied by the manufacturer (e.g. Immudex Cancer-testis Antigen Dextramer® Collection) was followed. Samples were run through a FACS Canto II flow cytometer (BD Biosciences), and data were analyzed by Flow Jo software (Tree star Inc). The results demonstrated that the complete edited population had the greatest affinity to the NY-ESO1 dextramer (see FIG. 19B). The data in FIG. 19 is expressed as Relative Fluorescence Intensity (RFI), meaning the ration between the Mean Fluorescence Intensity (MFI) observed in the sample population (transferred, single edited, or complete edited T cells) as compared with untransduced T cells. Three consecutive experiments were conducted using 3 different donors. The results (FIG. 19C) demonstrated that the CE population had the highest signal.

Additionally, the cells were analysed for phenotypic markers by FACS analysis as in Cieri et al, ((2013) *Blood* 121 p. 573-584). The analysis demonstrated that a proportion of the modified T cells displayed the phenotype of stem memory T ($T_{SCM}$) cells, characterized by the co-expression of CD45RA, CD62L and CD95.

Figure 20A:
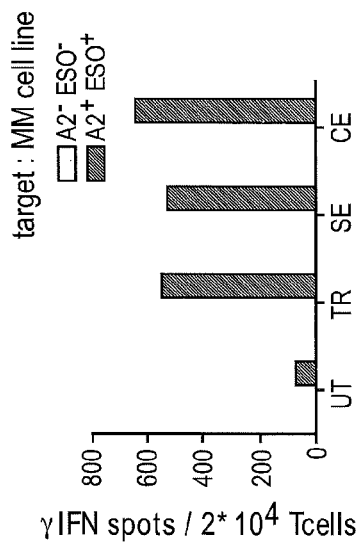

The complete edited population of TCR edited lymphocytes displayed high avidity for the cognate antigen when challenged with increasing doses of the NY-ESO1 157-165 peptide in a γ-IFN ELISpot assay (e.g. Human IFN gamma ELISPOT Ready-SET-Go!®, eBioscience®). Effector cells used were untransduced (UT), Transferred, single edited T cells (SE) and complete edited T cells (CE). The results are shown in FIG. 20A and demonstrated that the TCR complete edited (CE) population displayed high avidity for the peptide. T2 cells were loaded with increasing concentrations of NY-ESO-1 157-165 peptide, or with the unrelated $WT1_{126-434}$ peptide derived from the Wilms Tumor antigen 1 ("T2-$WT1_{126-134}$").

Figure 20B:
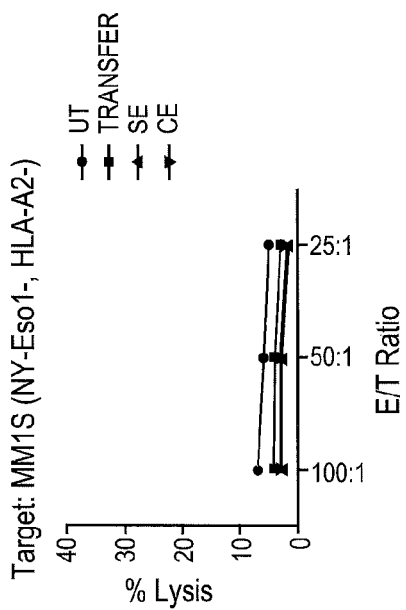
FIG. 20B depicts binding of the T cells to myeloma cell lines that are either HLA-A2⁻, NY-ESO1⁻ (MM1S, "A2-ESO-") or are HLA-A2+, NY-ESO1+ (U266, "A2+ESO+"). Binding to the MM1S cell line was nearly undetectable. The T cells were then tested for their ability to cause lysis of the proper cell target as analysed by a $^{51}$chromium release assay, (FIGS. 20C and 20D) and increased lysis of the relevant target cell was observed in comparison with the irrelevant cells by the edited TCR T cells. For FIGS. 20A, C and D, untreated cells (UT) are shown by ●; Transfer cells are shown by squares; SE cells are shown by ▲; CE cells are shown by ▼.

NY-ESO1 redirected T cells were then challenged with a NY-ESO1+. HLA-A2+ myeloma cell line (U266), to verify their ability to recognize a tumor cell that naturally expressed the NY-ESO1 antigen. First a gamma-IFN ELISpot (described above) was performed using the U266 or the MM cell lines as target (see FIG. 20B) and demonstrated that the NY-ESO1 redirected T cells had high avidity for the relevant HLA-A2+, NY-ESO1+ cells in comparison with untransduced T cells, and almost no binding to the MM1S cells was detected. No recognition was observed against a MM1S (HLA-A2⁻ and NY-ESO1⁻)irrelevant target cell. Next, a $^{51}$chromium release was performed using standard methods as follows: effector T cells were incubated in V-bottom 96-well plates for 5 h with myeloma cell lines (MM1S and U266) which were previously labeled with $^{51}$chromium. Specific lysis was expressed according to the following formula: 100×(average experimental cpm−average spontaneous cpm)/(average maximum cpm−average spontaneous cpm).

Figure 20C:
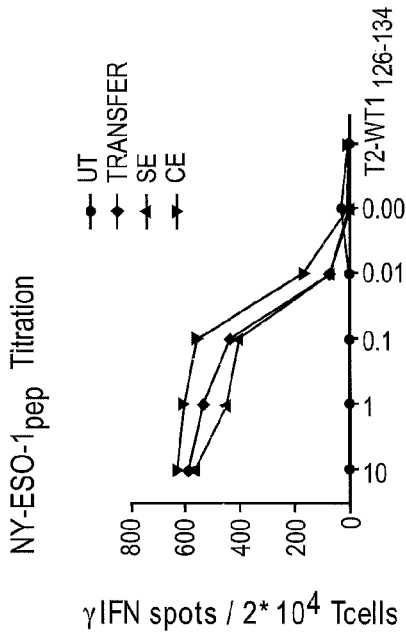
Figure 20D:
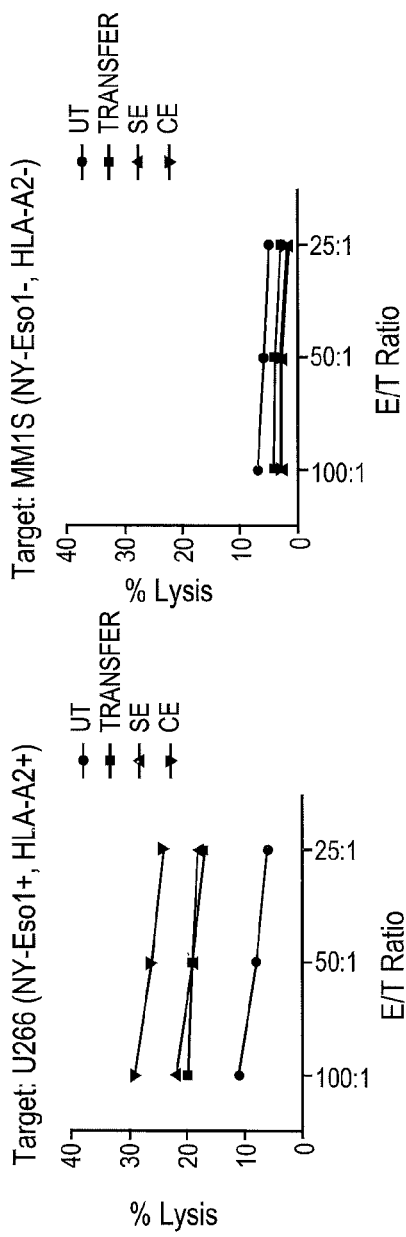

The results (FIGS. 20C and 20D) demonstrated that the different populations were able to cause lysis of the relevant target cell U266 (FIG. 20C) and not the irrelevant target cell MM (FIG. 20D). The complete edited T cells (CE) showed the greatest ability to lyse the appropriate target cells.

Figures 21A, 21B:
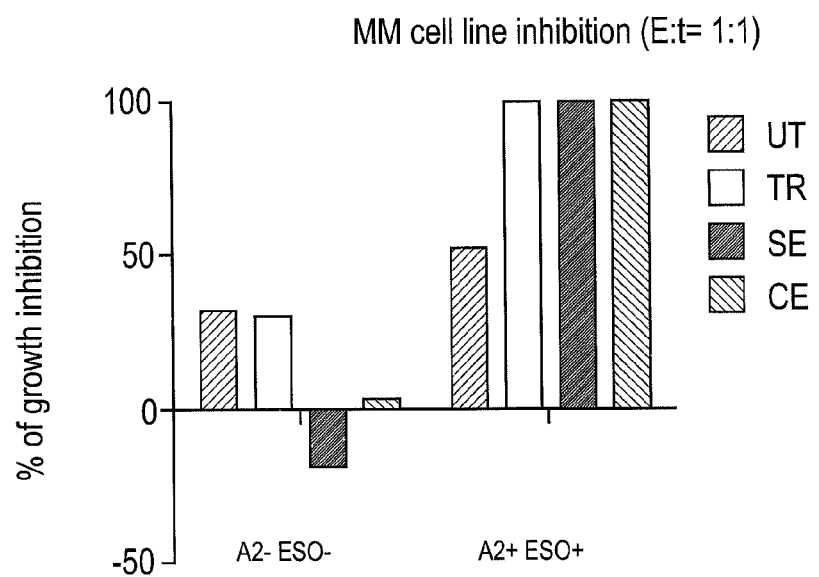
FIG. 21A depicts growth inhibition of the irrelevant MM1S cells that are HLA-A2−, NY-ESO1− in comparison with the U266 HLA-A2+, NY-ESO1+ cells.
FIG. 21B demonstrates that the edited T cells expand of 2 folds in the presence of the U266 HLA-A2+, NY-ESO1+ target.

The NY-ESO1 re-directed T cells were also tested for their ability to specifically kill NY-ESO1+, HLA-A2⁺ tumor cells in a co-culture experiment (see FIG. 21). In this experiment, the effector T cells were co-cultured with the relevant U266 cell line ("A2+ESO+") or with the irrelevant MM1S line ("A2−ESO−") for 4 days at an effector/target ratio of 1:1. The results demonstrate that the re-directed T cell effectors are able to prohibit growth the relevant HLA-A2+, NY-ESO1+ cell line. FIG. 21B demonstrates that the edited T cells, expanded by 2 fold in the presence of the U266 HLA-A2+, NY-ESO1+ target, but did not expand in the presence of the irrelevant A2-ESO-control.

Example 12

Alloreactivity of Edited T Cells

To compare the alloreactive potential of the three NY-ESO-1 redirected T cell populations, TCR transferred (Transfer), TCR single edited (SE) and TCR complete edited (CE) T cells were separately plated in mixed lymphocyte reactions (MLR) against irradiated allogeneic peripheral blood mononuclear cells (PBMCs). Donor-matched PBMCs and mock-transduced T cells (UT) were used as controls. After two cycles of stimulation (S 1 10 days, S2 7 days), effector cells were tested against a PHA cell line obtained by the same allogeneic targets, and against the autologous cells in a $^{51}$Cr release and in a γ-Interferon (γ-IFN) Elispot assay.

Simultaneously, NY-ESO-1 redirected T cells and controls were stimulated against NY-ESO-1157-165 pulsed HLA-A2+ irradiated cells. After two cycles of stimulation (S1 10 days, S2 7 days), effector cells were tested against the HLA-A2+ T2 cell line pulsed (C) with the NY-ESO-1157-165 peptide or unpulsed (D).

No response was observed against the autologous cells. Furthermore, as shown in FIG. 22, lysis of the allogeneic target by Transfer T cells was significantly higher than by both SE and CE T cells (p=0.05) (FIG. 22A). In addition, γ-IFN Elispot confirmed the statistically significant difference between Transfer and edited T cells in secreting γ-IFN upon allogeneic stimulation (FIG. 22B), suggesting that the residual endogenous polyclonal TCRs and possibly mispaired TCRs expressed on the cell surface of TCR-transferred T cells can lead to off-target reactivity, while SE and CE T cells are devoid of such reactivity. NY-ESO-1 redirected T cells (Transfer, SE and CE) were equally able to lyse T2 cells pulsed with the NY-ESO-1 specific peptide (FIG. 22C) with high specificity as compared to unpulsed cells (FIG. 22D).

Example 13

In Vivo Experiments

To compare the efficacy and safety of NY-ESO-1 single edited (SE), complete edited (CE) and TCR transferred (transfer) T cells in vivo, we set up a mouse model based on the injection of the Multiple Myeloma (MM) U266 cell line (HLA-A2+, NY-ESO-1+, hCD138+) followed by the administration of T cells in sub-lethally irradiated NSG mice. Briefly, 10×10$^6$ U266 cells were injected via tail vein at day 0. At day 3 mice received intravenously either: PBS (U266), or 10×10$^6$ NY-ESO-1 transfer, SE, CE T cells, or donor matched PBMC or donor matched mock-transduced T cells (UT) as controls. Finally a group of mice received 10×10$^6$ complete edited T cells redirected to the WT1 126-134 peptide, not expressed by U266 (CEWT1). Mice were monitored at least 3 times per week for xenogeneic Graft versus Host Disease (GvHD) signs and sacrificed by day 70 in absence of any pathological signs. Due to the long time required for U266 to engraft in mice, we considered evaluable for the anti-tumor response only animals that were sacrificed at day 70. All mice were considered evaluable for GvHD assessment.

Figure 23A:
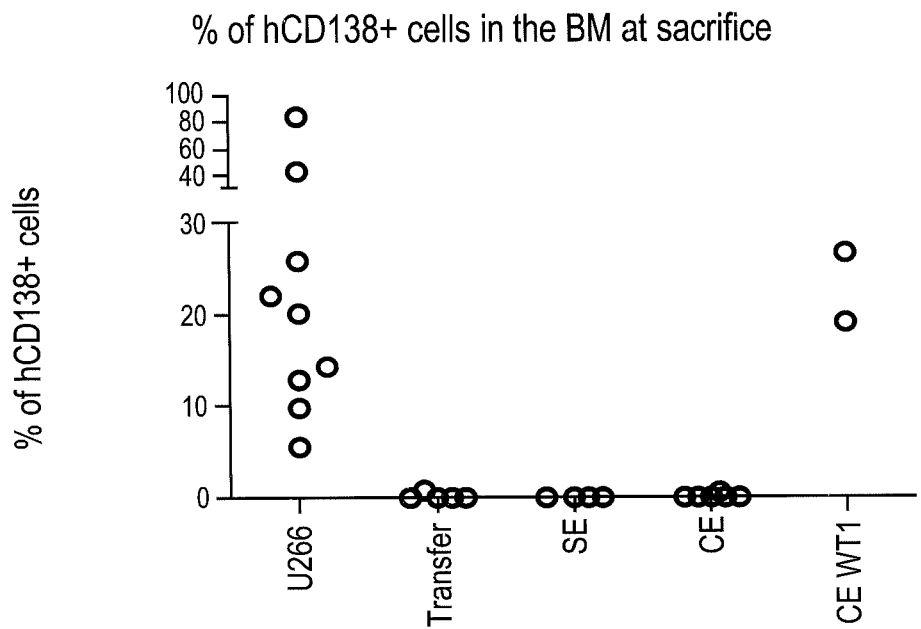
FIG. 23, panels A and B, depict the percent of human Multiple Myeloma CD138+ cells (hCD138+) in bone marrow of mice treated with the indicated cells (FIG. 23A) and the pathological score (hCD3+ infiltration) in mice treated with the indicated cells (FIG. 23B).

Results are shown in FIG. 23. FIG. 23A shows the percent of human CD138+ MM cells identified by cytofluorimetric analysis of cells harvested from the bone marrow of euthanized mice. In mice treated with the NY-ESO1 redirected T cells, no residual disease could be detected in the bone marrow, nor in the spleen (not shown) at the time of sacrifice, demonstrating the in vivo efficacy of the NY-ESO1 redirected cells. By contrast, all mice injected with PBS (U266) or CE WT1 T cells had tumor cells detectable in their bone marrow.

Figure 23B:
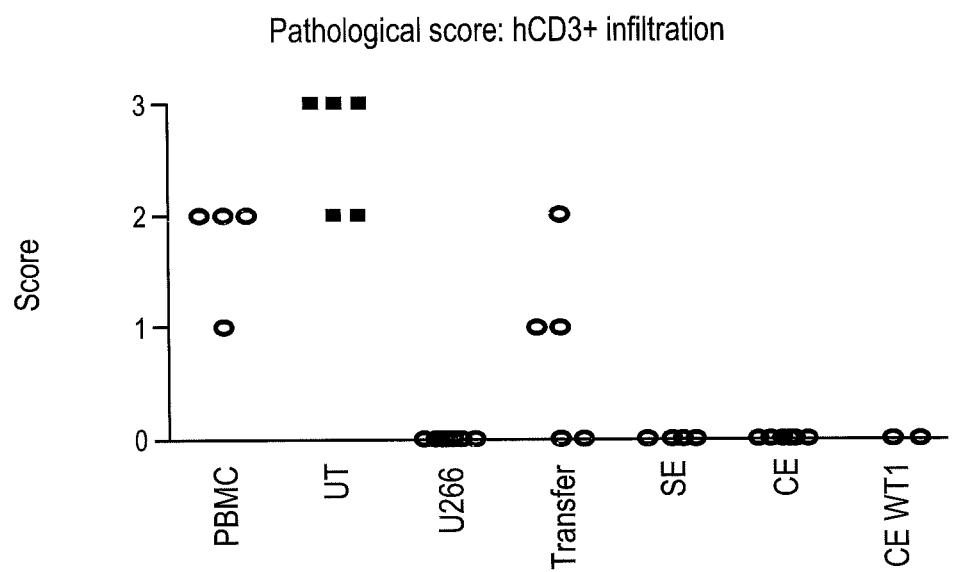

At sacrifice, all organs were collected, fixed in formalin, stained with hematoxylin/eosin and simultaneously analyzed by immunohistochemistry after counterstaining with monoclonal anti-hCD3 antibodies and peroxidase-conjugated second-step reagent to detect any possible GvHD activity and to examine T cell specificity. Infiltration into the mouse organs would indicate inappropriate homing of the T cells, and potentially, the beginning stages of GvHD. Pathological grading ranged from 0 (no hCD3+ cells infiltration) to 3 (massive and diffuse hCD3+ cells infiltration). Interestingly, human CD3+ T cells were found infiltrating lungs and livers of 3 out of 5 animals infused with conventional TCR transferred T cells ("Transfer"), similarly to what was observed in 4 of 4 mice injected with donor-matched unmanipulated PBMCs ("PBMC") or with untransduced lymphocytes (5 of 5 mice, "UT"). Conversely, no lymphocyte infiltration was detected in organs of mice treated with either NY-ESO-1 SE or CE T cells (FIG. 23B).

Example 14

TCR Editing by mRNA Electroporation

A. Single TCR Editing

TCR editing by mRNA electroporation of nuclease message was evaluated as follows. Briefly, Human T lymphocytes from peripheral blood were stimulated with anti-CD3/CD28 beads and electroporated two days later with decreasing doses of in vitro transcribed mRNA encoding for the ZFNs pair specific for the TRAC or the TRBC gene.

Figure 24A:
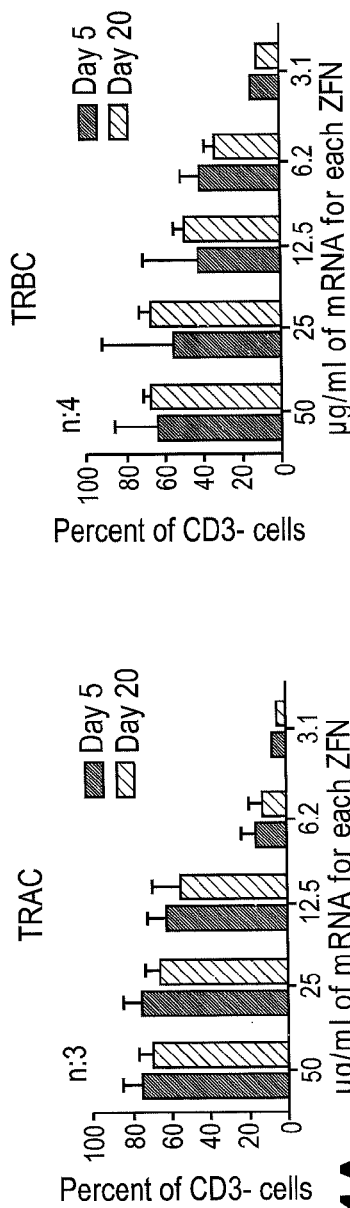
FIG. 24A depicts ZFN-induced TCR disruption at the indicated dosages at day 5 or 20 days after ZFN electroporation into lymphocytes using either TRAC-specific ZFN mRNAs (left graph) or TRBC-specific ZFN mRNAs (right graph).
Figure 24B:
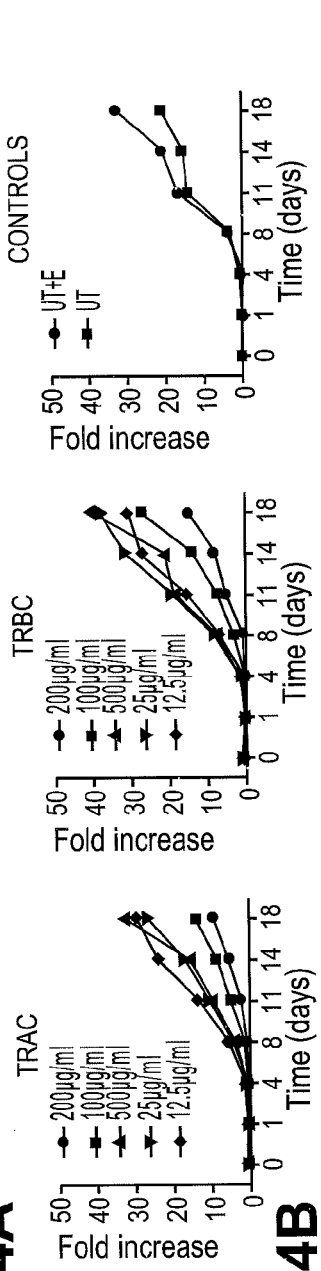
FIG. 24B depicts the fold increase in the number of treated cells. TRAC-specific ZFN treated cells are shown in the left most graph; TRBC-ZFN treated cells are shown in the middle graph and controls are shown in the right most graph. "UT" refers to untreated cells; "UT+E" refers to mock electroporated cells.
Figure 24C:
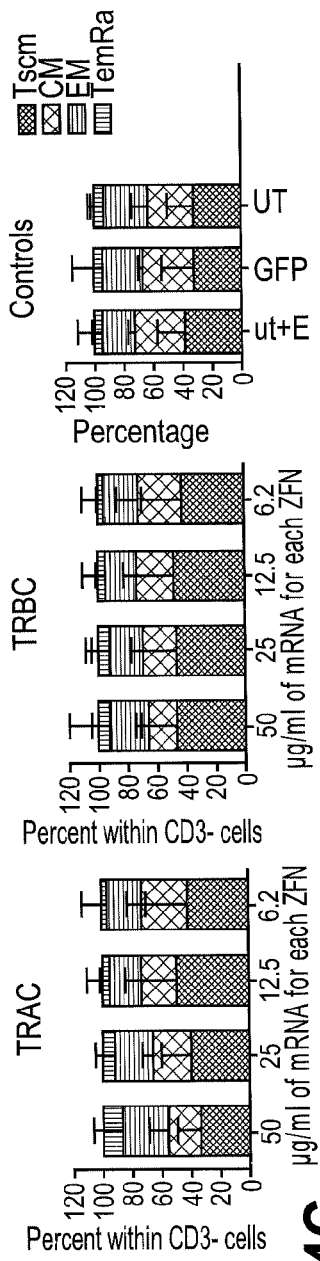
FIG. 24C shows the percentage of the indicated surface phenotypes at day 18 after stimulation. TRAC-ZFN treated cells are shown in the left most graph; TRBC-ZFN treated cells are shown in the middle graph and controls are shown in the right most graph. T stem memory cells (TSCM) are defined as CD62L+ CD45RA+; T central memory (TCM) as CD62L+ CD45RA−; T effector memory (TEM) as CD62L− CD45RA− and terminal effectors (TEMRA) as CD62L− CD45RA+. UT: untreated cells; UT+E: mock electroporated cells; GFP: cells electroporated with GFP encoding mRNA.

The extent of ZFN-induced TCR disruption upon treatment was measured as percentage of CD3 negative cells at 5 or 20 days after electroporation in lymphocytes treated with the TRAC-ZFNs (left panel of FIG. 24A) and TRBC-ZFNs (right panel of FIG. 24A). In addition, the fold increase in the number of treated cells during culture was also evaluated in TRAC-ZFN treated cells (left panel of FIG. 24B); TRBC-ZFN treated cells (middle panel of FIG. 24B); and in control cells (right panel of FIG. 24B). Further, the surface phenotype of T cells at day 18 after stimulation was also evaluated. T stem memory cells (TSCM) are defined as CD62L+CD45RA+ (See, Gattinoni et al. (2011) Nat Med. 17(10):1290-7; and Cieri (2013) Blood 121(4):573-84); T central memory (TCM) as CD62L+ CD45RA−; T effector memory (TEM) as CD62L− CD45RA− and terminal effectors (TEMRA) as CD62L− CD45RA+. UT: untreated cells; UT+E: mock electroporated cells; GFP: cells electroporated with GFP encoding mRNA. No statistically significant differences were found in the phenotype composition of the TRAC-ZFNs and TRBC-ZFNs treated cells at the mRNA doses utilized (two-way Anova).

B. TCR Double Editing

Figure 25A:
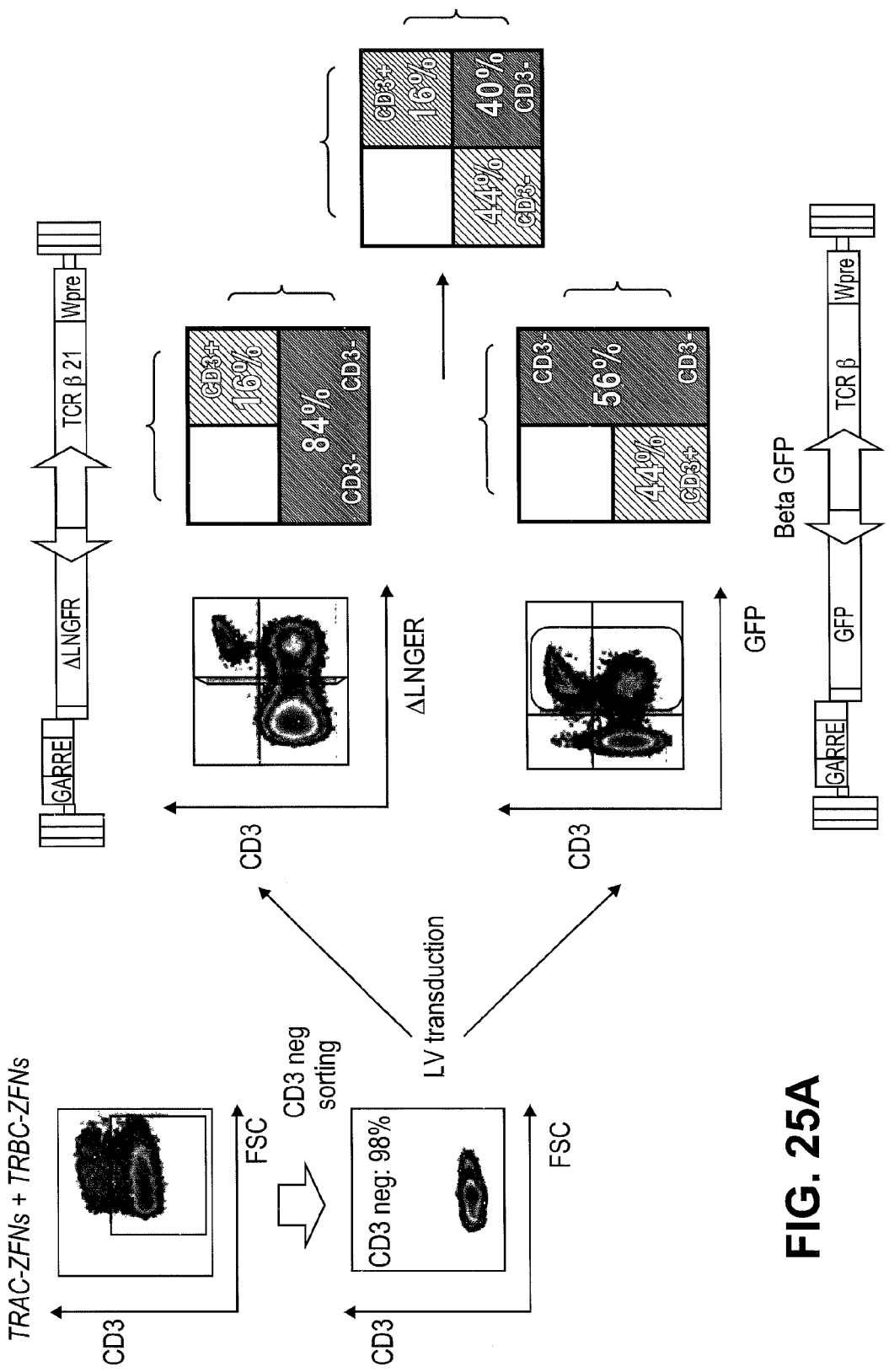
FIG. 25A shows a representative analysis to quantify the amount of complete, TCR-alpha and TCR-beta edited cells in the CD3 negative fraction of the co-treated cells. The fraction of single TCR-alpha or TCR-beta edited cells (shown in the squares on right) was measured as percentage of transduced cells that restore surface expression of the CD3 upon complementation with an exogenous TCR alpha or beta gene. The amount of complete edited cells in the total CD3 negative population is then calculated by subtracting the two percentages of single edited cells.

Human T lymphocytes from peripheral blood were stimulated with anti-CD3/CD28 beads and co-electroporated two days later with in vitro transcribed mRNAs encoding for both the TRAC and TRBC specific ZFNs pairs as described above. Next, an analysis was done to quantify the amount of complete, TCR-alpha and TCR-beta edited cells in the CD3 negative fraction of the co-treated cells. Briefly, 5 days after electroporation, CD3 negative cells were sorted and transduced separately with bi-directional lentiviral vectors (LV) encoding for the alpha or the beta NY-ESO specific TCR chain and a reported gene (LNGFR or GFP, respectively, schematically depicted in FIG. 25A). The fraction of single alpha or beta edited cells was measured as percentage of transduced cells that restore surface expression of the CD3 upon complementation with exogenous TCR alpha or beta. The amount of complete edited cells in the total CD3 negative population was then calculated by subtracting the two percentages of single edited cells. Results are shown in FIG. 25A, demonstrating that 40% of the complete edited cell populations were disrupted at both the TCR-alpha and TCR-beta genes.

Figure 25B:
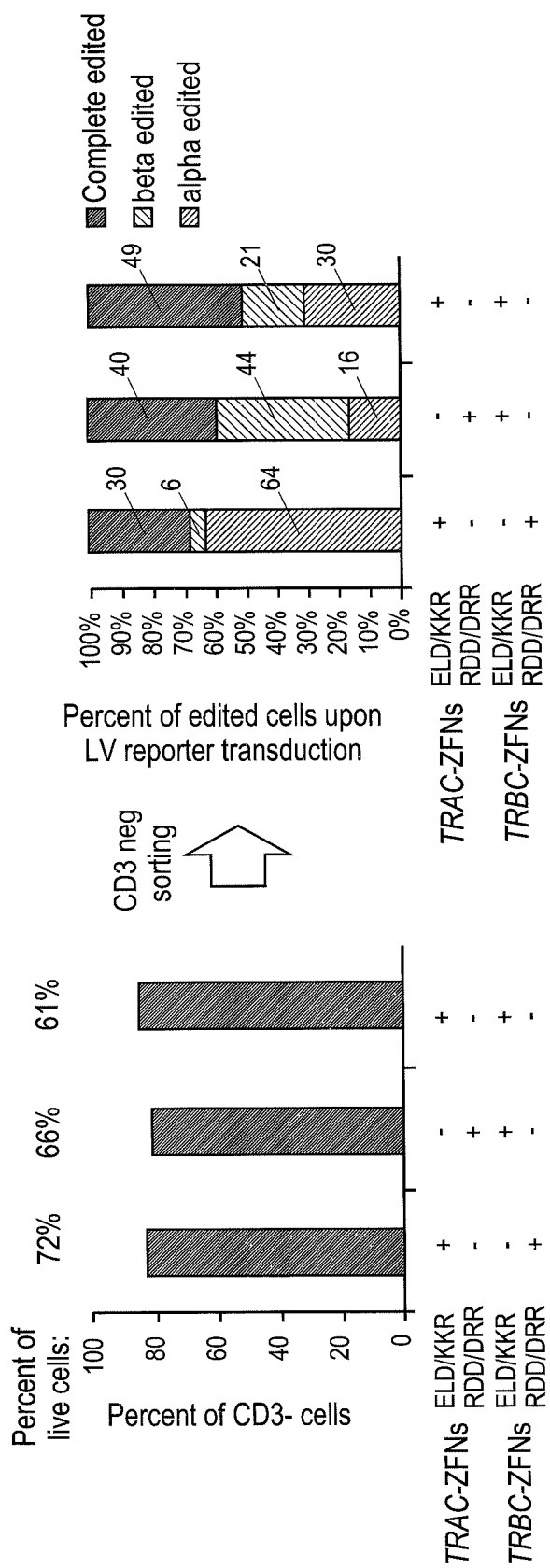
FIG. 25B is a histogram showing the percentages of CD3 negative cells upon co-electroporation of TRAC- and TRBC-specific ZFN encoding mRNAs containing the obligated heterodimeric FokI domains (ELD and KKR) or their respective orthologous version (RDD and DRR) (left panel). The percentages of viable cells (indicated on top of the histogram) were calculated as percentages of 7-Amino-actinomycin D (7-AAD) negative cells gated on singlets. 7-AAD intercalates into double-stranded nucleic acids. It is excluded by viable cells but can penetrate cell membranes of dying or dead cells. The right panel of FIG. 25B shows composition of the edited cells in the CD3 negative fraction calculated using the LV reporter strategy described above. The top portion of each bar shows the percent of completely edited (30%, 40% and 49% from left to right); the middle portion of each bar shows the percentage of beta edited cells (6%, 44% and 21% from left to right bars); and the lower portion of each bar shows the percent of TCR-alpha edited cells (64%, 16% and 30% from left to right bars).

The percentages of CD3 negative (CD3−) cells upon co-electroporation of TRAC- and TRBC-specific ZFN mRNAs containing the obligated heterodimeric FokI domains (ELD and KKR) or their respective orthologous version (RDD and DRR). The percentages of viable cells were calculated as percentages of 7-AAD negative cells gated on singlets. In addition, the composition of the edited cells in the CD3 negative fraction was calculated using the LV reporter strategy described above. Results are shown in FIG. 25B.

The surface phenotype of T cells as described above was also determined at day 18 after stimulation. T stem memory cells (TSCM) are defined as CD62L+ CD45RA+ (Gattinoni et al. (2011), ibid.; Cieri et al. (2013), ibid.), T central memory (TCM) as CD62L+ CD45RA−, T effector memory (TEM) as CD62L− CD45RA− and terminal effectors (TEMRA) as CD62L− CD45RA+. UT: untreated cells. Results are shown in FIG. 25C.

Figures 25C, 25D:
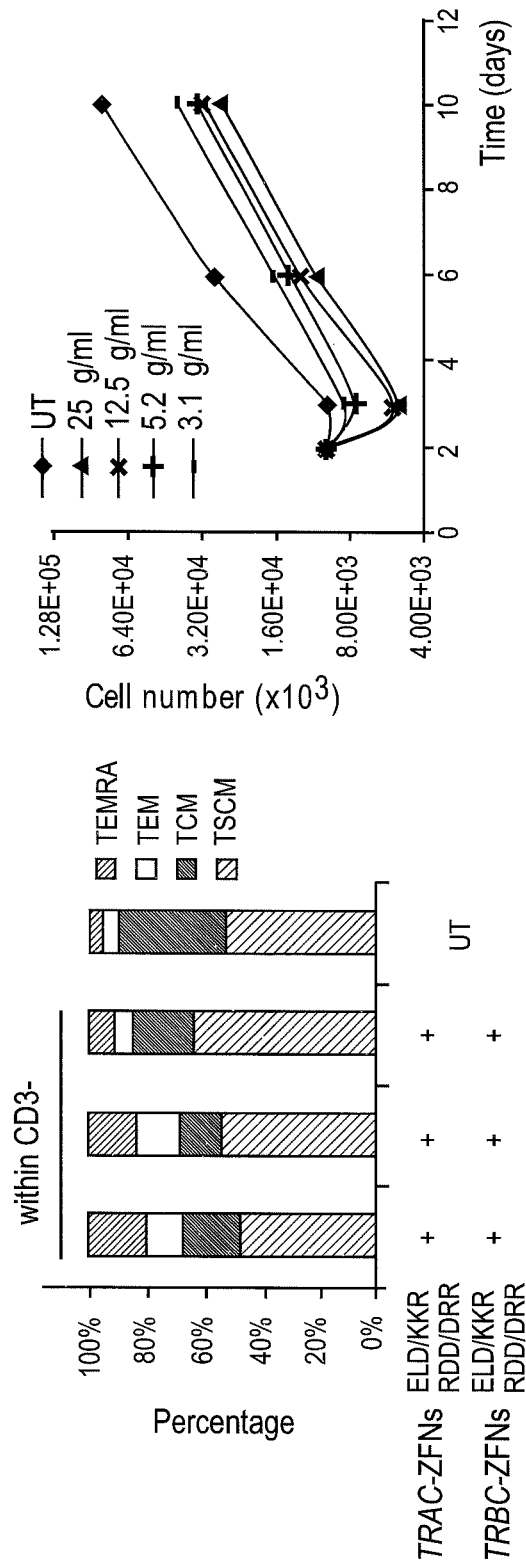
FIG. 25C shows the surface phenotype of T cells from at day 18 after stimulation. Four phenotypes are shown: the bottom most portion of each bar shows stem memory cells (TSCM) defined as CD62L+ CD45RA+; the portion second from the bottom on each bar shows T central memory (TCM) as CD62L+ CD45RA−; the portion second from the top of each bar shows T effector memory (TEM) as CD62L− CD45RA− and the top most portion of each bar shows terminal effectors (TEMRA) as CD62L− CD45RA+. "UT" refers to untreated cells.
FIG. 25D shows growth curves of T cells co-electroporated with the indicated doses of TRAC- and TRBC-specific ZFN mRNAs.

Growth curves of T cells co-electroporated with the indicated doses of TRAC- and TRBC-specific ZFN mRNAs were also determined and showed that following an initial acute phase of cell loss the day after the co-electroporation, the surviving cells continue to expand in culture with similar kinetics compared to untreated (UT) controls (FIG. 25D).

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated T-lymphocyte comprising a stably integrated exogenous sequence encoding a T-cell receptor (TCR), wherein at least one endogenous TCR gene within the cell is partially or completely inactivated by a nuclease, wherein the nuclease is a TALEN that binds to a target sequence site in the endogenous TCR gene, wherein said target sequence site is selected from SEQ ID NO: 147-153, the TALEN comprising a TAL-effector DNA-binding domain and a cleavage domain, and further wherein the TAL-effector DNA-binding domain comprises a C-terminal truncation as compared to a wild-type TAL-effector DNA-domain.

2. The isolated T-lymphocyte of claim 1, wherein the endogenous TCR gene is a TCR α or TCR β gene.

3. The isolated T-lymphocyte of claim 1, wherein a polynucleotide encoding the TALEN that binds to a target sequence site selected from SEQ ID NO: 147-153 is introduced into the cell using an integrase-defective lentiviral vector (IDLV), AAV, a plasmid or mRNA, the TALEN comprising a TAL-effector DNA-binding domain and a cleavage domain, and further wherein the TAL-effector DNA-binding domain comprises a C-terminal truncation as compared to a wild-type TAL-effector DNA-domain.

4. The isolated T-lymphocyte of claim 1, wherein the exogenous sequence is introduced into an endogenous TCR gene, a CCR5 gene or an AAVS1 gene.

5. The isolated T-lymphocyte of claim 1, wherein the exogenous sequence is selected from the group consisting of a tumor antigen specific TCR transgene wherein the TCR transgene is a TCR α transgene, a TCR β transgene and combinations thereof.

6. The isolated T-lymphocyte of claim 5, wherein the tumor antigen comprises NY-ESO1.

7. A pharmaceutical composition comprising the isolated T-lymphocyte of claim 1.

8. A method of generating a T-lymphocyte according to claim 1, the method comprising:
   inactivating an endogenous TCR gene in the T-lymphocyte using one or more polynucleotides encoding the one or more TALENs, each TALEN comprising a TAL-effector DNA-binding domain and a cleavage domain, and further wherein the TAL-effector DNA-binding domain comprises a C-terminal truncation as compared to a wild-type TAL-effector DNA-domain, wherein the TALEN cleave the endogenous TCR gene; and stably integrating the exogenous sequence into the genome of the T-lymphocyte.

9. The method of claim 8, wherein the endogenous TCR gene is a TCR α and/or TCR β gene.

10. The method of claim 8, wherein the exogenous sequence is introduced into the cell using an integrase-defective lentiviral vector (IDLV), retroviral vector (RV) or lentiviral Vector (LV).

11. The method of claim 10, wherein the exogenous sequence is introduced by IDLV into an endogenous TCR gene, a CCR5 gene or an AAVS1 gene.

12. The method of claim 8, wherein the exogenous sequence is selected from the group consisting of a tumor antigen specific TCR transgene wherein the TCR transgene is a TCR α transgene, a TCR β transgene and combinations thereof.

13. The method of claim 12, wherein the tumor antigen comprises NY-ESO1.

* * * * *

SEQUENCE LISTING

```
<160> NUMBER OF SEQ ID NOS: 155

<210> SEQ ID NO 1
<211> LENGTH: 28
<212> TYPE: DNA
<213> ORGANISM: Homo sapiens

<400> SEQUENCE: 1
ctatggactt caagagcaac agtgctgt                                         28

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ser Gly Asp Leu Thr Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Arg Thr His Leu Lys Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Gly Asp Arg Asn Lys
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Arg Ser Asn Leu Ser Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Asp Ala Leu Thr Gln
1               5

<210> SEQ ID NO 7
<211> LENGTH: 28
<212> TYPE: DNA
<213> ORGANISM: Homo sapiens

<400> SEQUENCE: 7
ctcatgtcta gcacagtttt gtctgtga                                         28

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Ser Gly Ser Leu Ser Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Ser Val Arg Asn Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp Asn Leu Ser Thr
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Arg Ser Ala Leu Ala Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Lys Gln Asn Leu Asp Ala
1               5

<210> SEQ ID NO 13
<211> LENGTH: 28
<212> TYPE: DNA
<213> ORGANISM: Homo sapiens

<400> SEQUENCE: 13
gtgctgtggc ctggagcaac aaatctga                                      28

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Arg Ser Ala Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ser Gly His Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Ser Asp Leu Ser Arg
1               5
```

```
<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Asp Ala Leu Ser Arg
1               5

<210> SEQ ID NO 18
<211> LENGTH: 28
<212> TYPE: DNA
<213> ORGANISM: Homo sapiens

<400> SEQUENCE: 18
ttgctcttga agtccataga cctcatgt                                           28

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Lys Thr Ser Leu Gln Ala
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ser Gly Asn Leu Ala Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Lys Glu Glu Leu Asn Glu
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Ser Asp Leu Ser Arg
```

```
<210> SEQ ID NO 23
<211> LENGTH: 28
<212> TYPE: DNA
<213> ORGANISM: Homo sapiens

<400> SEQUENCE: 23
gctgtggcct ggagcaacaa atctgact                                          28

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Asn Val Asp Leu Ile Glu
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Ser Asn Leu Ser Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ser Asp Ala Leu Ser Val
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ser Ser His Arg Thr Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

Trp Arg Ser Cys Arg Ser Ala
1               5

<210> SEQ ID NO 29
<211> LENGTH: 28
<212> TYPE: DNA
<213> ORGANISM: Homo sapiens

<400> SEQUENCE: 29
ctgttgctct tgaagtccat agacctca                                         28

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Ser Ser Asp Arg Lys Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ser Asp Asn Leu Ser Val
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Phe Ile Leu Arg Gly
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Ser Gly Ser Leu Thr Arg
1               5

<210> SEQ ID NO 34
<211> LENGTH: 28
<212> TYPE: DNA
<213> ORGANISM: Homo sapiens

<400> SEQUENCE: 34
ctgtggcctg gagcaacaaa tctgactt                                         28

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Thr Ser Thr Leu Ser Lys
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Asp Ala Leu Ala Arg
1               5

<210> SEQ ID NO 37
<211> LENGTH: 28
<212> TYPE: DNA
<213> ORGANISM: Homo sapiens

<400> SEQUENCE: 37
ctgactttgc atgtgcaaac gccttcaa                                        28

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Arg Ser Ser Leu Ala Ser
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

His Lys Trp Val Leu Arg Gln
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Arg Ser Asn Leu Thr Arg
1               5

<210> SEQ ID NO 41
<211> LENGTH: 28
<212> TYPE: DNA
<213> ORGANISM: Homo sapiens

<400> SEQUENCE: 41
ttgttgctcc aggccacagc actgttgc                                          28

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Trp Gly Thr Arg Tyr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Arg Gly Thr Leu Ala Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Asp Asn Leu Arg Glu
1               5

<210> SEQ ID NO 45
<211> LENGTH: 28
<212> TYPE: DNA
<213> ORGANISM: Homo sapiens

<400> SEQUENCE: 45
tgaaagtggc cgggtttaat ctgctcat                                          28

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Ala His Leu Ser Arg
1               5

<210> SEQ ID NO 47

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Asp His Leu Ser Val
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Asn Asn His Arg Ile Thr
1               5

<210> SEQ ID NO 49
<211> LENGTH: 28
<212> TYPE: DNA
<213> ORGANISM: Homo sapiens

<400> SEQUENCE: 49
aggaggattc ggaacccaat cactgaca                                          28

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Arg Ser Asn Leu Val Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Asn Asp Asp Arg Lys Lys
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ser Gly Asn Leu Thr Arg
1               5
```

```
<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ser Ala Asn Leu Ser Arg
1               5

<210> SEQ ID NO 54
<211> LENGTH: 28
<212> TYPE: DNA
<213> ORGANISM: Homo sapiens

<400> SEQUENCE: 54
gaggaggatt cggaacccaa tcactgac                                             28

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Arg Ser Thr Leu Arg Gln
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Ser Gly His Leu Ala Arg
1               5

<210> SEQ ID NO 57
<211> LENGTH: 28
<212> TYPE: DNA
<213> ORGANISM: Homo sapiens

<400> SEQUENCE: 57
tgaaagtggc cgggtttaat ctgctcat                                             28

<210> SEQ ID NO 58
<211> LENGTH: 28
<212> TYPE: DNA
<213> ORGANISM: Homo sapiens

<400> SEQUENCE: 58
ccgtagaact ggacttgaca gcggaagt                                             28

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 59

Arg Ser Asp Val Leu Ser Ala
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Arg Ser Asn Arg Ile Lys
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ser Asp Val Leu Ser Glu
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ser Gly Ser Leu Thr Arg
1               5

<210> SEQ ID NO 63
<211> LENGTH: 28
<212> TYPE: DNA
<213> ORGANISM: Homo sapiens

<400> SEQUENCE: 63
tctcggagaa tgacgagtgg acccagga                                        28

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ser Asp His Leu Ser Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic

```
                               peptide

<400> SEQUENCE: 65

Arg Ser Asp Asn Leu Thr Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Ser Ser Asn Arg Lys Thr
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ser Ala Asn Leu Ala Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Gln Phe Asn Arg Asn Gln
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Ser Ser Asn Leu Ser Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Arg Phe Asn Leu Ser Asn
1               5

<210> SEQ ID NO 71
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu His Phe Gln Leu Thr Gly
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Lys Phe Ala Leu Ala Asn
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Ser Gly Ala Leu Ala Arg
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Leu Ser Val Leu Thr Ile
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Arg Ala Asn Leu Thr Arg
1               5

<210> SEQ ID NO 76
<211> LENGTH: 37
<212> TYPE: DNA
<213> ORGANISM: Homo sapiens

<400> SEQUENCE: 76
aggcacaagc aatgtcacaa gtaccatgct tgtactt                             37
```

```
<210> SEQ ID NO 77
<211> LENGTH: 37
<212> TYPE: DNA
<213> ORGANISM: Homo sapiens

<400> SEQUENCE: 77
aggtacaagt aaagacgtat gaactttgct tgtactt                              37

<210> SEQ ID NO 78
<211> LENGTH: 37
<212> TYPE: DNA
<213> ORGANISM: Homo sapiens

<400> SEQUENCE: 78
aaatacaagc caagccaagg tggctttgcg tgtaaat                              37

<210> SEQ ID NO 79
<211> LENGTH: 38
<212> TYPE: DNA
<213> ORGANISM: Homo sapiens

<400> SEQUENCE: 79
atatacaatt aaagtcagct tttactttgc agttactt                             38

<210> SEQ ID NO 80
<211> LENGTH: 38
<212> TYPE: DNA
<213> ORGANISM: Homo sapiens

<400> SEQUENCE: 80
tagaacatcc aaactctgga ccgactttgc atgtccag                             38

<210> SEQ ID NO 81
<211> LENGTH: 37
<212> TYPE: DNA
<213> ORGANISM: Homo sapiens

<400> SEQUENCE: 81
attcaaacac aaagtcccgt ggattttgct tttaaat                              37

<210> SEQ ID NO 82
<211> LENGTH: 37
<212> TYPE: DNA
<213> ORGANISM: Homo sapiens

<400> SEQUENCE: 82
atgcaggagc aaggtcactc tgaccttcct ttgcctt                              37

<210> SEQ ID NO 83
<211> LENGTH: 37
<212> TYPE: DNA
<213> ORGANISM: Homo sapiens

<400> SEQUENCE: 83
atgcacacac aaactcattt aagctttgct tttccat                              37

<210> SEQ ID NO 84
<211> LENGTH: 37
<212> TYPE: DNA
<213> ORGANISM: Homo sapiens

<400> SEQUENCE: 84
cagcccatgg aatgtcattc tcacattgct tgtgctt                              37
```

<210> SEQ ID NO 85
<211> LENGTH: 37
<212> TYPE: DNA
<213> ORGANISM: Homo sapiens

<400> SEQUENCE: 85
aagcaaaaga aaatcaata tgacttggct ttggctt                             37

<210> SEQ ID NO 86
<211> LENGTH: 38
<212> TYPE: DNA
<213> ORGANISM: Homo sapiens

<400> SEQUENCE: 86
aaggtcactc actgtctgtg tggagtttgc gtgtcctc                           38

<210> SEQ ID NO 87
<211> LENGTH: 38
<212> TYPE: DNA
<213> ORGANISM: Homo sapiens

<400> SEQUENCE: 87
aagcaggagc aaagtcacat cttacattgc ggcggcat                           38

<210> SEQ ID NO 88
<211> LENGTH: 38
<212> TYPE: DNA
<213> ORGANISM: Homo sapiens

<400> SEQUENCE: 88
atgtaattcc aaagtcctcc atgacctggc ttctacct                           38

<210> SEQ ID NO 89
<211> LENGTH: 38
<212> TYPE: DNA
<213> ORGANISM: Homo sapiens

<400> SEQUENCE: 89
ctacaaattc aatgacagta gagactttgc ttttactt                           38

<210> SEQ ID NO 90
<211> LENGTH: 37
<212> TYPE: DNA
<213> ORGANISM: Homo sapiens

<400> SEQUENCE: 90
atgcaacagc aagagcagca tgactttgtt tttccctt                           37

<210> SEQ ID NO 91
<211> LENGTH: 42
<212> TYPE: DNA
<213> ORGANISM: Homo sapiens

<400> SEQUENCE: 91
gtgctgtggc ctggagcaac aaatctgact ttgcatgtgc aa                      42

<210> SEQ ID NO 92
<211> LENGTH: 38
<212> TYPE: DNA
<213> ORGANISM: Homo sapiens

<400> SEQUENCE: 92
cccaagccag ggctactgct gggtggaact ggacatgc                           38

```
<210> SEQ ID NO 93
<211> LENGTH: 38
<212> TYPE: DNA
<213> ORGANISM: Homo sapiens

<400> SEQUENCE: 93
ccctgtgcgg ttctgcttaa cagtagaaca ggacactt                           38

<210> SEQ ID NO 94
<211> LENGTH: 37
<212> TYPE: DNA
<213> ORGANISM: Homo sapiens

<400> SEQUENCE: 94
acatgtcaga ttctacatga ggtagaactg ttcttgt                            37

<210> SEQ ID NO 95
<211> LENGTH: 37
<212> TYPE: DNA
<213> ORGANISM: Homo sapiens

<400> SEQUENCE: 95
acaagggcag ctctgtccaa ggtagcactg ggcctgt                            37

<210> SEQ ID NO 96
<211> LENGTH: 37
<212> TYPE: DNA
<213> ORGANISM: Homo sapiens

<400> SEQUENCE: 96
cgatgtccag atgtacctca ggaaggactg gccctgg                            37

<210> SEQ ID NO 97
<211> LENGTH: 38
<212> TYPE: DNA
<213> ORGANISM: Homo sapiens

<400> SEQUENCE: 97
ccaagtcctc ctctaggaag gggtagaact ggaatttg                           38

<210> SEQ ID NO 98
<211> LENGTH: 37
<212> TYPE: DNA
<213> ORGANISM: Homo sapiens

<400> SEQUENCE: 98
gaaggtccag tgcaatgttg aatagaagtg gacatct                            37

<210> SEQ ID NO 99
<211> LENGTH: 37
<212> TYPE: DNA
<213> ORGANISM: Homo sapiens

<400> SEQUENCE: 99
agaggcccac tcctagaagg ggtagacctg gatctgg                            37

<210> SEQ ID NO 100
<211> LENGTH: 37
<212> TYPE: DNA
<213> ORGANISM: Homo sapiens

<400> SEQUENCE: 100
```

```
ccaggtccag ttctaccagc cacagatgtg agcatgt                              37

<210> SEQ ID NO 101
<211> LENGTH: 38
<212> TYPE: DNA
<213> ORGANISM: Homo sapiens

<400> SEQUENCE: 101
acaattccag ttcaagaatc ttttaaaggt ggacatgg                             38

<210> SEQ ID NO 102
<211> LENGTH: 38
<212> TYPE: DNA
<213> ORGANISM: Homo sapiens

<400> SEQUENCE: 102
gctggtgcag ctctacacgg atgcagagct ggtcctcc                             38

<210> SEQ ID NO 103
<211> LENGTH: 37
<212> TYPE: DNA
<213> ORGANISM: Homo sapiens

<400> SEQUENCE: 103
cctgggccag tgctgcttgt ccttgaaccg ggcctgg                              37

<210> SEQ ID NO 104
<211> LENGTH: 37
<212> TYPE: DNA
<213> ORGANISM: Homo sapiens

<400> SEQUENCE: 104
ggagatccag tgcgacagtc agaagaaggg gactcgg                              37

<210> SEQ ID NO 105
<211> LENGTH: 38
<212> TYPE: DNA
<213> ORGANISM: Homo sapiens

<400> SEQUENCE: 105
ctacaaattc aatgacagta gagactttgc ttttactt                             38

<210> SEQ ID NO 106
<211> LENGTH: 38
<212> TYPE: DNA
<213> ORGANISM: Homo sapiens

<400> SEQUENCE: 106
ccaggtcagg ttccggaaag aagtagaact tgacccct                             38

<210> SEQ ID NO 107
<211> LENGTH: 41
<212> TYPE: DNA
<213> ORGANISM: Homo sapiens

<400> SEQUENCE: 107
tcaagtccag ttctacgggc tctcggagaa tgacgagtgg a                         41

<210> SEQ ID NO 108
<211> LENGTH: 100
<212> TYPE: DNA
<213> ORGANISM: Homo sapiens

<400> SEQUENCE: 108
```

```
tagacatgag gtctatggac ttcaagagca acagtgctgt ggcctggagc aacaaatctg    60
actttgcatg tgcaaacgcc ttcaacaaca gcattattcc                          100
```

<210> SEQ ID NO 109
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Leu Asp Met Arg Ser Met Asp Phe Lys Ser Asn Ser Ala Val Ala Trp
1               5                   10                  15

Ser Asn Lys Ser Asp Phe Ala Cys Ala Asn Ala Phe Asn Asn Ser Ile
            20                  25                  30

Ile Pro

<210> SEQ ID NO 110
<211> LENGTH: 106
<212> TYPE: DNA
<213> ORGANISM: Homo sapiens

<400> SEQUENCE: 110

```
agacatgagg tctatggact tcaagagcaa cagtgctgtg gcctggagca acaaatctga    60
ctttgcatgt gcaaacgcct tcaacaacag cattattcca gaagac                  106
```

<210> SEQ ID NO 111
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
agacatgagg tctatggact tcaagagcaa cagtgctgtg gcctggagca acaatctgac    60
tttgcatgtg caaacgcctt caacaacagc attattccag aagac                   105
```

<210> SEQ ID NO 112
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

```
agacatgagg tctatggact tcaagagcaa cagtgctgtg gcctggagca acaaatcgac    60
tttgcatgtg caaacgcctt caacaacagc attattccag aagac                   105
```

<210> SEQ ID NO 113
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
agacatgagg tctatggact tcaagagcaa cagtgctgtg gcctggagca acaactgact    60
```
ttgcatgtgc aaacgccttc aacaacagca ttattccaga agac      104

<210> SEQ ID NO 114
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
agacatgagg tctatggact tcaagagcaa cagtgctgtg gcctggagca aaatctgact      60
ttgcatgtgc aaacgccttc aacaacagca ttattccaga agac      104

<210> SEQ ID NO 115
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
agacatgagg tctatggact tcaagagcaa cagtgctgtg gcctggagca acaaatgact      60
ttgcatgtgc aaacgccttc aacaacagca ttattccaga agac      104

<210> SEQ ID NO 116
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
agacatgagg tctatggact tcaagagcaa cagtgctgtg gcctggagca acatctgact      60
ttgcatgtgc aaacgccttc aacaacagca ttattccaga agac      104

<210> SEQ ID NO 117
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
agacatgagg tctatggact tcaagagcaa cagtgctgtg gcctggagca acaaatcctt      60
tgcatgtgca acgccttca acaacagcat tattccagaa gac      103

<210> SEQ ID NO 118
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
agacatgagg tctatggact tcaagagcaa cagtgctgtg gcctggagca acatgactt      60 gcatgtgcaa acgccttcaa caacagcatt attccagaag ac      102

<210> SEQ ID NO 119

```
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
agacatgagg tctatggact tcaagagcaa cagtgctgtg gcctggagca acaaatcgca    60
tgtgcaaacg ccttcaacaa cagcattatt ccagaagac                          99

<210> SEQ ID NO 120
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
agacatgagg tctatggact tcaagagcaa cagtgctgtg gcctggatga ctttgcatgt    60
gcaaacgcct tcaacaacag cattattcca gaagac                             96

<210> SEQ ID NO 121
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
agacatgagg tctatggact tcaagagcaa cagtgctgtg gcctgacttt gcatgtgcaa    60
acgccttcaa caacagcatt attccagaag ac                                 92

<210> SEQ ID NO 122
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
agacatgagg tctatggact tcaagagcaa cagtgctgtt ctgactttgc atgtgcaaac    60
gccttcaaca acagcattat tccagaagac                                    90

<210> SEQ ID NO 123
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
agacatgagg tctatggact tcaagagcaa cagtgctgtg gcctgttgca tgtgcaaacg    60
ccttcaacaa cagcattatt ccagaagac                                     89

<210> SEQ ID NO 124
<211> LENGTH: 88
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 124
agacatgagg tctatggact tcaagagcaa cagtgctgtg gcctggagca acaaatccgc    60
cttcaacaac agcattattc cagaagac                                       88

<210> SEQ ID NO 125
<211> LENGTH: 86
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 125
agacatgagg tctatggact tcaagagcaa cagtgctgtg gcctggagca acaaatccct    60
tcaacaacag cattattcca gaagac                                         86

<210> SEQ ID NO 126
<211> LENGTH: 85
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 126
agacatgagg tctatggact tcaagagcaa cagtgctgtg tttgcatgtg caaacgcctt    60
caacaacagc attattccag aagac                                          85

<210> SEQ ID NO 127
<211> LENGTH: 82
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 127
agacatgagg tctatggact tcaagagcaa cagtgctgtg gcctggagca acgccttcaa    60
caacagcatt attccagaag ac                                             82

<210> SEQ ID NO 128
<211> LENGTH: 82
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 128
agacatgagg tctatggact tcaagagcaa cagtgctgtg gcatgtgcaa acgccttcaa    60
caacagcatt attccagaag ac                                             82

<210> SEQ ID NO 129
<211> LENGTH: 79
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 129
agacatgagg tctatggact tcaagagcaa cagtgctgca tgtgcaaacg ccttcaacaa    60
cagcattatt ccagaagac                                                79

<210> SEQ ID NO 130
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
agacatgagg tctatggact tcaagagcaa cagtgctgca aacgccttca acaacagcat    60
tattccagaa gac                                                      73

<210> SEQ ID NO 131
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
agacatgagg tctatggact tcaagagcaa cagtgctgtg gcctggacaa cagcattatt    60
ccagaagac                                                           69

<210> SEQ ID NO 132
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
agacatgagg tctatggact tcaagagcaa cagtgctgtg gcctggagca ttttccaga    60 agac                                                                64

<210> SEQ ID NO 133
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
agacatgagg tctatggact tcaagagcaa acgccttcaa caacagcatt attccagaag    60
ac                                                                  62

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
acaacagcat tattccagaa gac                                           23

```
<210> SEQ ID NO 135
<211> LENGTH: 106
<212> TYPE: DNA
<213> ORGANISM: Homo sapiens

<400> SEQUENCE: 135
agacatgagg tctatggact tcaagagcaa cagtgctgtg gcctggagca acaaatctga      60
ctttgcatgt gcaaacgcct tcaacaacag cattattcca gaagac                   106

<210> SEQ ID NO 136
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
agacatgagg tctatggact tcaagagcaa cagtgctgtg gcctggagca acaaaatctg      60
actttgcatg tgcaaacgcc ttcaacaaca gcattattcc agaaga                   106

<210> SEQ ID NO 137
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
agacatgagg tctatggact tcaagagcaa cagtgctgtg gcctggagca acaaatcaat      60
ctgactttgc atgtgcaaac gccttcaaca acagcattat tccaga                   106

<210> SEQ ID NO 138
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
agacatgagg tctatggact tcaagagcaa cagtgctgtg gcctggagca acaattgact      60
ttgcatgtgc aaacgccttc aacaacagca ttattccaga aga                      103

<210> SEQ ID NO 139
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
agacatgagg tctatggact tcaagagcaa cagtgctgtg gcctggagca acaaaggact      60
ttgcatgtgc aaacgccttc aacaacagca ttattccaga aga                      103

<210> SEQ ID NO 140
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 140
agacatgagg tctatggact tcaagagcaa cagtgctgtg gcctggagca acagatgact    60
ttgcatgtgc aaacgccttc aacaacagca ttattccaga aga                     103

<210> SEQ ID NO 141
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
agacatgagg tctatggact tcaagagcaa cagtgctgtg gcctggcctg tttgcatgtg    60
caaacgcctt caacaacagc attattccag aaga                               94

<210> SEQ ID NO 142
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
agacatgagg tctatggact tcaagagcaa cagtgctgtg gctgtgctgt ttgcatgtgc    60
aaacgccttc aacaacagca ttattccaga aga                                93

<210> SEQ ID NO 143
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
agacatgagg tctatggact tcaagagcaa cagtgctgtg gcctggagct cttgtgcaaa    60
cgccttcaac aacagcatta ttccagaaga                                    90

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gtgctgtggc ctggagcaa                                                19

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gtgctgtggc ctggagcaac                                               20

-continued

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ctgtggcctg gagcaacaa                                                    19

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ttgaaggcgt ttgcacatgc a                                                 21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gttgaaggcg tttgcacatg c                                                 21

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gttgaaggcg tttgcacatg                                                   20

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ttccgctgtc aagtccagtt c                                                 21

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ctgtcaagtc cagttcta                                                     18

<210> SEQ ID NO 152

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ctgggtccac tcgtcattct                                              20

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ctgggtccac tcgtcattc                                               19

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
atcctgggtc cactcgtcat t                                            21

<210> SEQ ID NO 155
<211> LENGTH: 9
<212> TYPE: PRT
<213> ORGANISM: Unknown
<220> FEATURE:
<223> OTHER INFORMATION: Description of Unknown:
      'LAGLIDADG' family motif peptide

<400> SEQUENCE: 155

Leu Ala Gly Leu Ile Asp Ala Asp Gly
1               5
```